(12) United States Patent
Weber

(10) Patent No.: US 7,909,796 B2
(45) Date of Patent: Mar. 22, 2011

(54) INJECTION DEVICE

(75) Inventor: Wilfried Weber, Schopfloch (DE)

(73) Assignee: Bayer Schering Pharma Aktiengesellschaft, Berlin (DE)

( * ) Notice: Subject to any disclaimer, the term of this patent is extended or adjusted under 35 U.S.C. 154(b) by 1414 days.

(21) Appl. No.: 10/566,659

(22) PCT Filed: Jul. 23, 2004

(86) PCT No.: PCT/DE2004/001649
§ 371 (c)(1),
(2), (4) Date: Feb. 1, 2006

(87) PCT Pub. No.: WO2005/011780
PCT Pub. Date: Feb. 10, 2005

(65) Prior Publication Data
US 2006/0258990 A1 Nov. 16, 2006

(30) Foreign Application Priority Data
Aug. 1, 2003 (DE) .............................. 203 11 996 U

(51) Int. Cl.
*A61M 5/20* (2006.01)
(52) U.S. Cl. ............................................... 604/156
(58) Field of Classification Search ......... 604/130–139, 604/156–158, 192–199, 218, 232
See application file for complete search history.

(56) References Cited

U.S. PATENT DOCUMENTS
6,270,479 B1 * 8/2001 Bergens et al. ............... 604/156
6,638,255 B1 10/2003 Weber FOREIGN PATENT DOCUMENTS
DE 356704 7/1922
FR 2519866 A2 7/1983
FR 2 616 221 12/1988

OTHER PUBLICATIONS
Explanation of Relevance of FR 2 519 866.
* cited by examiner

*Primary Examiner* — Nicholas D Lucchesi
*Assistant Examiner* — Laura A Bouchelle
(74) *Attorney, Agent, or Firm* — Browdy and Neimark, PLLC

(57) ABSTRACT

An injection device for a syringe, having a syringe body, a cannula with a needle, a plunger with a plunger rod, and an injection carriage for displacing the syringe body and the plunger, comprises at least one actuating element that acts on the injection carriage to carry out the injection procedure. The actuating element (120, 220, 320) cooperates with components which withdraw the needle (108, 208, 308) from the puncture site once the injection procedure has been completed, using a return stroke (H3) that is applied to the injection carriage. A single, targeted linear movement inserts the needle to a defined depth, injects the medicament and, once the injection has been completed, produces a return stroke which allows the needle to be withdrawn into the housing and thus out from the puncture site.

31 Claims, 57 Drawing Sheets

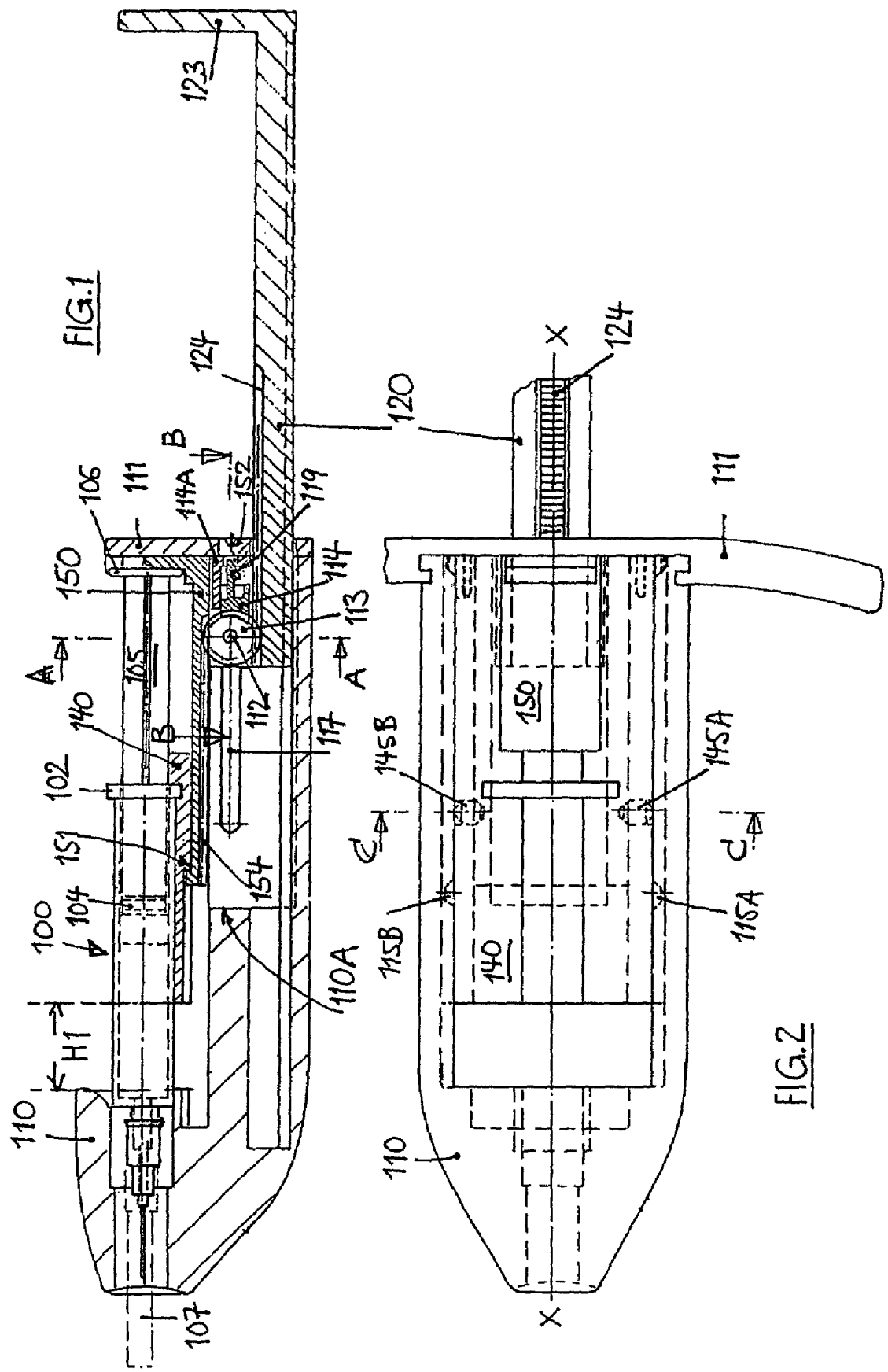

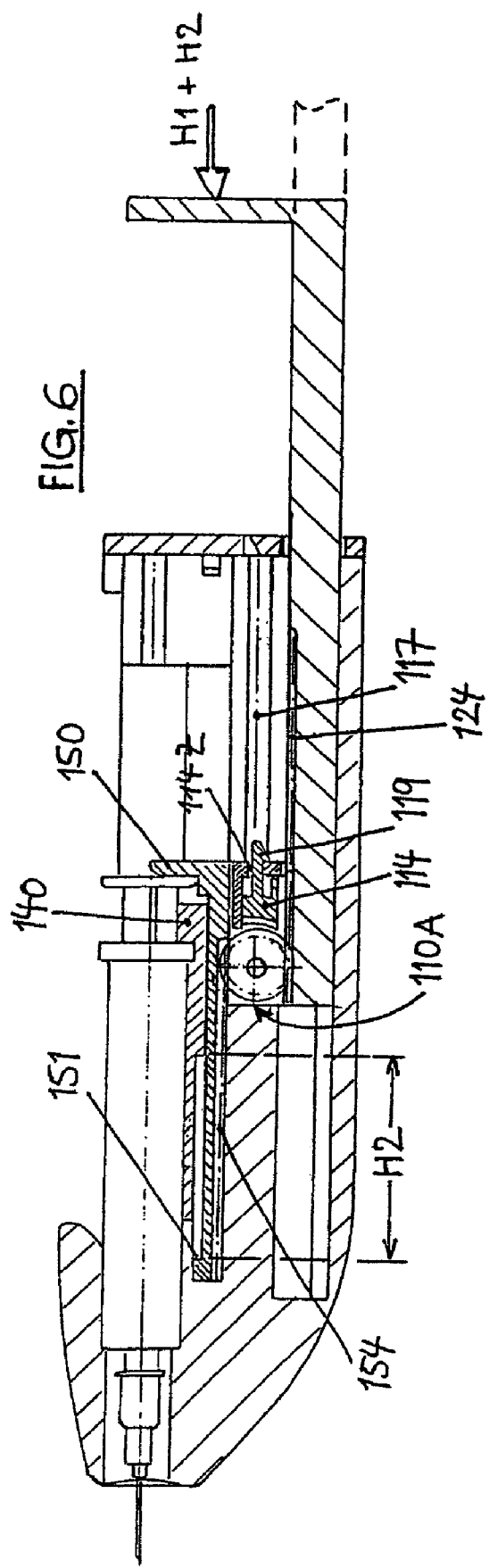
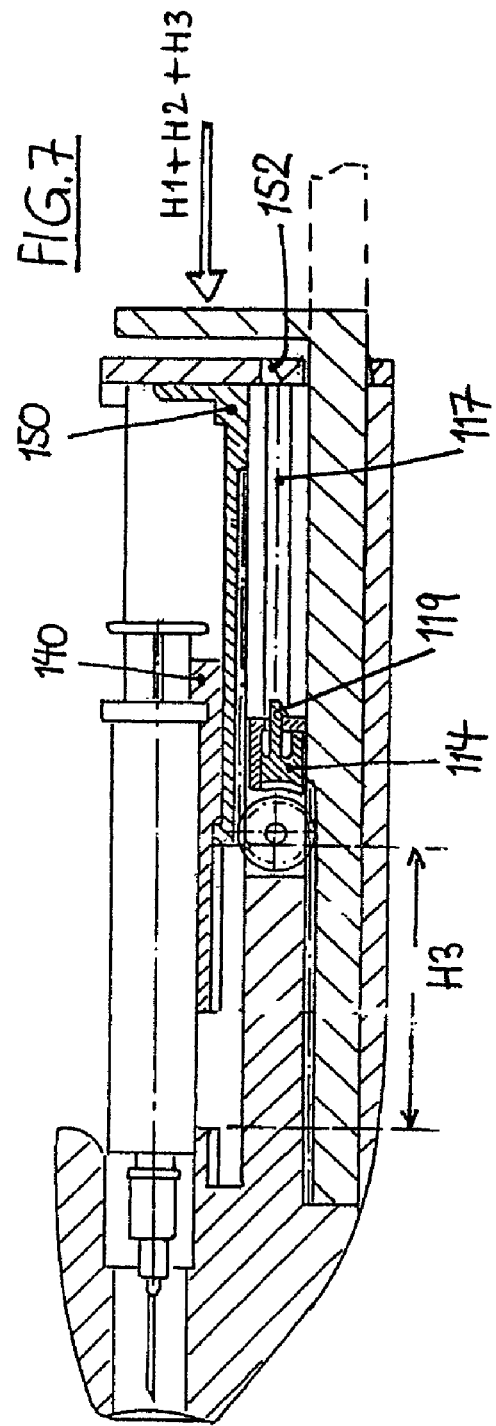

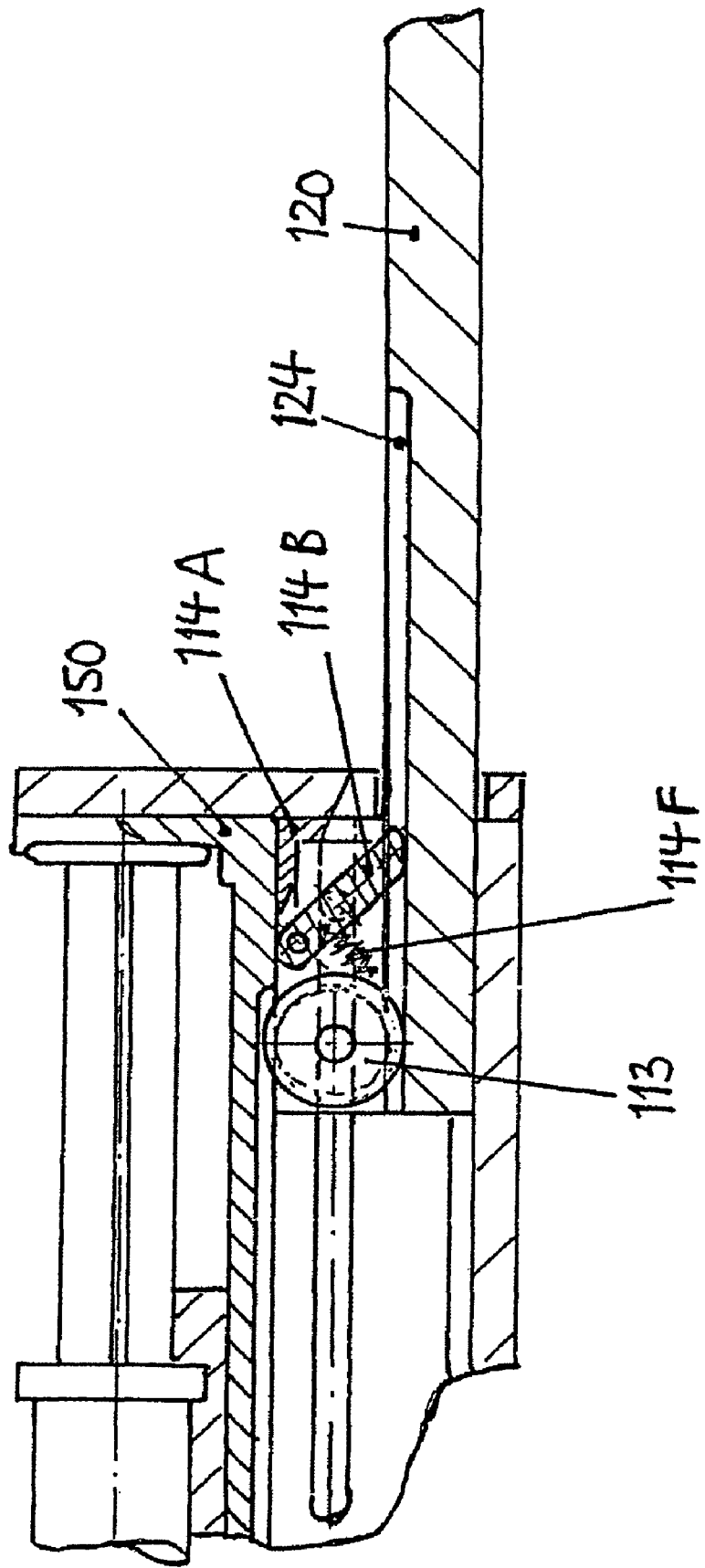

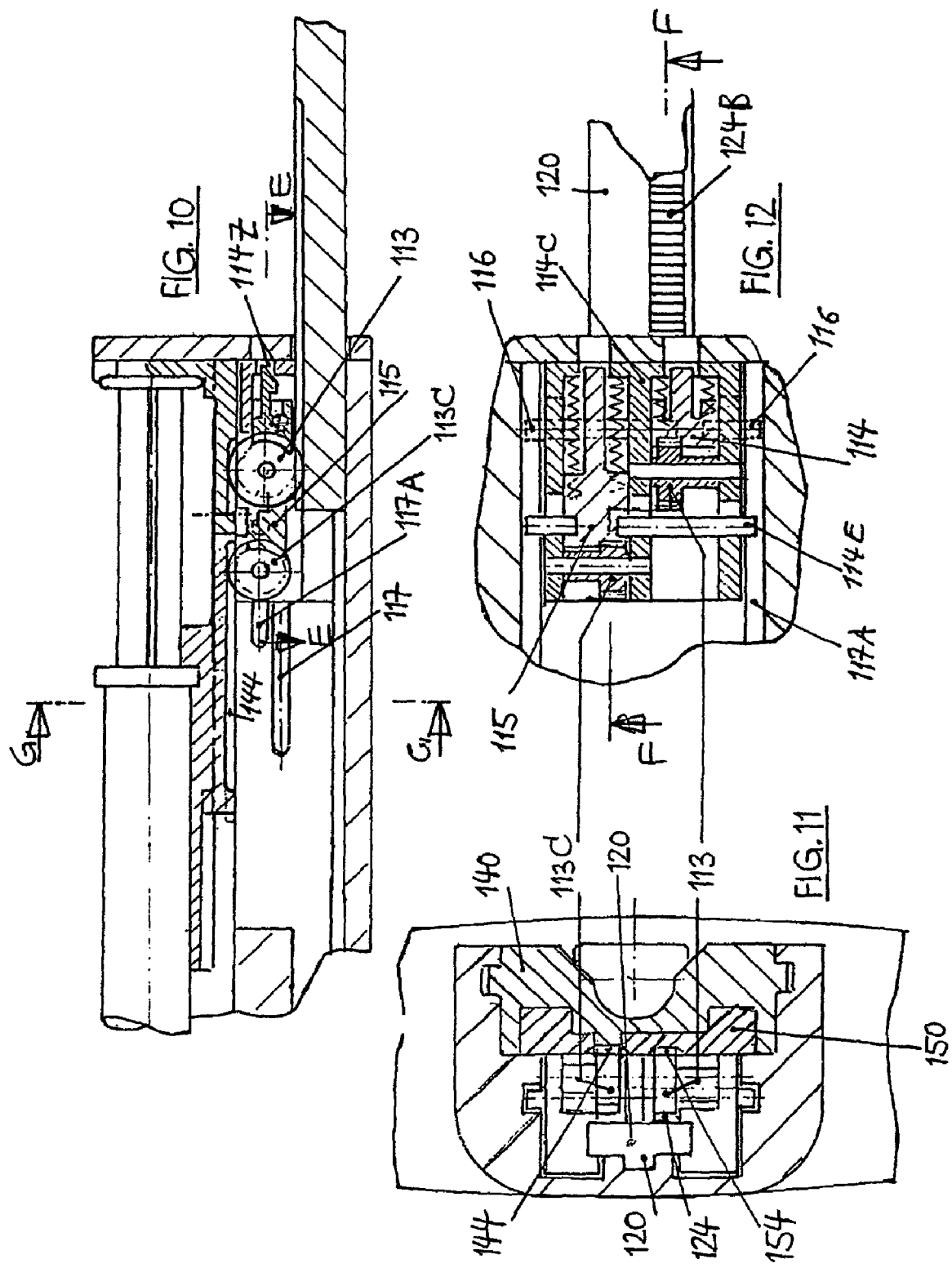

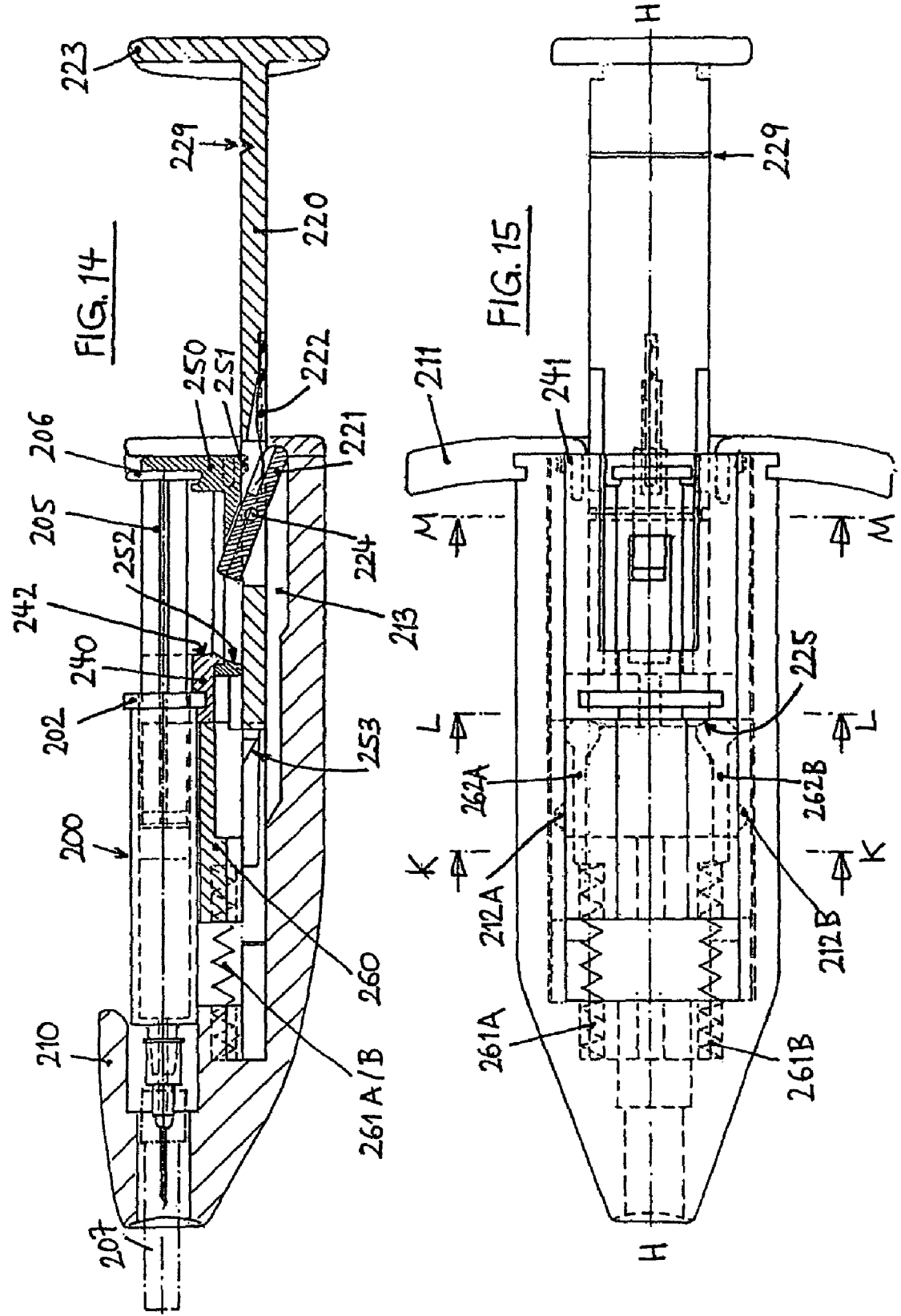

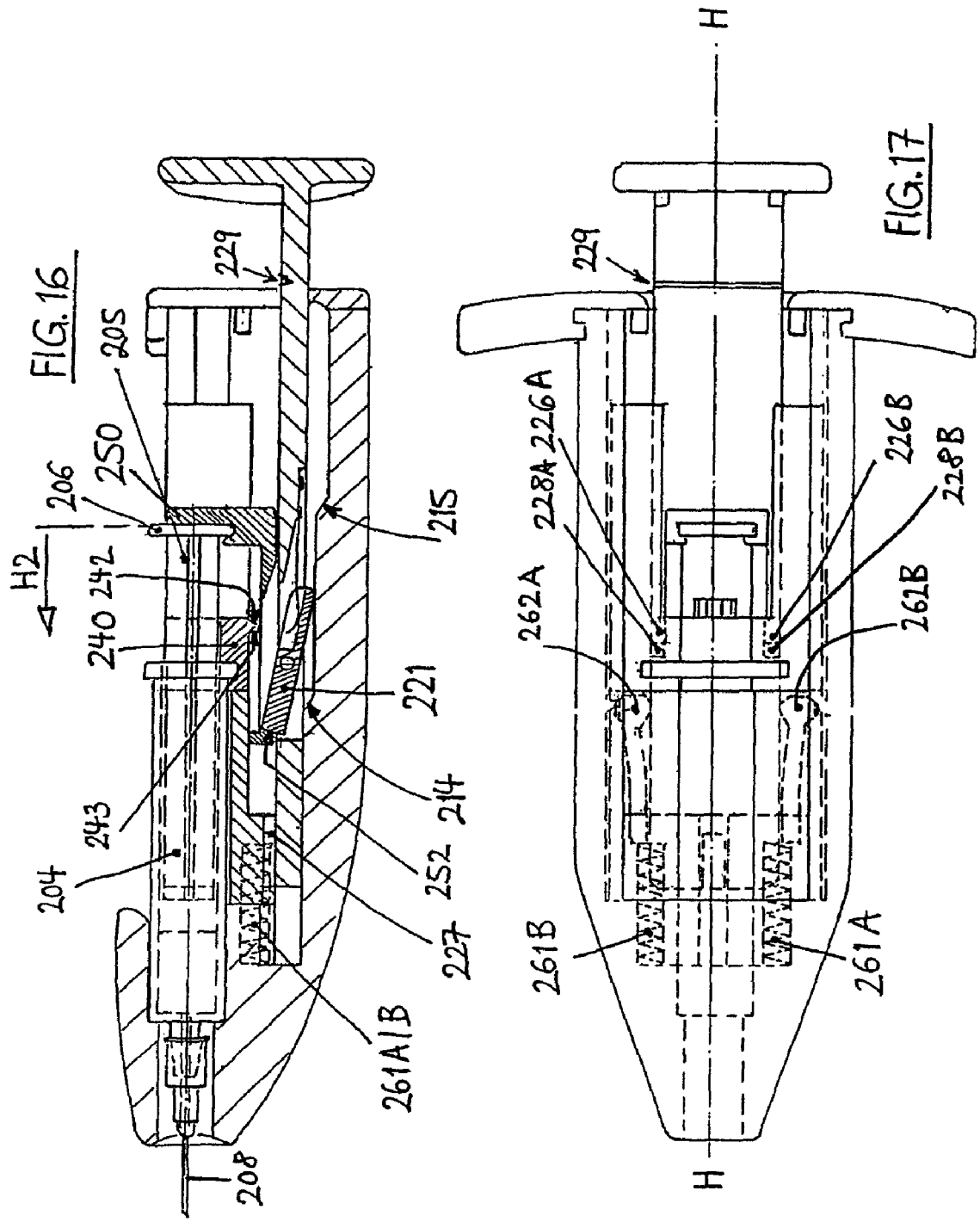

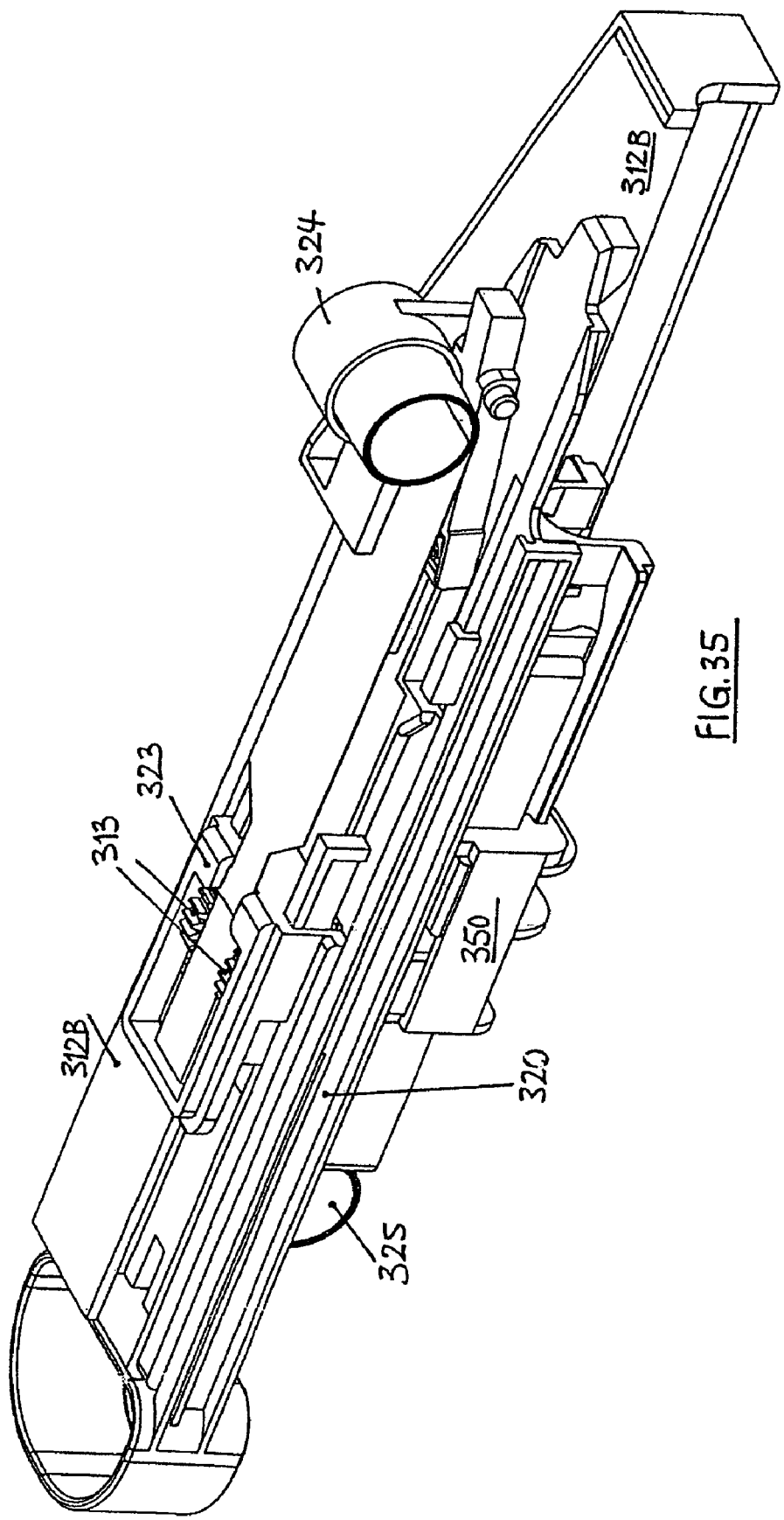

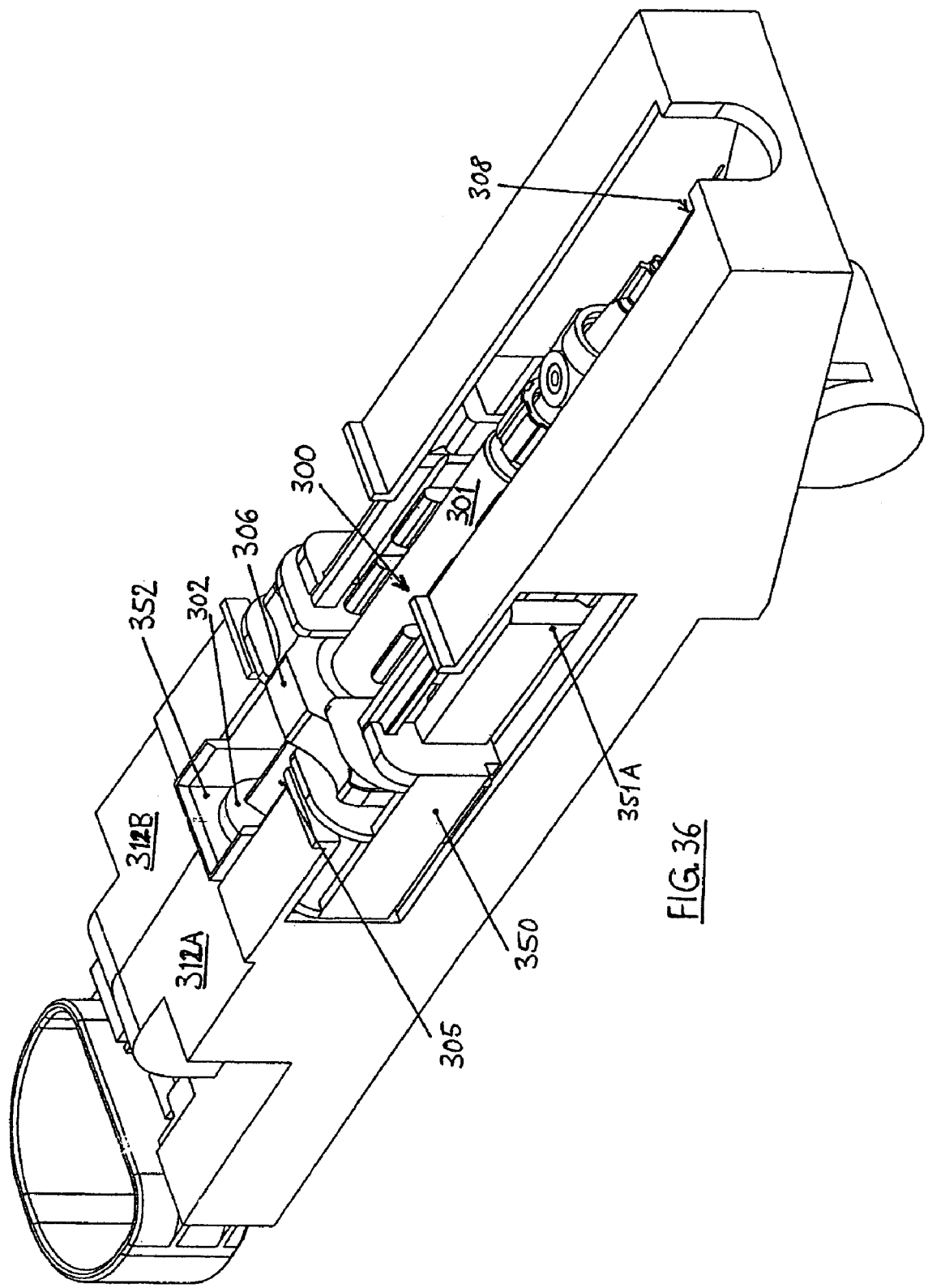

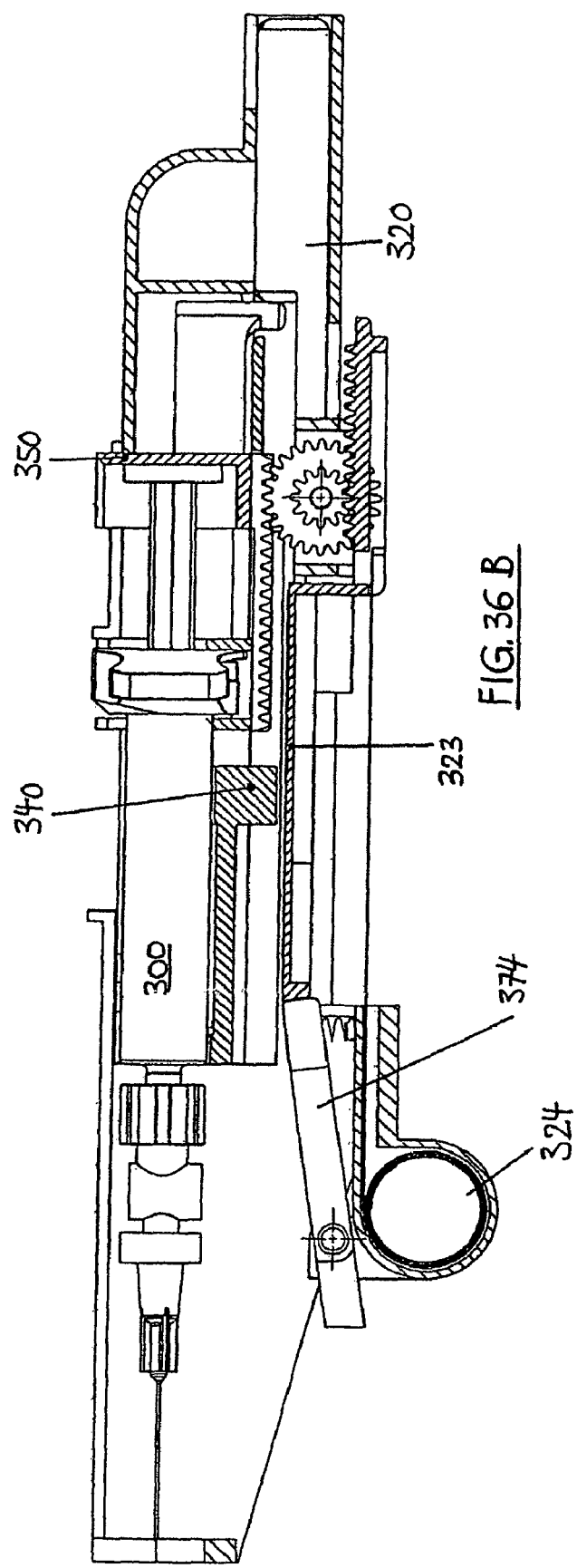

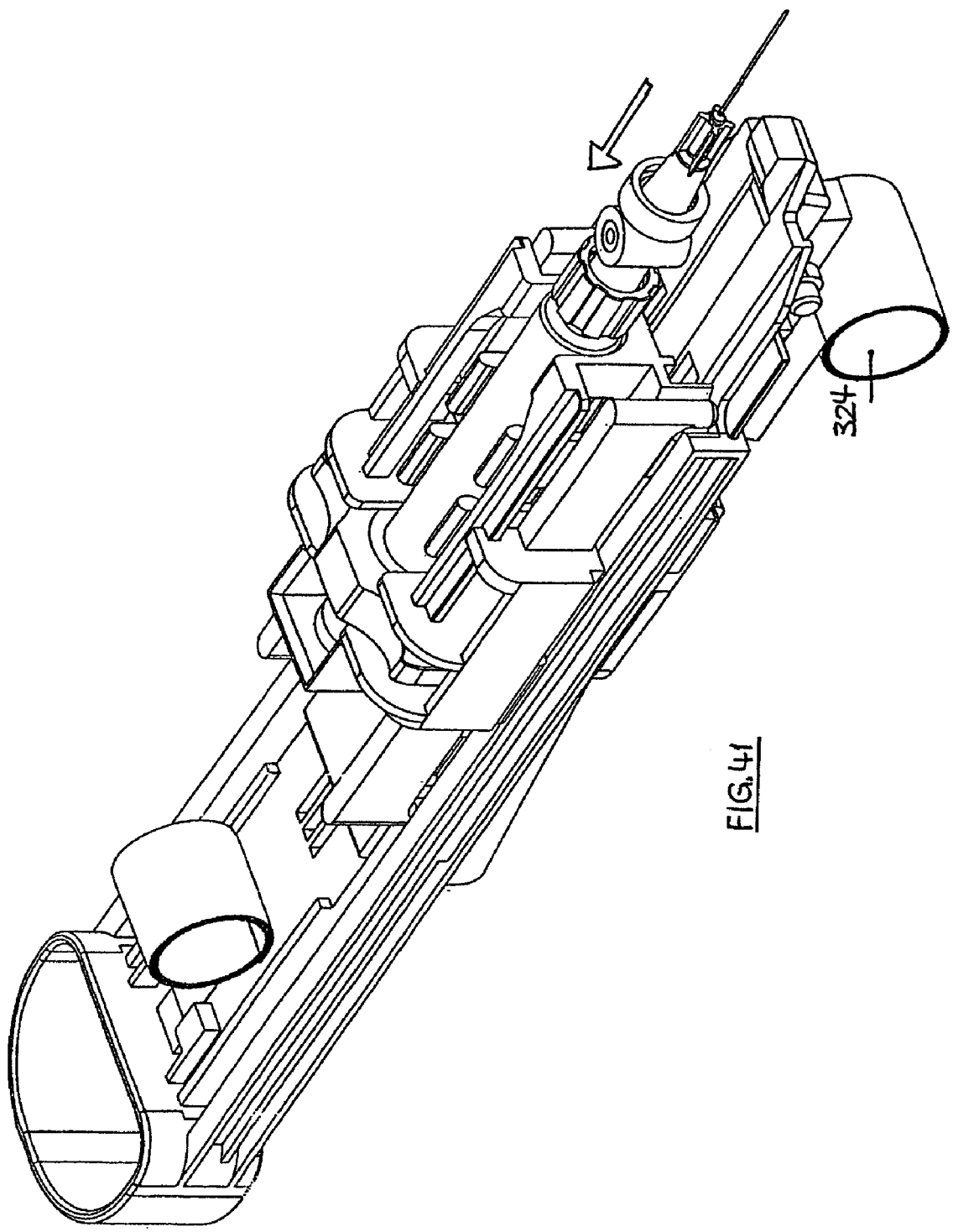

INJECTION DEVICE

TECHNICAL BACKGROUND

Many injection devices are known which allow an inserted syringe to be positioned in such a way as to permit simple insertion into the skin, to the required depth, and injection of the medicament, without the syringe being maneuvered directly by hand. Such an injection device in every case has the purpose of improving the safety of the injection and also the handling comfort, so that injections that are often needed on a daily basis or in some cases even several times a day can be carried out independently by all patients themselves, even without specific training, which also represents a considerable saving in costs.

PRIOR ART

Injection devices are known in which, in order to increase comfort and safety, an automatic sequence of insertion of the syringe needle and subsequent injection is carried out, for example as is known from EP 1 233 801. After the injection has been completed, the injection device has to be moved away from the puncture site by the patient in order to withdraw the needle. This must be done as far as possible perpendicularly in relation to the surface of the skin and with a steady hand, in order to avoid injuries from the needle. In the known devices, this is not guaranteed. On the contrary, in extreme cases, safe removal of the needle is made even more difficult by the much greater inherent weight of the injection device compared to a syringe.

DISCLOSURE OF THE INVENTION

The object of the invention is to make the handling of an injection device after completion of the injection easier and safer.

This object is achieved according to the features of claim 1.

The invention thus makes available an injection device which, by means of a single, targeted linear movement, inserts the needle to a defined depth, injects the medicament and, once the injection has been completed, produces a return stroke, which withdraws the needle into the housing and thus out from the puncture site. The drive force for the linear movement can be produced manually, either directly or by intercalation of energy accumulators.

An acoustic signal can be generated at the end of the return stroke. Following this acoustic signal, the patient can lift the entire injection device away from the injection site without special precaution or attention, because the needle has been withdrawn from the insertion site.

After the injection has been completed, the needle does not protrude from the injection device, and for this reason there is also no longer any risk of injury when handling the injection device after the injection.

If the protective cap is removed following insertion of the syringe, and if the protective cap is put back on again after the injection procedure, and before removal of the syringe, then the patient at no time sees the needle, neither before nor after the injection, in the case of a prefilled syringe, a fact which facilitates handling of the injection device, particularly for those patients who suffer from what is called "needle phobia".

Advantageous developments of the injection device according to the invention are set forth in the dependent claims.

BRIEF DESCRIPTION OF THE DRAWINGS

Several illustrative embodiments of the injection device according to the invention are now explained in more detail with reference to figures, in which:

FIG. 1 shows a first illustrative embodiment in a first longitudinal section in the plane X-X from FIG. 2, in the stand-by position with inserted syringe, FIG. 2 shows the first illustrative embodiment in a view without the syringe, FIG. 6 shows a second longitudinal section in the injection position after completion of the insertion stroke and injection stroke, FIG. 7 shows a third longitudinal section after completion of the return stroke, FIG. 9 shows a partial section corresponding to FIG. 1 through a second variant of the first illustrative embodiment, FIG. 10 shows a partial section corresponding to FIG. 1 in the plane F-F from FIG. 12 through a third variant of the first illustrative embodiment, FIG. 11 shows a section in the plane G-G from FIG. 10, FIG. 12 shows a section in the plane E-E from FIG. 10, FIG. 14 shows a second illustrative embodiment in a first longitudinal section in the plane H-H from FIG. 15, in the stand-by position with inserted syringe, FIG. 15 shows the second illustrative embodiment in a first view without syringe, FIG. 16 shows a second longitudinal section in the plane H-H from FIG. 17, after the insertion stroke and during the injection stroke, FIG. 17 shows a second view according to FIG. 15 (without syringe) during the injection stroke, FIG. 35 shows a perspective view of the underside with one half of the receiving frame according to FIG. 24, FIG. 36 shows a perspective view of essential operating components in the start position, with inserted syringe, FIG. 36B shows a second longitudinal section through the operating components according to FIG. 36, FIG. 41 shows a perspective partial view of essential operating components during the return stroke, FIG. 47B shows a second longitudinal section through the operating components in their position according to FIG. 47.

DESCRIPTION OF THE ILLUSTRATIVE EMBODIMENTS

Figure 3:
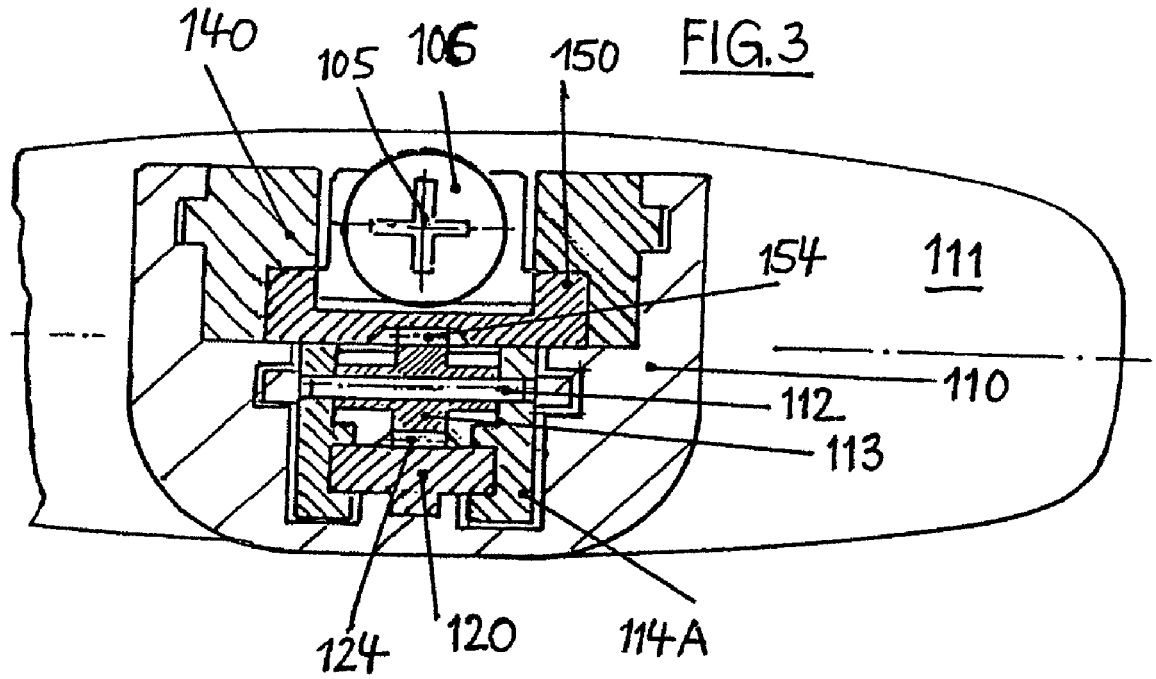
FIG. 3 shows a section in the plane A-A from FIG. 1.
Figure 4:
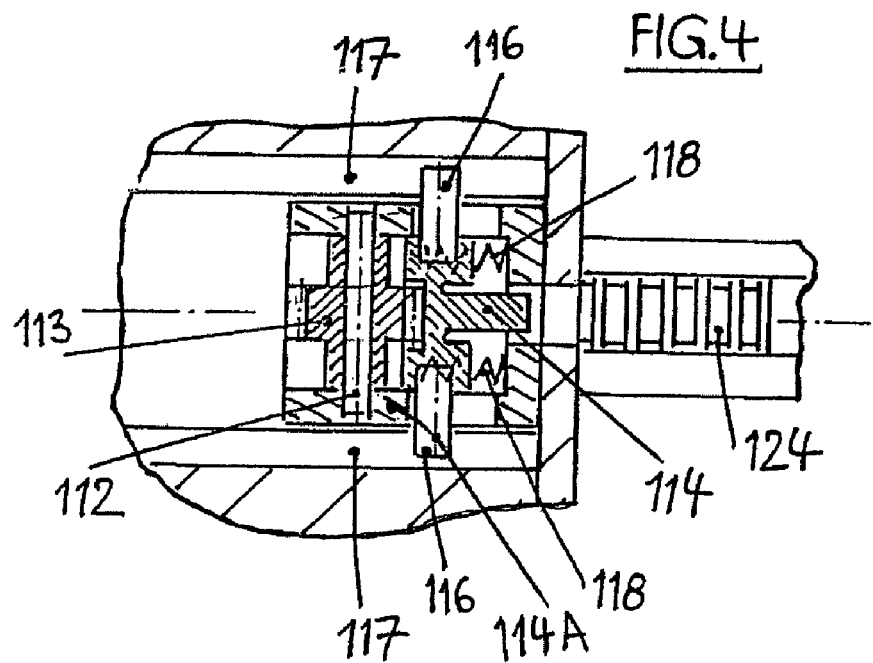
FIG. 4 shows a partial section in the plane B-B from FIG. 1.

Four illustrative embodiments are described below. In all of the illustrative embodiments, the basic structure of the injection device is as follows:

The syringe with plunger, plunger rod and cannula with needle is inserted into a syringe holder, with the aid of which the insertion stroke H1 is effected, i.e. the insertion of the needle into the injection site. For this purpose, the syringe holder is mounted in an axially displaceable manner in a housing. To actuate the syringe after the insertion stroke, i.e. to inject the medicament, a ram is used which is mounted displaceably relative to the syringe holder and which acts on the plunger of the syringe (injection stroke H2). Syringe holder and ram are coupled releasably to one another in such a way that the injection stroke H2 begins immediately after the insertion stroke H1, i.e. during the insertion stroke H1 the syringe holder and ram are rigidly connected to one another and move forward together in the housing, whereas, during the injection stroke H2, the coupling is released, the syringe holder remains in the housing and only the ram continues to move forward.

Syringe holder and ram together form the injection carriage.

After the injection has been completed, the injection carriage, in accordance with the invention, is drawn back again to its starting position (return stroke H3) and the needle is withdrawn completely from the skin.

To control this sequence (insertion stroke H1, injection stroke H2, return stroke H3), an actuating element is provided which for its part is made up of several components and which serves to convert an action exerted by the patient into the movements of the injection carriage in a positionally and directionally defined manner. The components contained in the actuating element are, for example, toothed wheels, push rods, springs and similar elements which serve for the direct or stored movement coupling and production.

In terms of their function, the four illustrative embodiments differ mainly in the way the required actuating work is applied by the patient and the way in which it is converted into insertion stroke H1, injection stroke H2 and return stroke H3. Accordingly, different locking and coupling elements (lugs, tongues, recesses, limit stops, etc.) are positioned in order to link the work sequences into one another in a manner depending on the position of the movable components relative to one another.

In the first illustrative embodiment (FIGS. 1-13), the conversion takes place directly, i.e. the actuating element essentially comprises a push rod whose continuous pushing into the housing, by the patient, brings about the succession of movements of the injection carriage, the movements of the push rod and of the injection carriage being in opposite directions at the change from the injection stroke H2 to the return stroke H3.

In the second illustrative embodiment (FIGS. 14-20) the movement of the actuating element (push rod) is used, before actuation of the injection carriage, to load a spring accumulator which provides the work for returning the injection carriage as required for the return stroke H3. The abrupt triggering of the return stroke H3, by release of the spring energy, has the advantage of a pulse-like withdrawal of the needle from the skin and therefore minimizes still further the above-described disadvantages of the known injection devices.

In the third illustrative embodiment (FIGS. 21-47), the concept of the spring accumulator is developed to the extent that all the movements of the injection carriage are occasioned by spring accumulators; the actuating element for this purpose comprises a pull-out loading bar whose actuation by the patient, before the injection device is placed on the skin, stores the total energy for insertion stroke H1, injection stroke H2 and return stroke H3 in these spring accumulators, from which they are then called upon by the corresponding components in the housing during the movement sequence depending on position. In this solution, the entire sequence, in terms also of its speed and the duration of the individual strokes H1, H2, H3, is made independent of the specific nature of the actuation by the patient, because, with the triggering of the injection device by means of a trigger button, for example, the sequences are predetermined by the dimension of the structural parameters, for example the choice of the spring properties, and cannot be influenced by the patient. In this way, it is also possible in terms of the insertion stroke H1 and of the injection stroke H2 to optimize them, for example in terms of their duration, for example by adapting them to the thickness of the needle or to injection settings for a specific medicament.

The structural configuration of the essential components is shown several times in the drawings and is therefore explained below on the basis of the function of these components. It goes without saying that the detailed configurations of the components are to a large extent variable, on condition that it is possible to guarantee in particular that the start and end of the strokes H1, H2, H3 are clearly defined by suitable coupling/decoupling of the components provided for this purpose, and that the energy required in each case for this purpose is made available with precise timing, whether by direct conversion of the movement of a push rod, or by calling on an accumulated store of energy.

First Illustrative Embodiment

The component groups in the first illustrative embodiment will now be described briefly below:

The actuating element comprises a push rod 120 with a flange plate 123 arranged at the rear, which is guided lengthwise in the housing 110. On its top, the push rod 120 has teeth 124 in which a toothed wheel 113 engages which is mounted in a carriage 114A. The underside of the ram 150 has corresponding teeth 154 in which the toothed wheel 113 likewise engages.

The turning of the toothed wheel 113 can be blocked or freed by means of a blocking slide 114 with locking hook 119 in the carriage 114A. In the blocked position, the linear movement of the push rod 120 is thus converted directly into an identical linear movement of the ram 150 which, depending on its coupling to the syringe holder 140, then travels forward together with the latter (insertion stroke H1) or on its own (injection stroke H2). After the injection, the blocking of the toothed wheel 113 is canceled, and the onward movement of the push rod 120 is converted into an oppositely directed displacement of the ram 150, which entrains the syringe holder 140 and thus pulls the syringe 100 with its needle 108 out from the puncture site.

The detailed configuration and the interaction of these components will become clear from the following description of their functions:

The syringe 100 is introduced with protective cap 107 into the housing 110 and is fixed with its syringe collar 102 in the syringe holder 140.

After the protective cap 107 has been removed and the injection device has been placed on the injection site, then, as is customary when using a syringe, two fingers are placed under the holding plate 111, which is connected positively to the housing 110, and the thumb is used to apply pressure to the flange plate 123 of the push rod 120.

It is also conceivable to design the injection device as a complete housing, e.g. with a hinged lid or sliding lid, so that, with one hand, the user grips the injection device and places it on the injection site and, with the other hand, presses on the actuating element.

Figure 5:
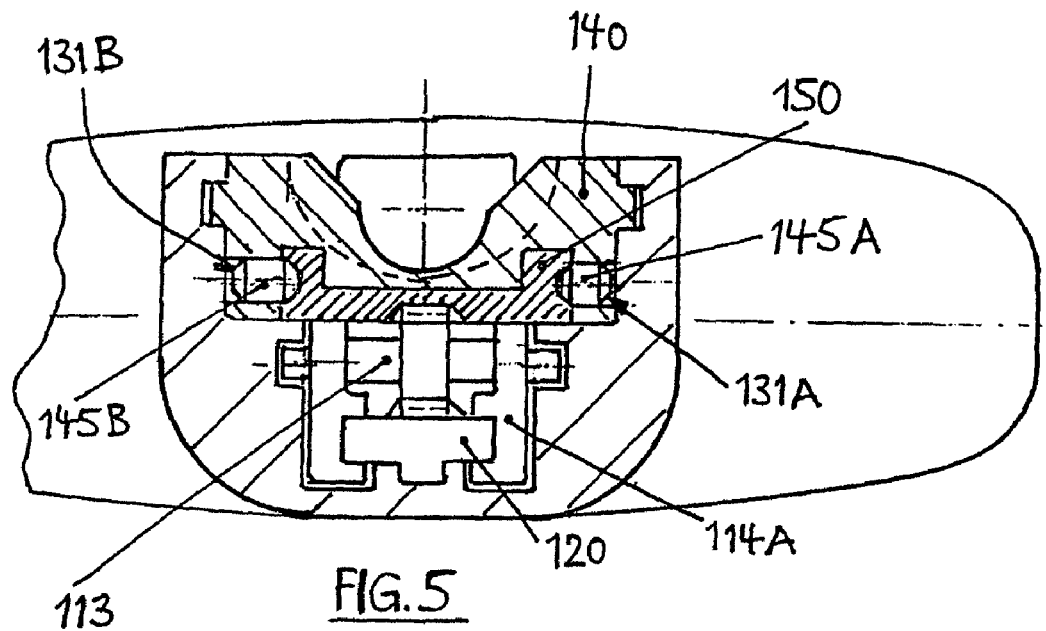
FIG. 5 shows a section in the plane C-C from FIG. 2.
Figure 8:
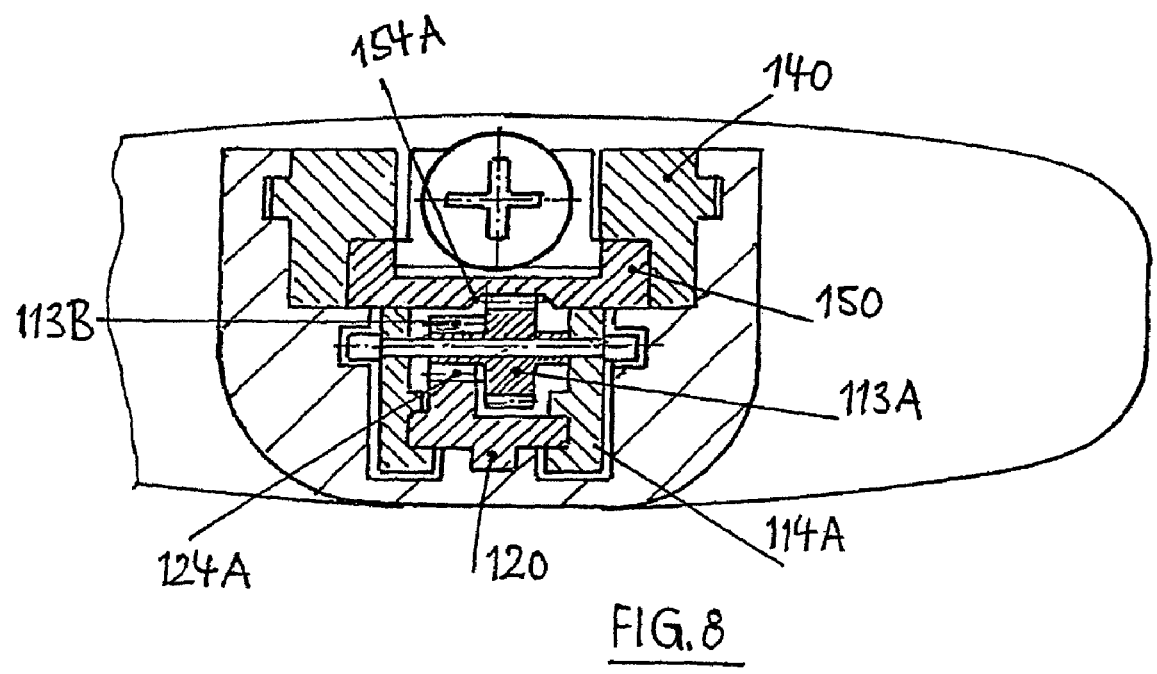
FIG. 8 shows a section corresponding to FIG. 3 through a first variant of the first illustrative embodiment with a gear.

The syringe holder 140 and the ram 150 are connected positively to one another via slide blocks 145A, 145B as the coupling element (see FIG. 5).

The toothed wheel 113 mounted in the housing 110 by way of a shaft 112 in the carriage 114A is in engagement with the teeth of the blocking slide 114, such that the toothed wheel 113 is blocked against turning. The carriage 114A is for its part longitudinally displaceable in the housing 110, with carriers 116 sliding in a groove 117. The teeth on the actuating element 120 and on the ram 150 are likewise in engagement with the toothed wheel 113. This results in a rigid connection between push rod 120 and ram 150 (see FIGS. 3 and 4).

When a force is applied by the thumb to the flange plate 123 and this force is greater than the retaining force of a locking hook which fixes the syringe holder 140 in the housing 110, the syringe holder 140 and the ram 150, being connected with positive engagement via the slide blocks 145A, 145B, move toward the injection site in synchrony with the push rod 120. The needle 108 punctures the tissue to the predetermined depth (insertion stroke H1) without the plunger 104 of the syringe 100 being actuated.

At the end of the insertion stroke H1, the slide blocks 145A, 145B reach recesses 115A, 115B in the housing 110. As a result of the conversion of force by bevels 131A, 131B, the slide blocks 145A, 145B slide into their associated recess 115A, 115B, fix the syringe holder 140 with form fit in the housing 110, and thereby cancel the rigid coupling between syringe holder 140 and ram 150.

Driven further by the push rod 120, the ram 150 is now moved onward to the injection site, the plunger 104 in the syringe body 101 being moved via the flange 106 and plunger rod 105, and the medicament thus being injected (injection stroke H2).

At the end of the injection stroke H2, the carriers 116 on both sides of the blocking slide 114 strike the end of the groove 117. The blocking slide 114 is displaced counter to the spring force from two compression springs 118, the blocking of the toothed wheel 113 is released, the locking hook 119 engages in an opening 114Z of the carriage 114A. The carriage 114A of the toothed wheel 113 then strikes a limit stop 110A in the housing 110 (see FIG. 6).

Since the toothed wheel 113 is unblocked in this position, and the carriage 114A can move axially onto the actuating element 120, the toothed wheel 113 turns when the actuating element 120 is displaced further in the direction of the injection site. The ram 150 moves away from the injection site without the plunger rod 105 being moved.

Once the ram 150 has traveled a distance which corresponds in terms of magnitude to the injection stroke H2, the syringe holder 140 is entrained via a limit stop 151, the slide blocks 145A, 145B move and couple the ram 150 once again to the syringe holder 140, so that now, via the syringe collar 102, the syringe 100 and thus the needle 108 cover a return stroke H3 which corresponds in terms of magnitude to the insertion stroke H1 (see FIG. 7).

The distance between the flange plate 123 of the actuating element 120 and the retaining plate 111 can now be reduced no further; syringe holder 140 and ram 150 have been moved back to their starting position.

The syringe 100 can now be directly removed, or the push rod 120 can first be drawn back into its starting position and the syringe then removed.

When the push rod 120 is drawn back, the toothed wheel 113 rolls on the teeth 154 of the ram 150 and on the teeth 124 of the push rod 120.

The carriage 114A thus moves relative to the push rod 120.

Shortly before the end of the return of the push rod 120, the locking hook 119 moves against a bevel 152, and in this way the locking is released, compression springs 118 push the blocking slide 114 once more against the toothed wheel 113. The toothed wheel 113 is thus once again blocked against rotation, and a rigid connection is again obtained between push rod 120 and ram 150.

In a first variant of this illustrative embodiment (FIG. 8), two toothed wheels 113A, 113B are designed as gears in the carriage 114A, such that a transmission ratio of the movements of push rod 120 and ram 150 is defined which shortens the path of the push rod 120 and/or permits a more rapid return stroke.

The larger toothed wheel 113A meshes with the teeth 154A of the ram 150, while the smaller toothed wheel 113B meshes with the teeth 124A of the push rod 120.

As soon as the pair of toothed wheels 113A, 113B is unblocked (at the end of the injection stroke H2), the return stroke H3 of the ram 150 is geared in relation to the reference diameter of the two toothed wheels 113A, 113B.

In a second variant of the first illustrative embodiment (FIG. 9), a lever 114B acted upon by a spring 114F is provided for blocking/freeing the toothed wheel 113.

The function of the blocking slide 114 is in this case achieved by a releasable fixation of the carriage 114A, in which the toothed wheel 113 is mounted, on the respective teeth of the push rod 120 and/or of the ram 150.

At its end remote from the bearing point, the lever 114B, which is mounted rotatably in the carriage 114A, engages in the teeth 124 of the push rod 120.

As long as the lever 114B prevents displacement of the carriage 114A on the push rod 120, there is a rigid connection between the push rod 120 and the ram 150.

Toward the end of the injection stroke H2, a carrier strikes against the end limit stop of the groove 117, the lever 114B is pivoted out from the teeth 124 of the push rod 120 counter to the tensile force of the spring 114F, while at the same time the carriage 114A strikes against the limit stop 110A (see FIG. 6), so that the toothed wheel 113 can now turn and the return stroke H3 starts.

Instead of this solution, it is also possible for a spring-operated pivot lever to be mounted in the carriage 114A, its pawl engaging in the teeth of the toothed wheel 113.

A third variant of this solution principle of the first illustrative embodiment is shown in FIGS. 10-12:

In this variant of the first illustrative embodiment, the coupling between ram 150 and syringe holder 140, which together form the injection carriage, is provided by an additional toothed wheel 113C which is mounted in a common carriage 114C, likewise displaced by the push rod 120.

In the starting position, the toothed wheel 113C is blocked by a further blocking slide 115, and the toothed wheel 113 by the blocking slide 114.

The toothed wheel 113C meshes with teeth 144 on the syringe holder 140, and the toothed wheel 113 meshes, as described above, with the teeth 124 on the actuating element 120 and the teeth 154 in the ram 150.

Upon movement of the push rod 120, a rigid connection of the push rod 120 to the syringe holder 140 and to the ram 150 is obtained as a result of the blocked toothed wheels 113, 113C.

Syringe holder 140, carriage 114C and ram 150 are therefore moved simultaneously with the push rod 120 to the injection site, until carriers 114E reach a limit stop in the groove 117A and unblock the toothed wheel 113C by displacement of the blocking slide 115. The toothed wheel 113C can now turn, and the syringe holder 140 is not moved any farther.

The toothed wheel 113 still remains blocked, therefore the ram 150 moves in unison with the push rod 120 until carriers 116 reach the limit stop in the groove 117. The reverse movement then takes place, as has been described above.

As soon as the push rod 120 is pulled back again into its starting position, both toothed wheels 113, 113C are again blocked.

Figure 13:
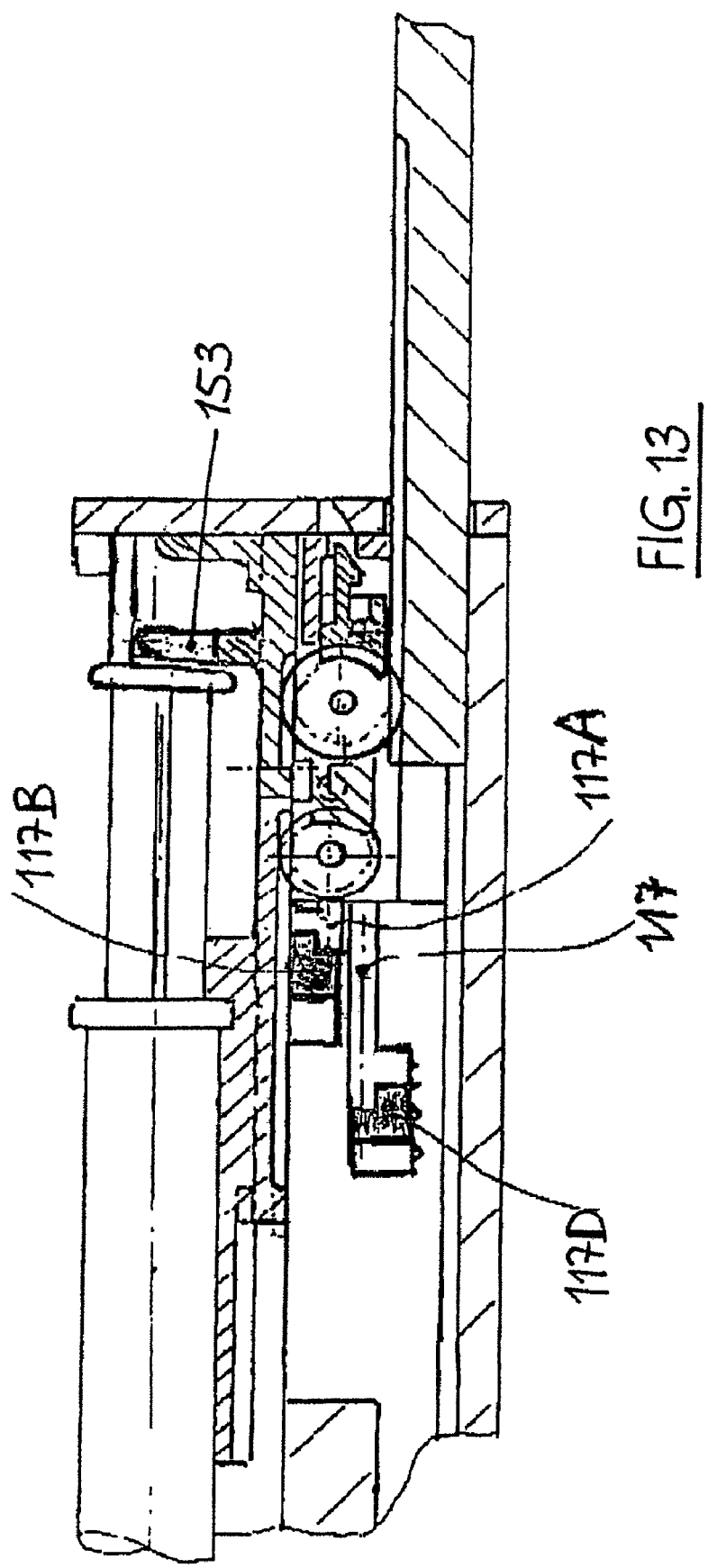
FIG. 13 shows a partial section corresponding to FIG. 10 through a fourth variant of the first illustrative embodiment.
Figure 18:
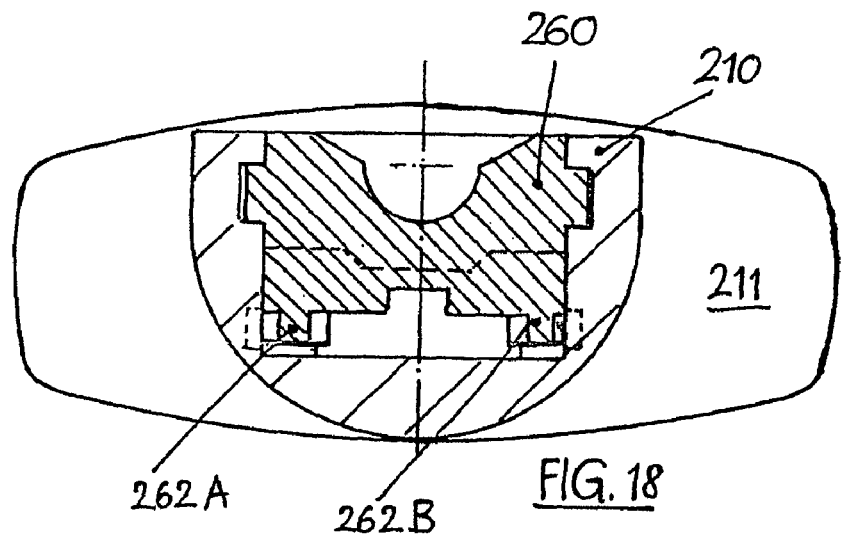
FIG. 18 shows a section in the plane K-K from FIG. 15.
Figure 19:
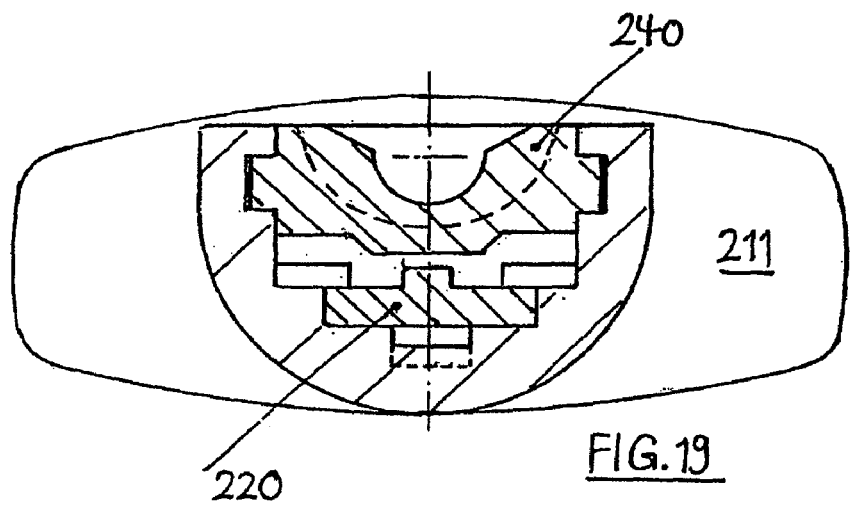
FIG. 19 shows a section in the plane L-L from FIG. 15.
Figure 20:
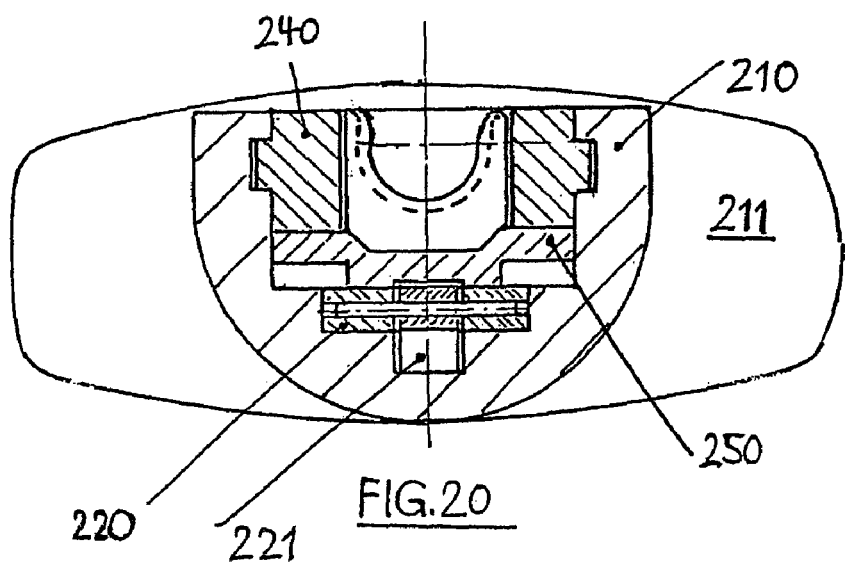
FIG. 20 shows a section in the plane M-M from FIG. 15.

A fourth variant of this solution principle of the first illustrative embodiment is shown in FIG. 13:

The path of the carriers 114E as far as the limit stop in the groove 117A determines the insertion stroke H1.

The limit stop in the groove 117A can be modified by a slide 117B. Thus, the depth of insertion can be varied within a defined range. For example, with a cannula measuring 16 mm (needle length 16 mm), a depth of insertion of just 12 mm could be achieved by displacement of the slide 117B.

In the same way, the injection stroke H2 can be varied by a modifiable limit stop 117D in the groove 117.

By configuring the ram 150 with one or more U-shaped webs 153, it is possible, using this principle of a groove of adjustable length, to administer different injection volumes.

Second Illustrative Embodiment

The second illustrative embodiment is shown in FIGS. 14-20. The component groups of the second illustrative embodiment will now be described in brief below:

In addition to the above-described components (push rod 220, syringe holder 240 and ram 250), a return carriage 260 is coupled to the injection carriage and bears by means of compression springs 261A, 261B on a limit wall of the housing 210.

The sequence of the strokes H1 and H2 is controlled by a spring-actuated control lever 221 mounted pivotably in the push rod 220. At the end of the injection stroke H2, the push rod 220, as described below, frees the return carriage 260 which is now pretensioned against the compression springs 261A, 261B and which then independently executes the return stroke H3.

The syringe 200 is inserted with protective cap 207 into the housing 210 in a pivoting movement and is fixed with its syringe collar 202 in the syringe holder 240 and with the flange 206 of the plunger rod 205 in the ram 250.

After the protective cap 207 has been removed and the injection device has been placed on the injection site, two fingers are also in this case placed under the holding plate 211, and the thumb is used to exert force on the flange plate 223 of the actuating element 220.

At its front end, the push rod 220 is provided with bevels 225 which press against locking tongues 262A, 262B of the return carriage 260. The radial force component acting via the bevels 225 on the locking tongues 262 bears on the housing wall. By this means, the return carriage 260 moves toward the injection site counter to the force of the compression springs 261A, 261B.

The syringe remains in its position, however, since the syringe holder 240 and the ram 250 are not at this point coupled to the push rod 220.

To ensure that it is not inadvertently displaced by frictional forces or by the force of gravity in the case of a perpendicular injection, the syringe holder 240 is secured by locking tongues 241 on the syringe holder 240 which engage in the housing 210. The ram 250 is likewise secured by the locking tongues 251, which also engage in the housing 210.

Once the push rod 220 has traveled the distance required for tensioning the return carriage 260, the locking tongues 262A, 262B can deflect into the recesses 212A, 212B in the housing 210, the positive engagement between the locking tongues 262A, 262B and the push rod 220 is canceled, and the return carriage 260 is fixed with positive engagement in the housing 210.

During the tensioning of the return carriage 260, the control lever 221, which is acted on by a leaf spring 222 with a rightward moment (which, however, does not lead to a rotation because the control lever 221 bears in a groove 213 in the housing 210), moves as far as the aligned walls of a first limit stop 242 of the syringe holder 240 and of a second limit stop 252 of the ram 250.

The force that can be felt via the thumb on the push rod 220 increases linearly during the tensioning stroke of the return carriage as a result of the spring characteristic of the compression springs 261A, 261B.

The force exerted by the thumb at the moment of deflection of the locking tongues 262A, 262B into the recesses 212A, 212B is now transmitted via the control lever 221 and via the first limit stop 242 to the syringe holder 240 and to the ram 250.

The locking tongues 241, 251 deflect, the syringe holder 240 and ram 250 move in the direction of the injection site in unison with the syringe, but abruptly as a result of the force impulse. The needle 208 thus moves by the insertion stroke H1 (FIG. 16).

At the end of the insertion stroke H1, which must be smaller than or equal to the tensioning path, the control lever 221 is turned counterclockwise by a first bevel 215 in the groove 213 and, in this way, the positive engagement of control lever 221 and syringe holder 240 at the first limit stop 242 is canceled.

The fact that the positive engagement with the ram 250 via the second limit stop 252 is maintained means that, upon further pushing of the push rod 220 via the flange 206 and the plunger rod 205, the plunger 204 of the syringe 200 now moves and the medicament is injected.

As soon as the end of the injection stroke H2 is reached, the control lever 221 is turned counter-clockwise through further angle degrees by a second bevel 214 and, in this way, the positive engagement between the second limit stop 252 of the ram 250 and the control lever 221 is also canceled.

At the same time, or after an additional travel of the push rod 220, the locking tongues 262A, 262B deflect into recesses 226A, 226B on the push rod 220. In this way, the positive engagement between return carriage 260 and housing 210 is canceled and, as a result of the force of the compression springs 261A, 261B, the return carriage 260, the syringe holder 240, the ram 250 and thus the syringe 200 are moved away from the injection site.

The needle 208 is necessarily withdrawn from the body, and the syringe 200 is brought to its starting position.

In this process, the position of the push rod 220 does not change.

The syringe 200 can then be removed, or the push rod 220 can be drawn back into its starting position and the syringe then removed.

When the push rod 220 is drawn back into its starting position, a limit stop 227 carries the ram 250, and the latter carries the syringe holder 240 via a limit stop 243 into its starting position. At the same time, the locking tongues 262A, 262B are deflected upward by means of bevels 228A, 228B, slide over the push rod 220 and engage behind the push rod 220 as soon as the latter has reached its end position.

With the aid of a marking 229, it is possible to visually check whether the push rod 220 is once again situated in its starting position.

Third Illustrative Embodiment

Figure 21:
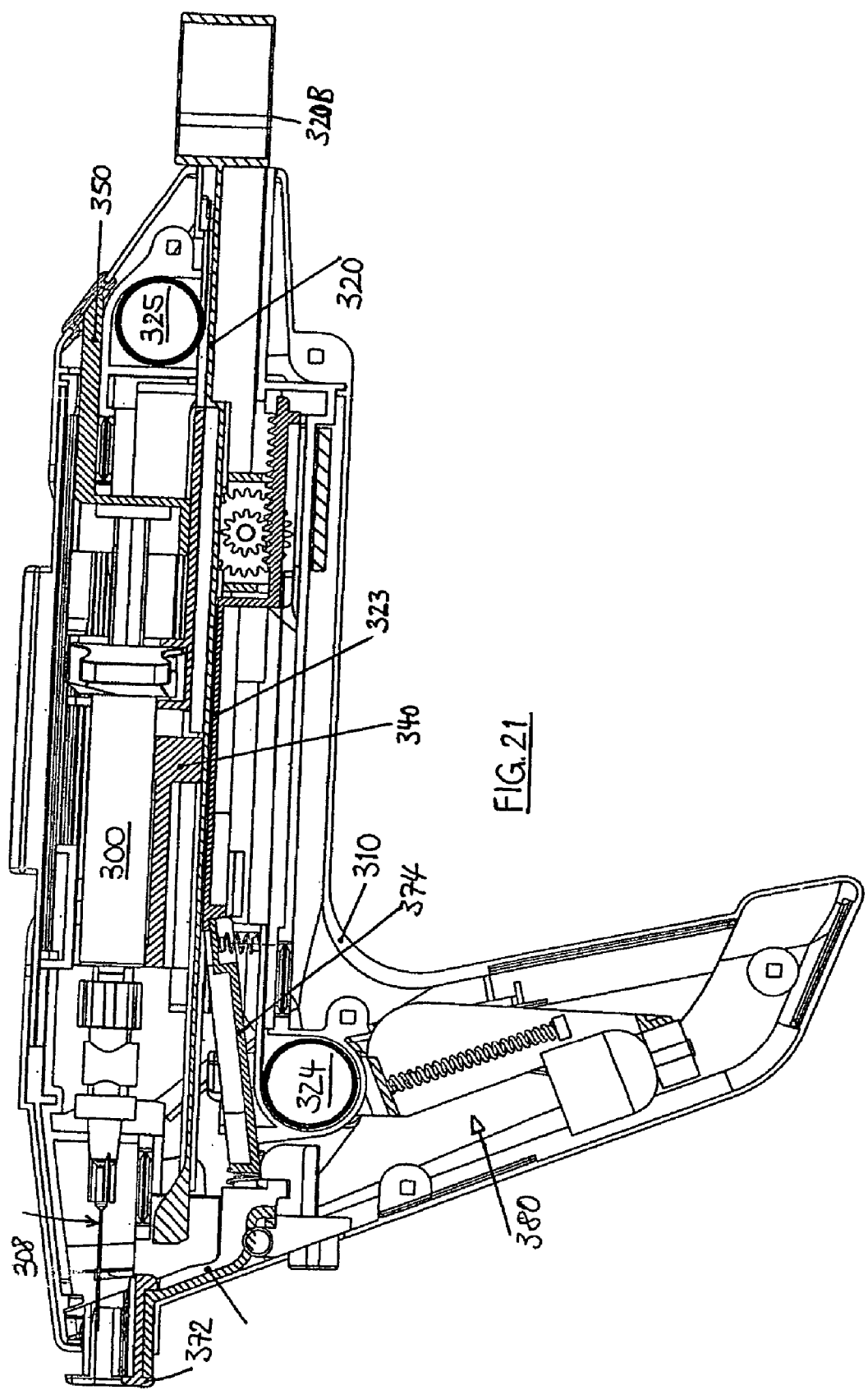
FIG. 21 shows a third illustrative embodiment in a longitudinal section with inserted syringe.

An overall view of the third illustrative embodiment is shown in FIG. 21.

The component groups of the third illustrative embodiment will now first be described in brief:

At its front end (injection end), the housing 310 has a downwardly directed grip which permits easy handling and in which a bell ring mechanism (FIG. 32) can also be accommodated to give an acoustic indication of the end of the fully automatic strokes H1, H2, H3.

Instead of the push rods 120, 220 present in the two illustrative embodiments described above, the main actuating element here is a pull-out loading bar 320 by means of which an advancer spring 324 is pretensioned, the latter serving for the advance movement and return movement of the injection carriage.

The advancer spring 324 is released by control elements, for example by a trigger lever 326.

Figure 22:
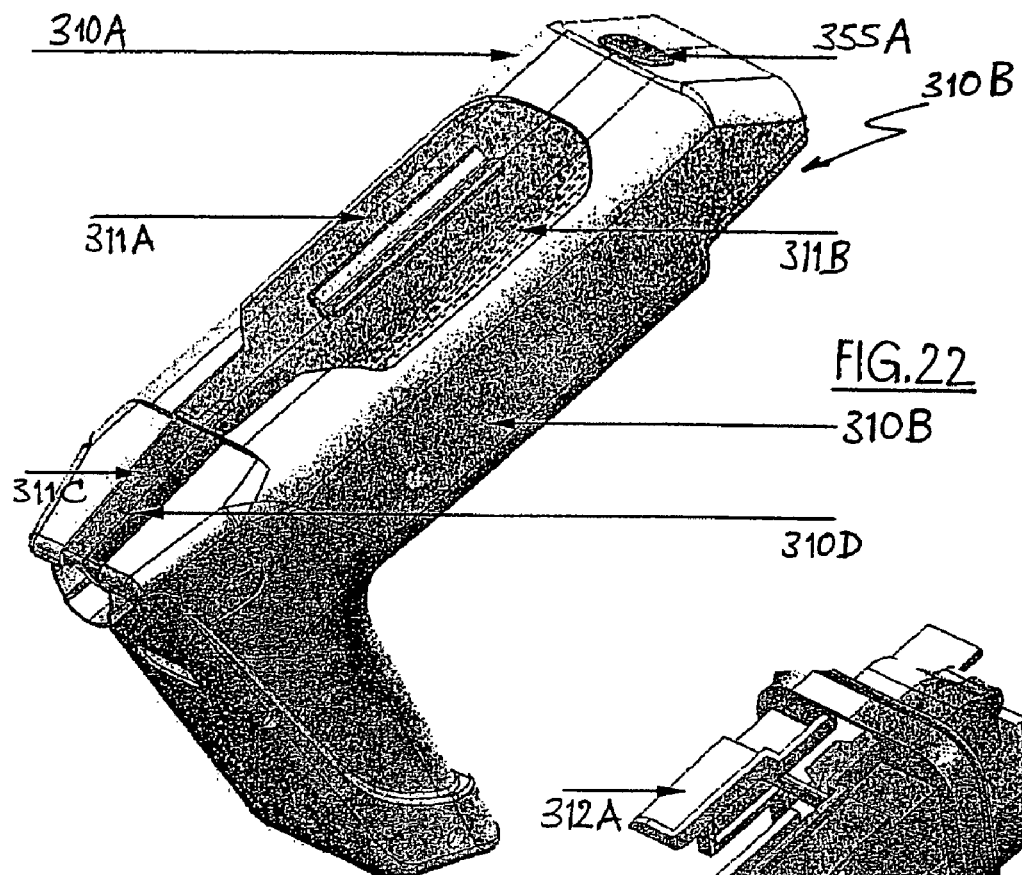
FIG. 22 shows an overall view of the injection device according to FIG. 21.
Figure 23:
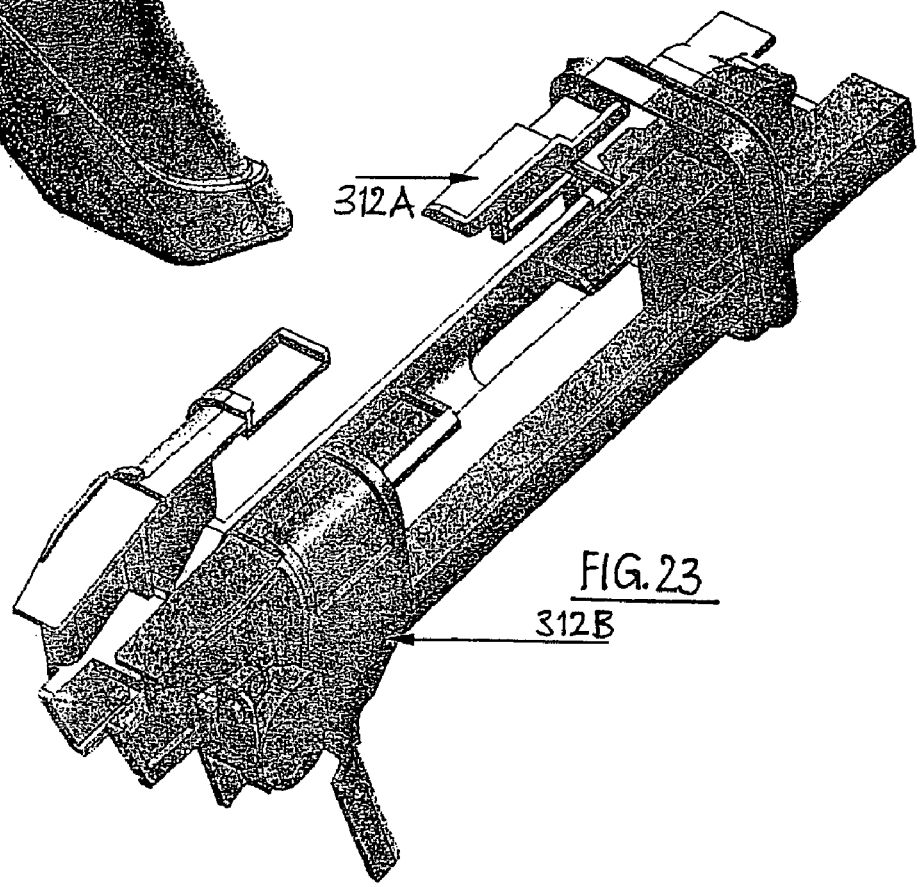
FIG. 23 shows a perspective view of the two halves of the receiving frame.

The structure of the housing 310 is shown in FIGS. 22 and 23. The housing 310 itself is made in two parts, with two housing shells 310A, 310B and a two-part cover 311A, 311B over the syringe 300, which cover can be opened after completion of the injection, and with an opening for a signal face 355A for indicating the loading state.

Held inside the housing 310, there is a likewise two-part receiving frame 312 with two symmetrical halves 312A, 312B, in which receiving frame 312 the movable operating components are axially displaceable and in which the actuating elements are also received.

Figure 24:
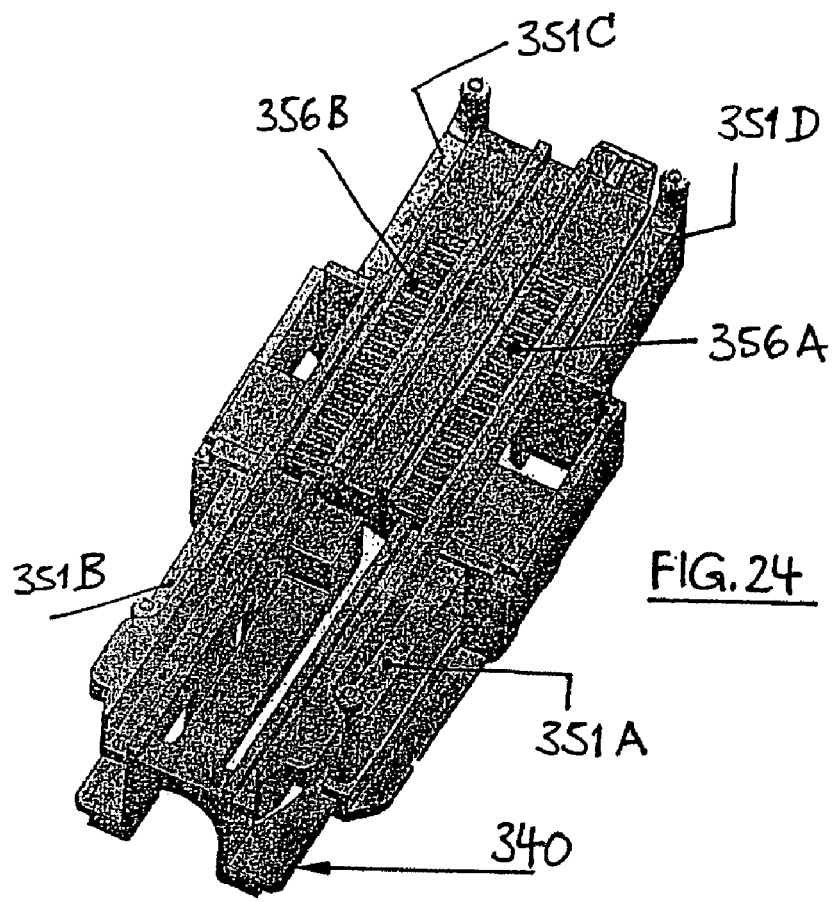
FIG. 24 shows a first perspective view of the syringe holder and ram.
Figure 25:
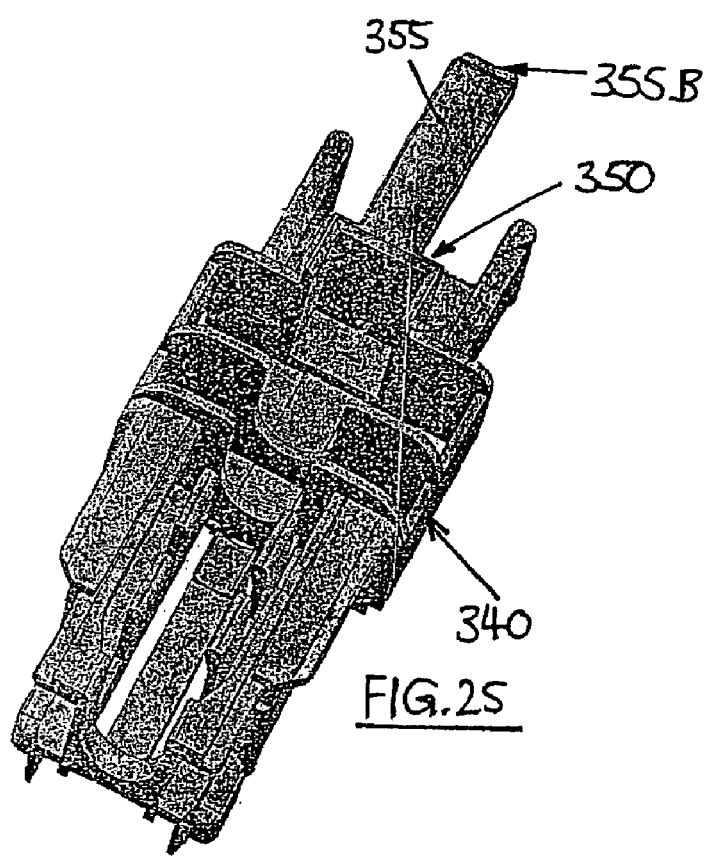
FIG. 25 shows a second perspective view of the syringe holder and ram.

FIGS. 24 and 25 show the injection carriage, consisting of syringe holder 340 and ram 350; the latter has a rearward extension piece 355 whose end face 355B forms the above-mentioned signal face 355A of the housing 310.

The ram 350 has lateral locking arms 351A, 351B for the syringe advance. As in all of the illustrative embodiments, the syringe holder 340 and the ram 350 can be displaced one inside the other, such that the ram 350 can perform the injection stroke H2. On the underside of the ram 350, two sets of teeth 356A, 356B can be seen which are used for advancing the ram 350 relative to the syringe holder 340.

Figure 26:
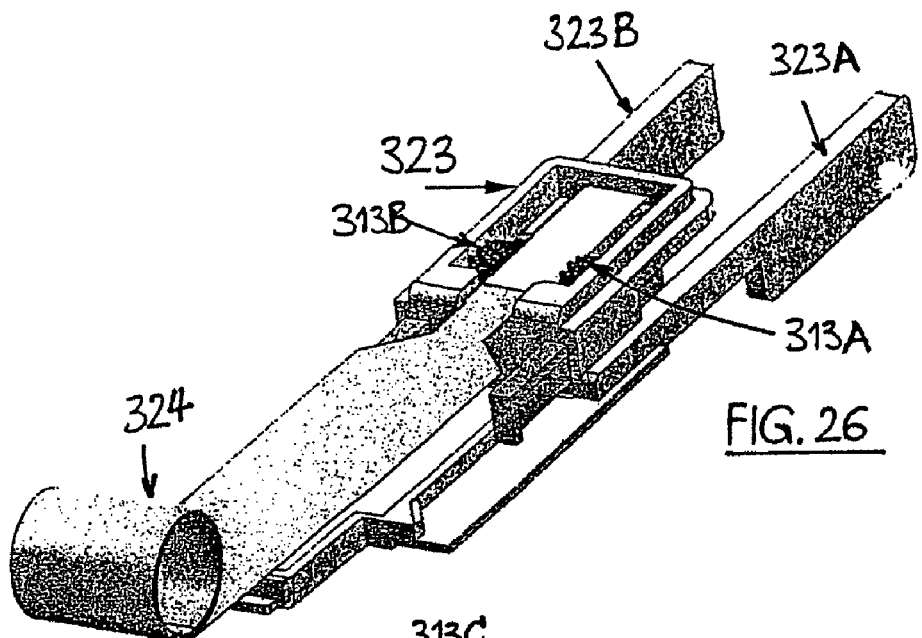
FIG. 26 shows a first perspective view of the advancer carriage.
Figure 28:
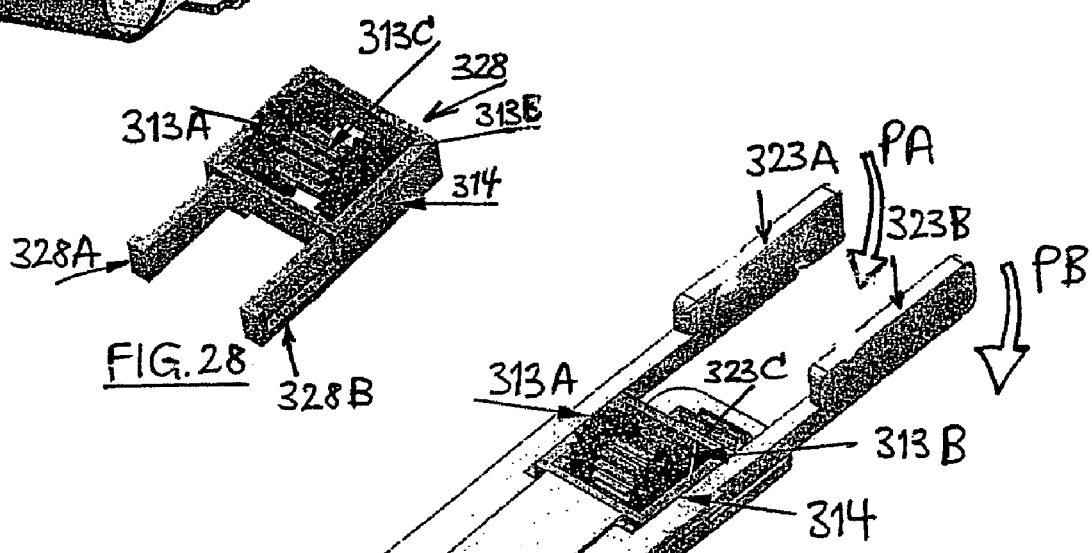
FIG. 28 shows a perspective view of the toothed wheel carriage.
Figure 27:
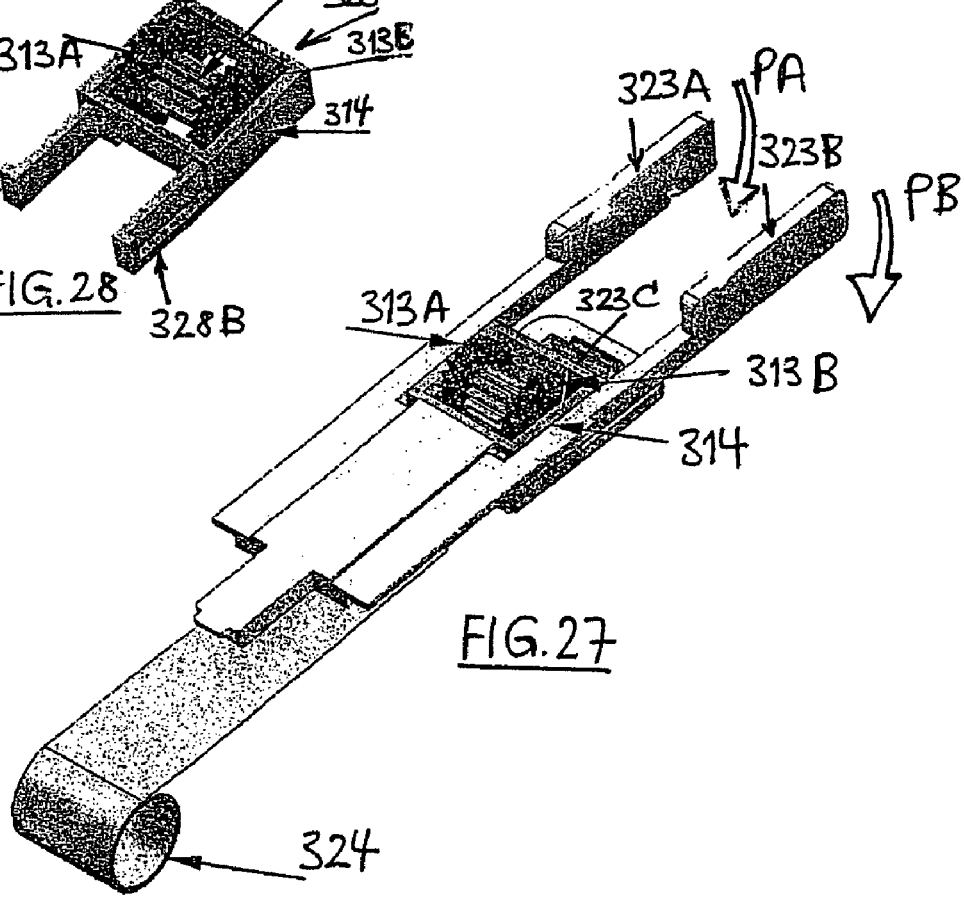
FIG. 27 shows a second perspective view of the advancer carriage.

FIGS. 26-28 show, in a plan view (FIG. 26) and bottom view (FIG. 27), a further component of the actuating element, the advancer carriage 323, with a toothed wheel gearing 328 which is arranged in a housing 314 and whose double toothed wheels 313A, 313B engage in the teeth 356A, 356B of the ram 350 and whose central toothed wheel 313C interacts with teeth 323 of an advancer carriage 323. At one end, the advancer carriage 323 has two laterally protruding locking arms 323A, 323B which are elastic to the extent that they are able to pivot downward in the direction of the arrows PA, PB. Arranged at the other end, as the advancer spring 324, there is a scroll spring which acts in the longitudinal direction on the advancer carriage 323. The toothed wheel gearing 328 also has lateral abutment rods 328A, 328B pointing in the direction of the advancer spring 324.

Figure 29:
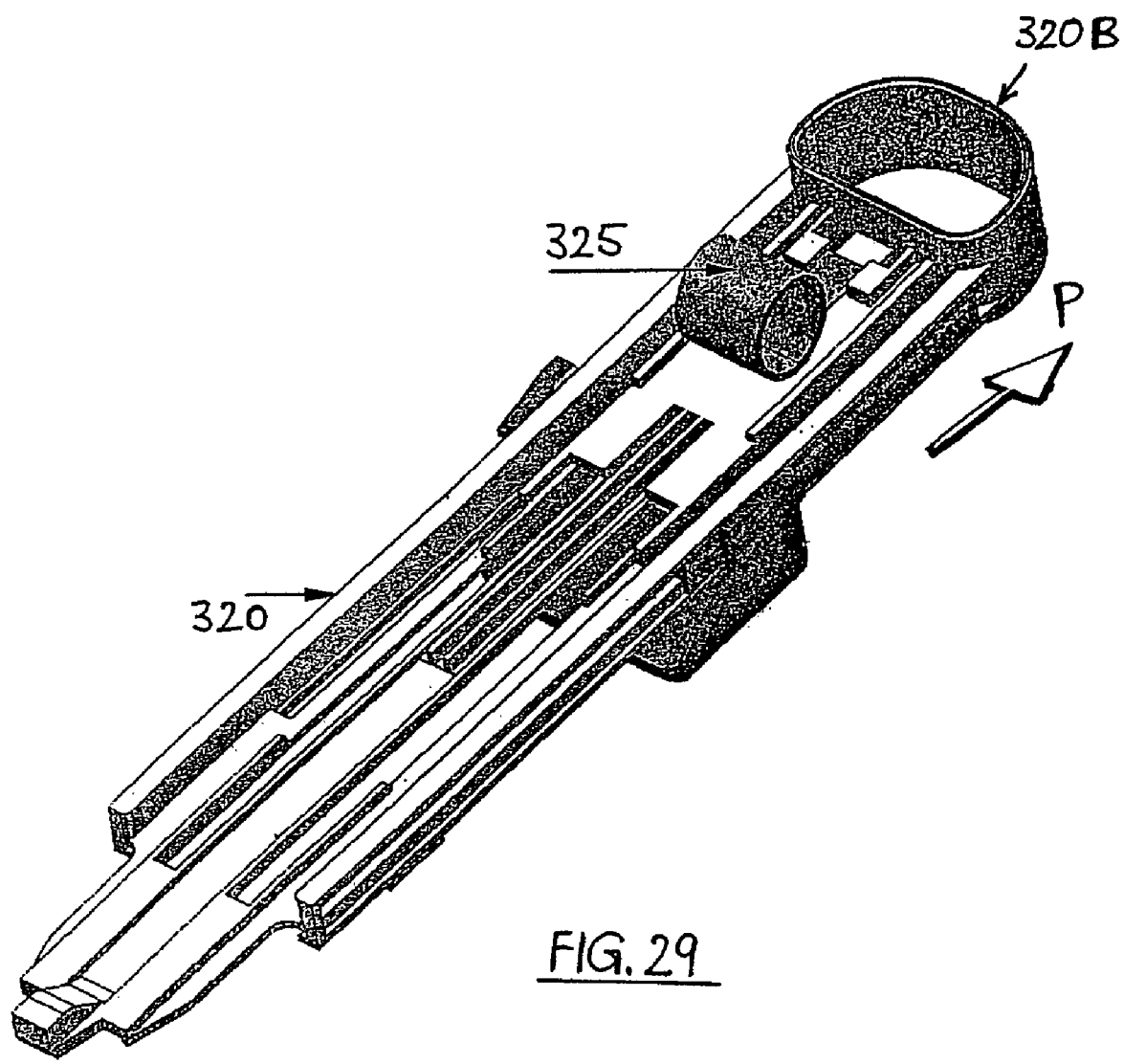
FIG. 29 shows a perspective view of the pull-out loading bar with scroll spring.

FIG. 29 shows a further essential component of the actuating element, the pull-out loading bar 320, with a restoring spring 325 and with a grip 320B protruding out from the housing 310. By pulling the pull-out loading bar 320 in the direction of the arrow P counter to the force of the advancer spring 324, the injection carriage (syringe holder 340 and ram 350) is brought into its starting position and tensioned. The now likewise tensioned restoring spring 325 returns the pull-out loading bar 320 automatically to its starting position when the grip 320B is released. By actuation of a trigger mechanism 370, the stored energy of the advancer spring 324 is delivered to syringe holder 340 and ram 350.

Figure 30:
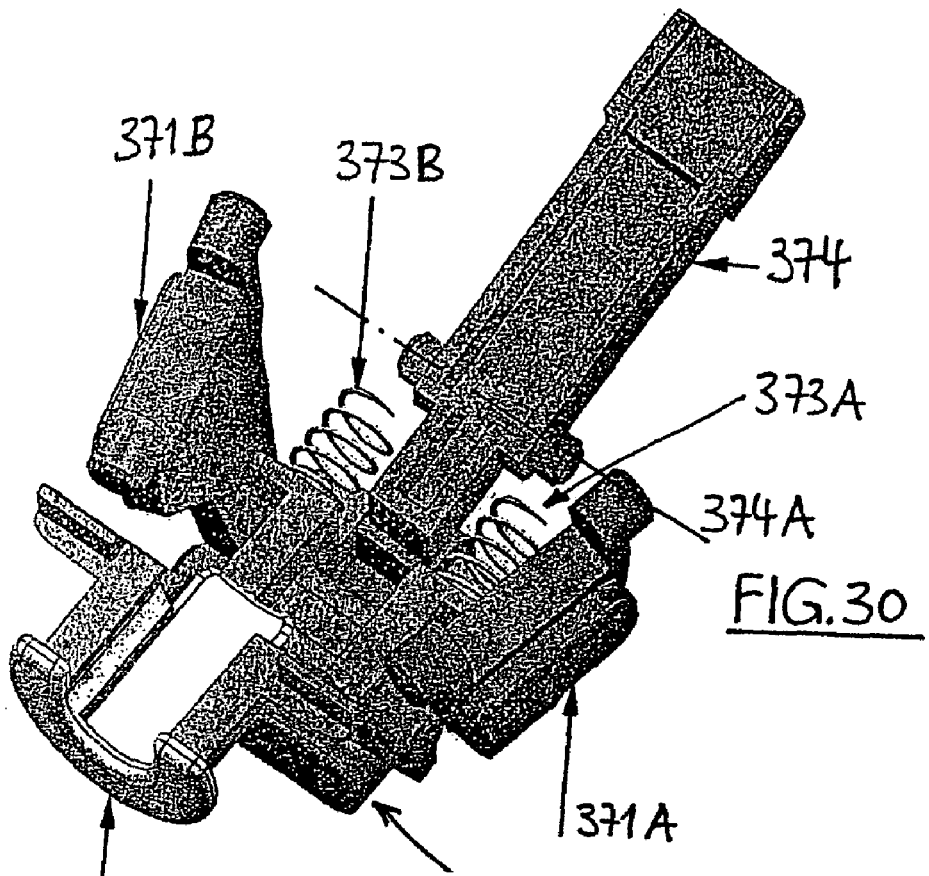
FIG. 30 shows a first perspective view of the loading mechanism.
Figure 31:
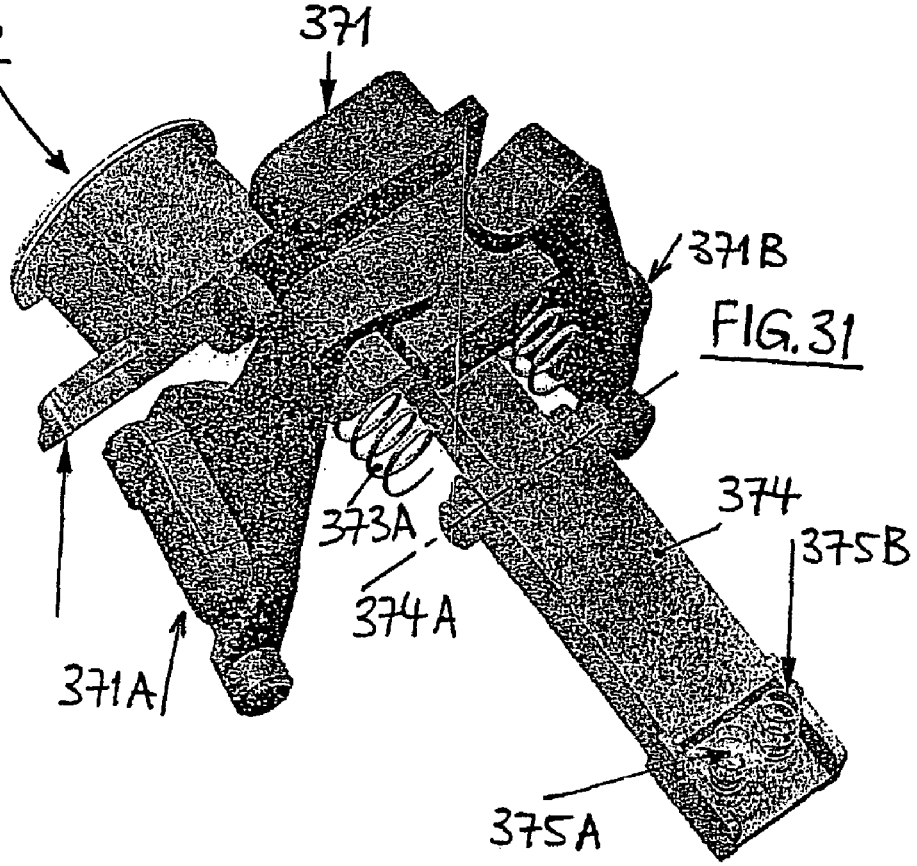
FIG. 31 shows a second perspective view of the loading mechanism.

FIGS. 30 and 31 show this trigger mechanism 370 of the injection device, which mechanism establishes a mechanical interaction with the components for freeing the advancer spring 324 in the loaded state. The trigger mechanism consists of a three-part switch, with a central switch element 371 and two lateral switch wings 371A, 371B, an annular safety cap 372 which surrounds the needle 380 and which is axially displaceable in the housing 310 counter to the force of two compression springs 373A, 373B. Only in its pressed position (not shown), upon application of the injection device to the skin, does the safety cap 372 permit, through release of the switch element 371 and of the switch wings 371A, 371B, actuation of a trigger pivot lever 374 pivotable about a shaft 374A against two compression springs 375A, 375B. When the switch element 371 is actuated, it pivots against one end of the trigger pivot lever 374, the other end of which is then pivoted away from the front end of the pretensioned advancer carriage 323, whereupon the insertion stroke H1 can start (FIG. 37B).

Figure 32:
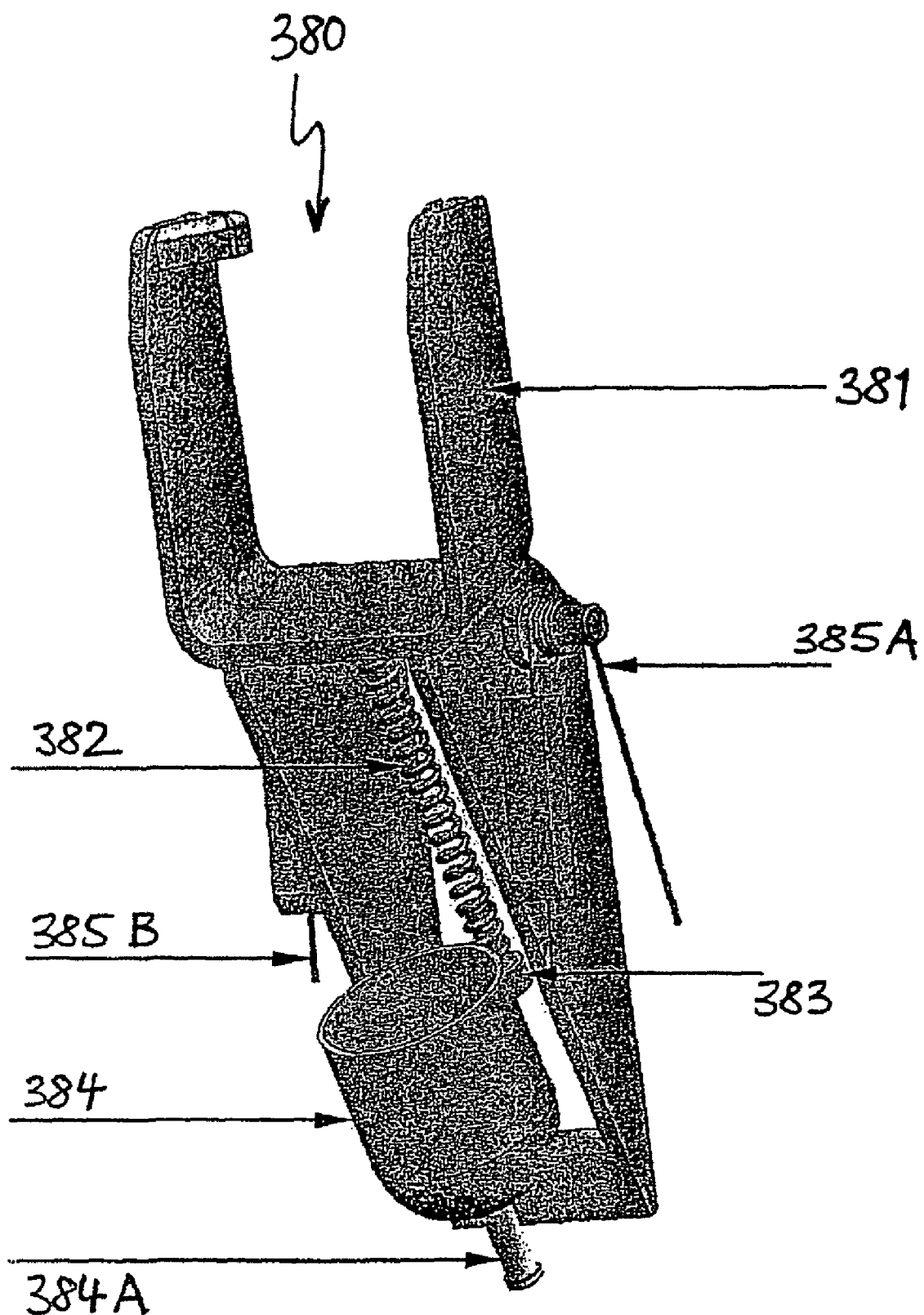
FIG. 32 shows a perspective view of the bell ring mechanism.

FIG. 32 shows the bell ring mechanism 380 whose bell ring lever 381 is pretensioned against springs 385A, 385B after completion of the return stroke H3 and, after triggering, a clapper 383 articulated on a compression spring 382 strikes against a bell 384 attached to a holding pin 384A.

Figure 36A:
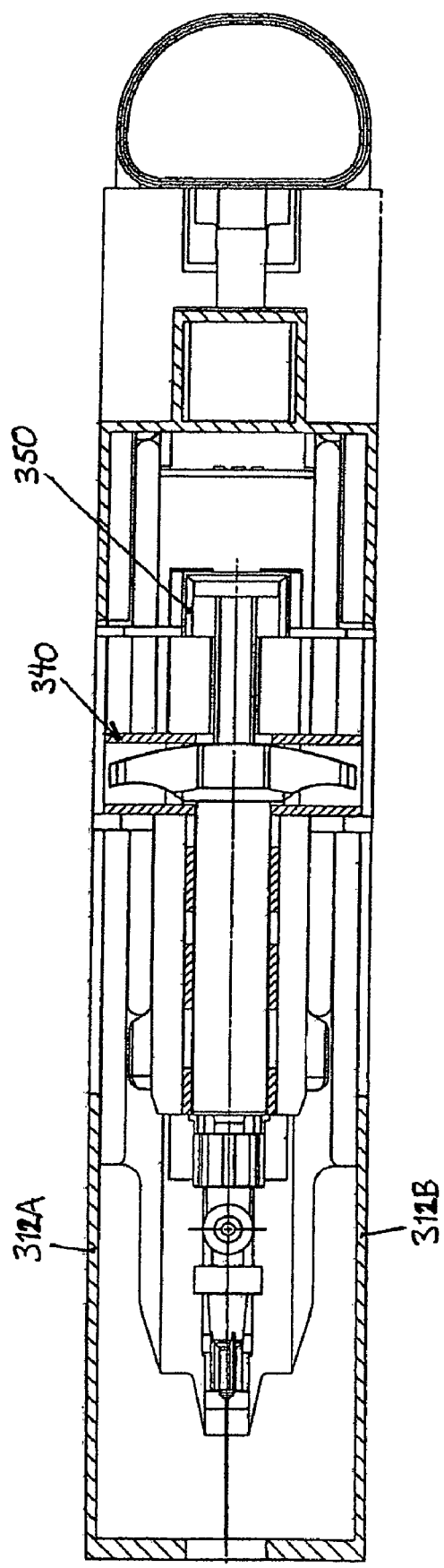
FIG. 36A shows a first longitudinal section through the operating components according to FIG. 36.
Figure 36C:
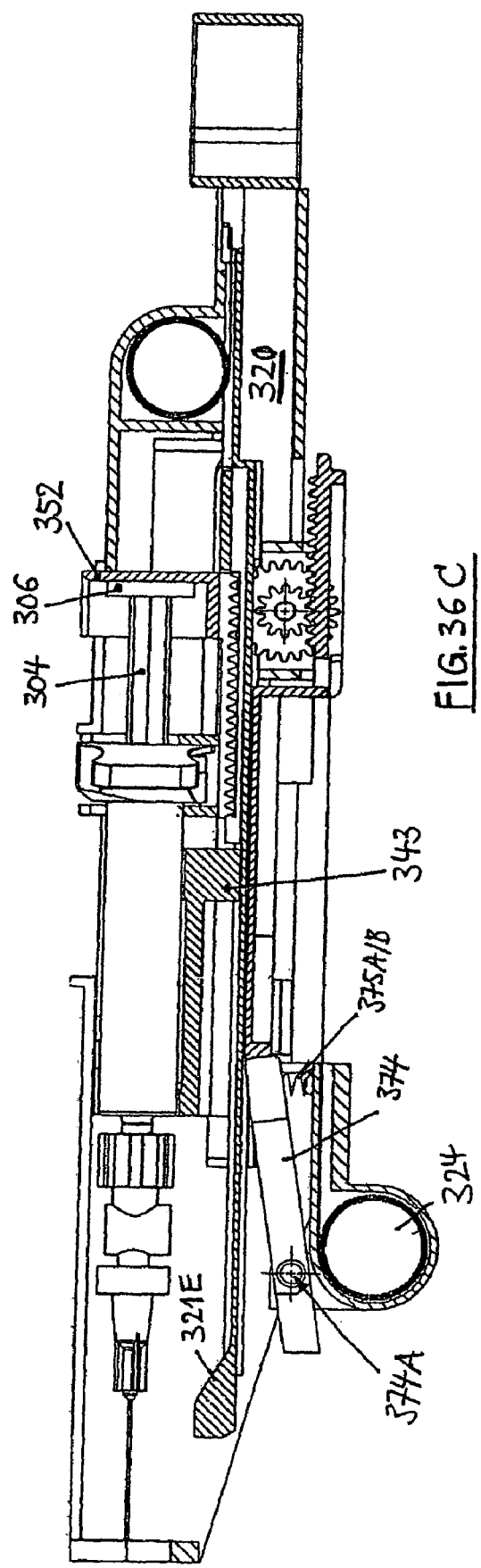
FIG. 36C shows a third longitudinal section through the operating components according to FIG. 36.
Figure 37:
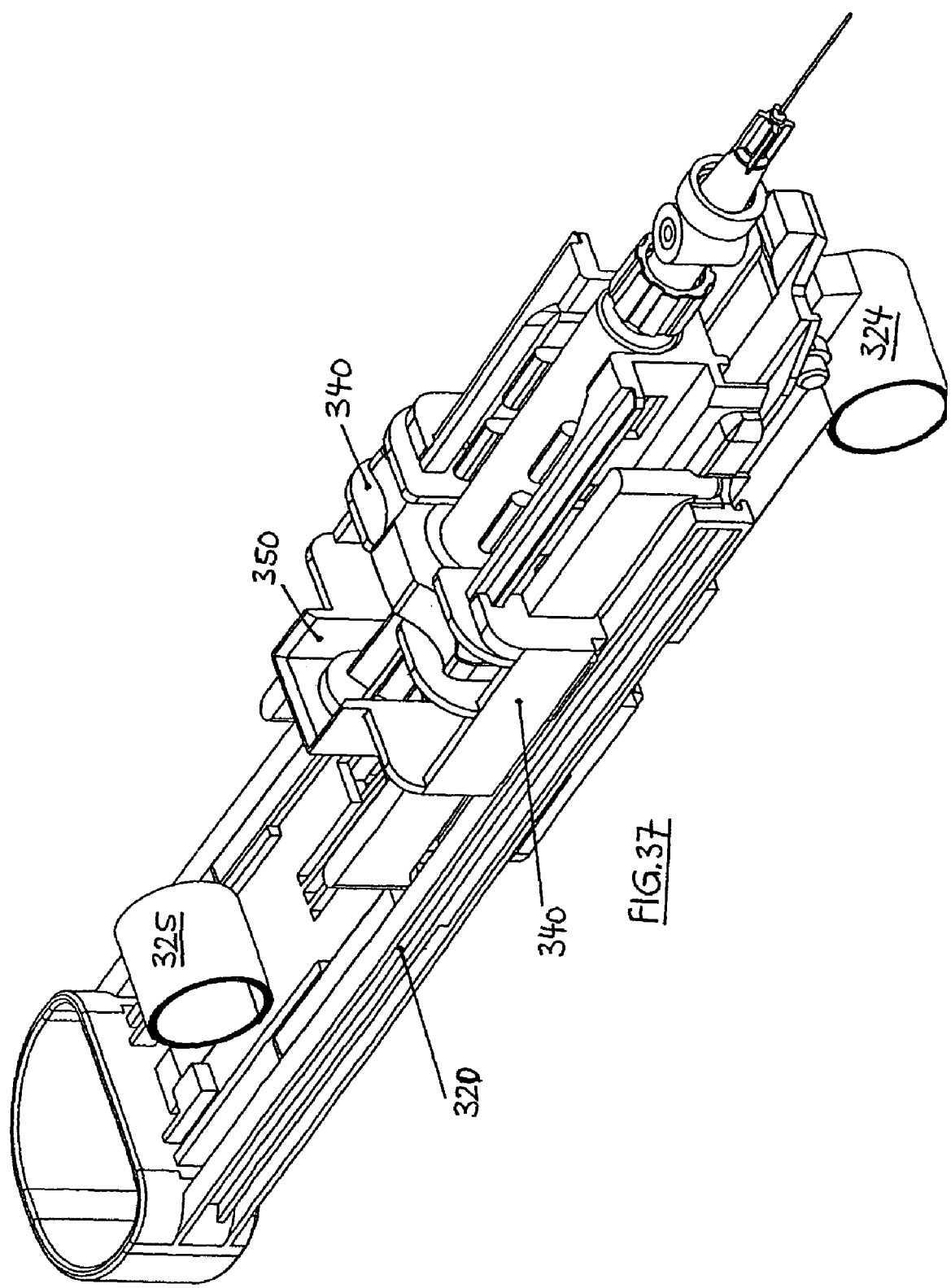
FIG. 37 shows a perspective partial view of essential operating components during the insertion stroke.
Figure 37A:
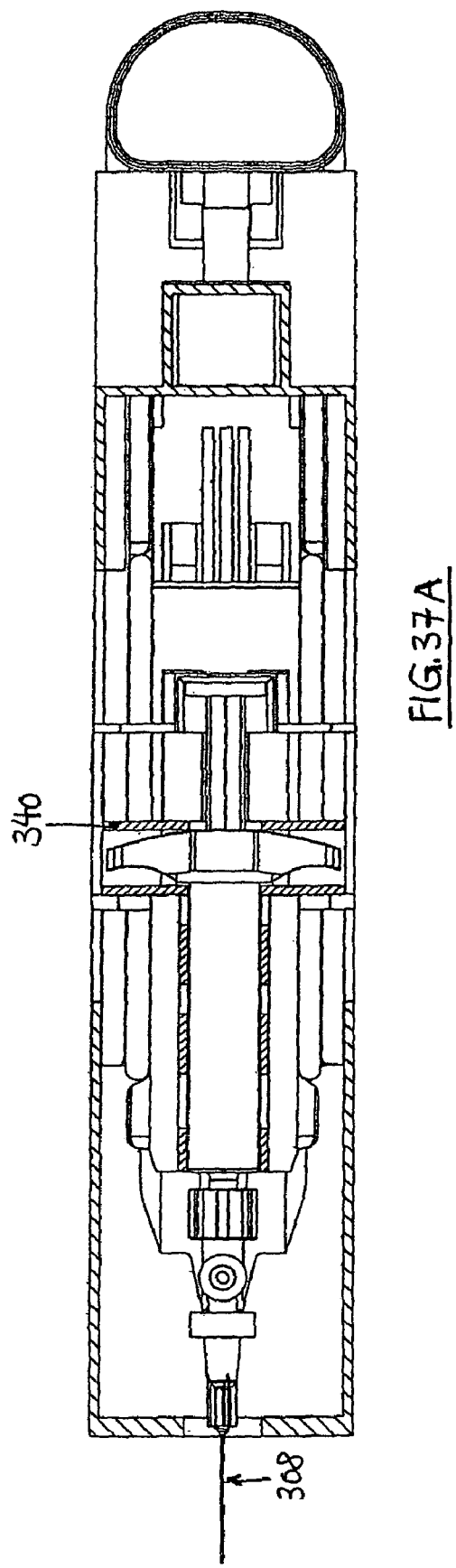
FIG. 37A shows a first longitudinal section through the operating components in their position according to FIG. 37.
Figure 37B:
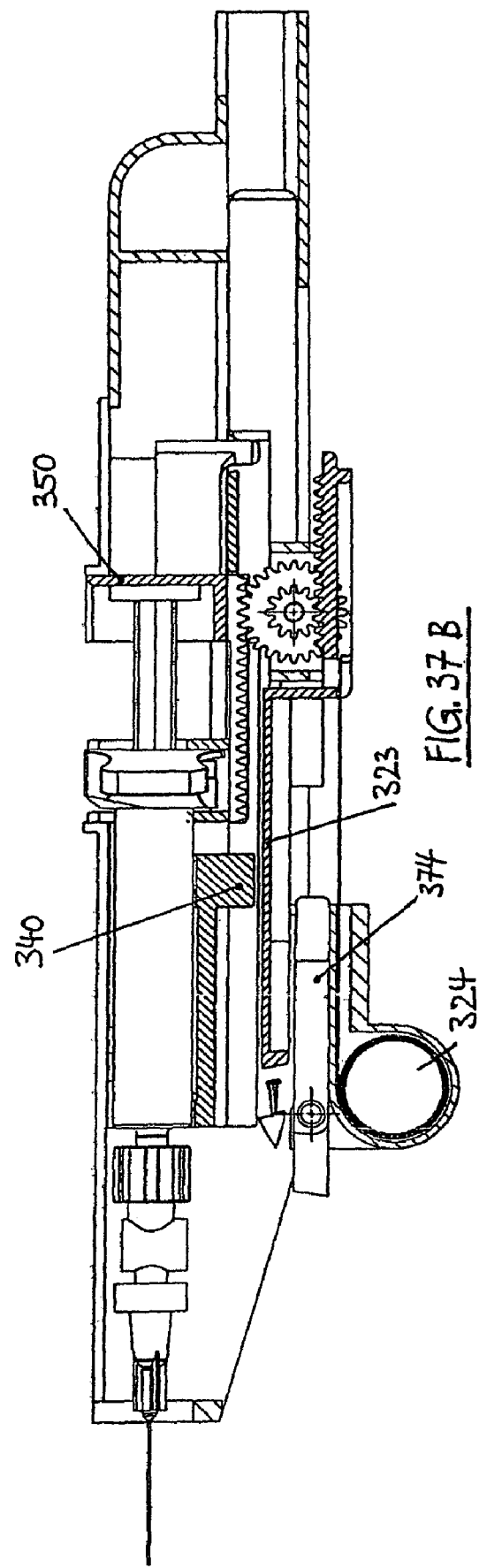
FIG. 37B shows a second longitudinal section through the operating components in their position according to FIG. 37.
Figure 37C:
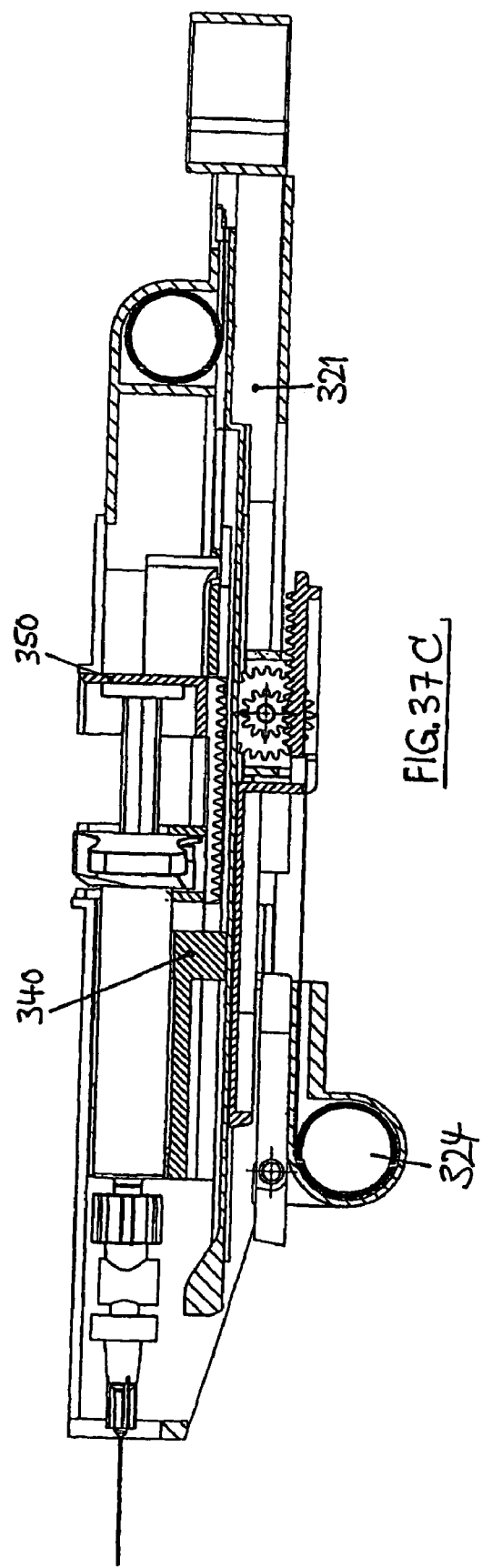
FIG. 37C shows a third longitudinal section through the operating components in their position according to FIG. 37.
Figure 38:
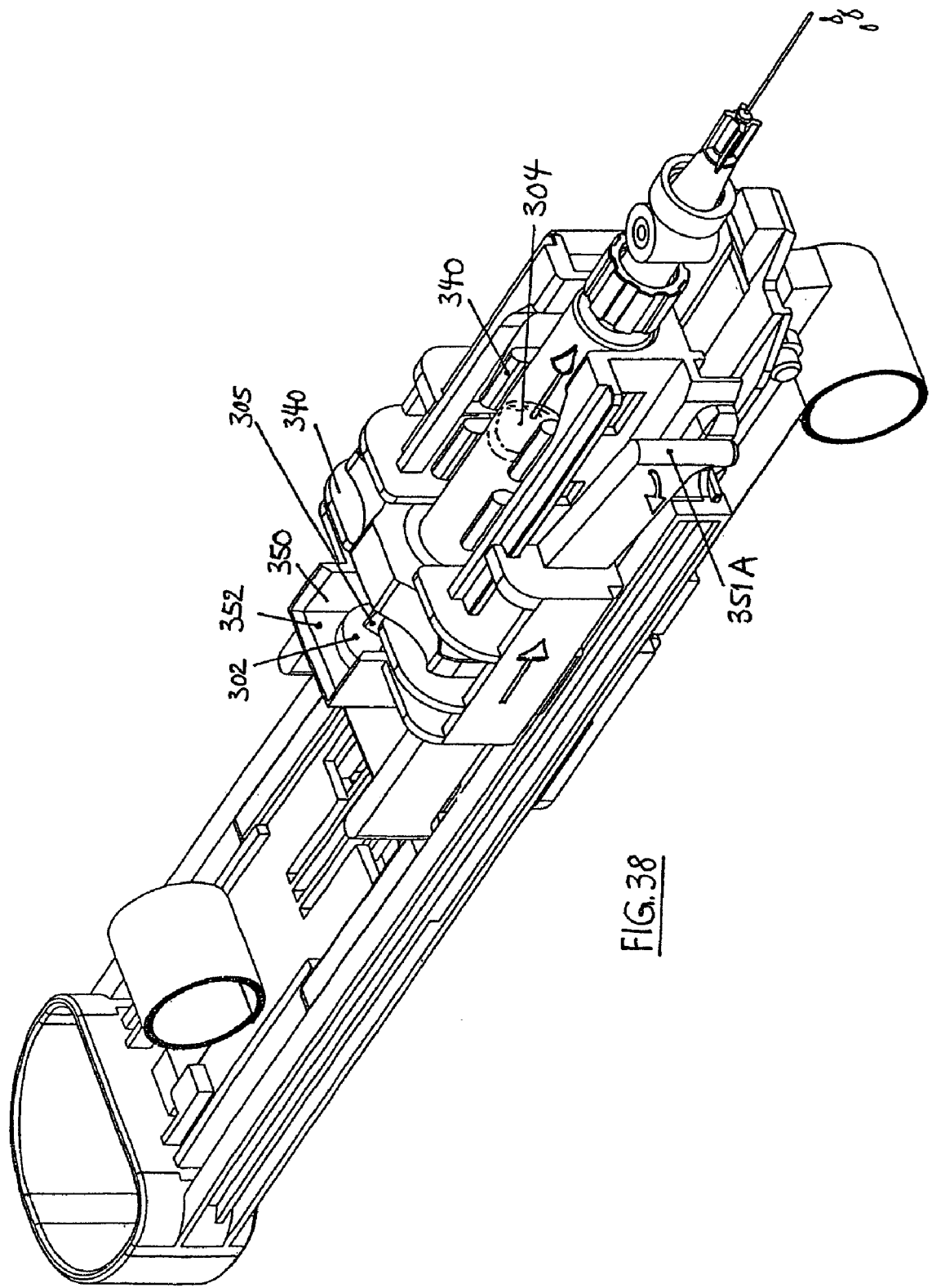
FIG. 38 shows a perspective partial view of essential operating components during the insertion stroke.
Figure 38A:
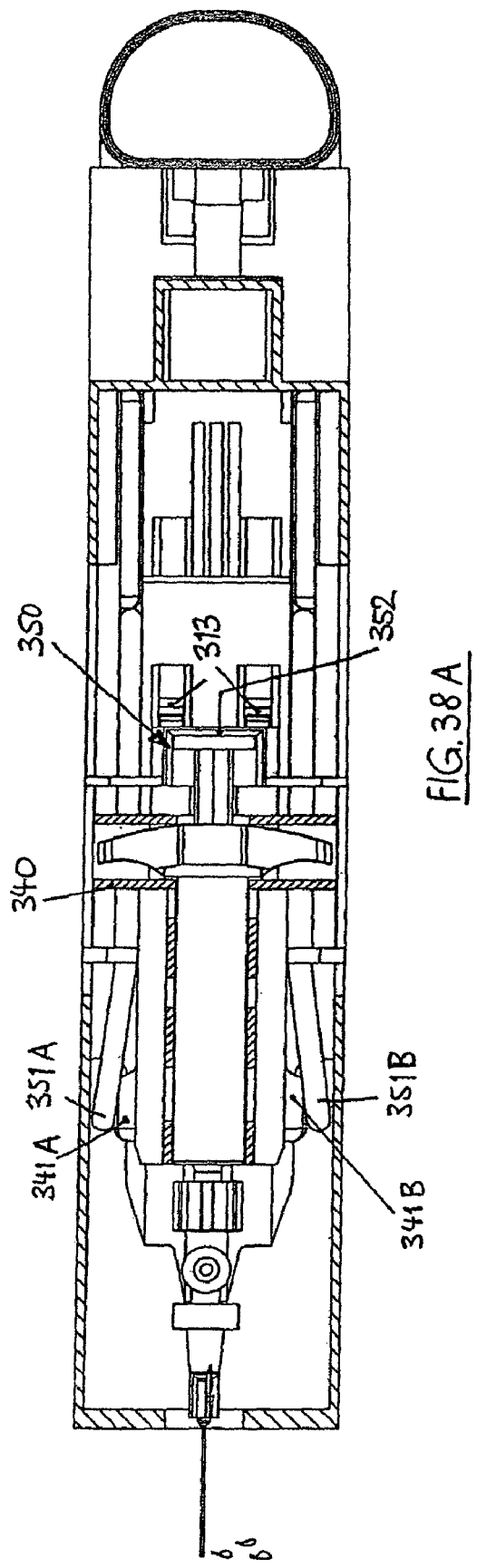
FIG. 38A shows a first longitudinal section through the operating components in their position according to FIG. 38.
Figure 38B:
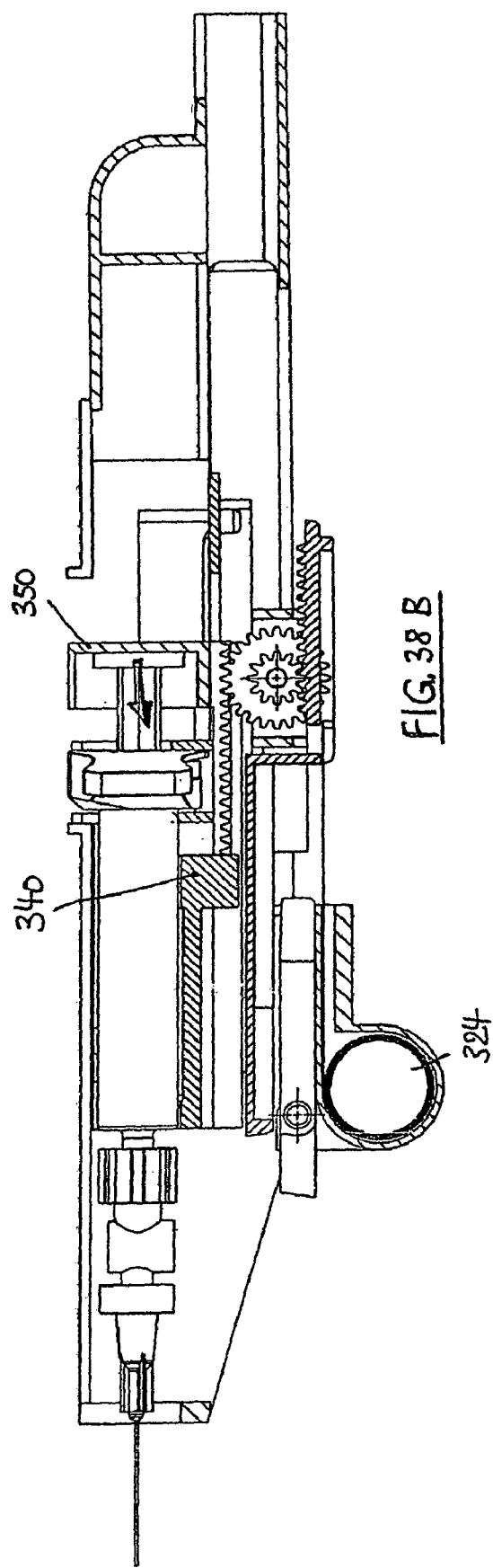
FIG. 38B shows a second longitudinal section through the operating components in their position according to FIG. 38.
Figure 38C:
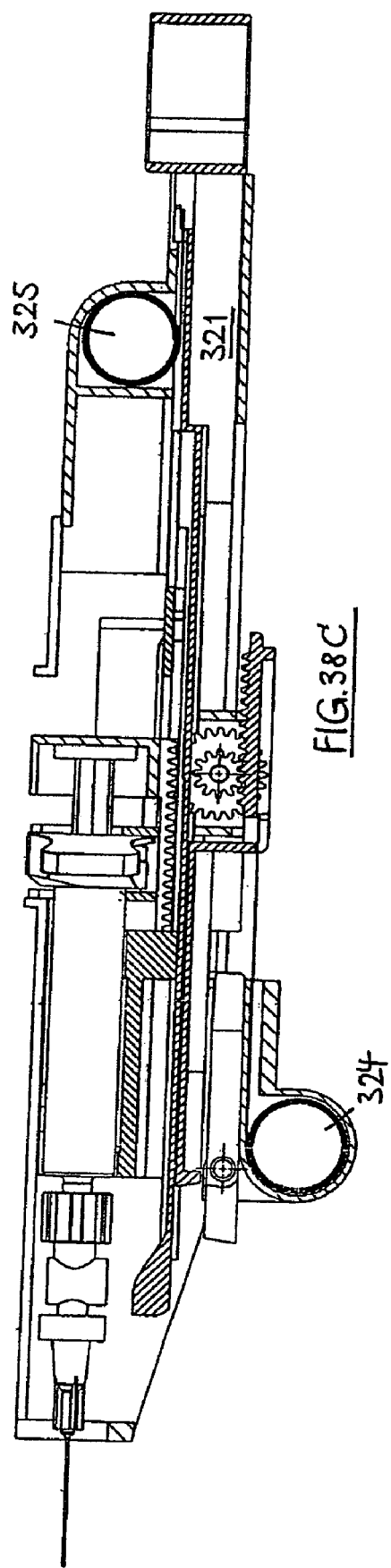
FIG. 38C shows a third longitudinal section through the operating components in their position according to FIG. 38.
Figure 39:
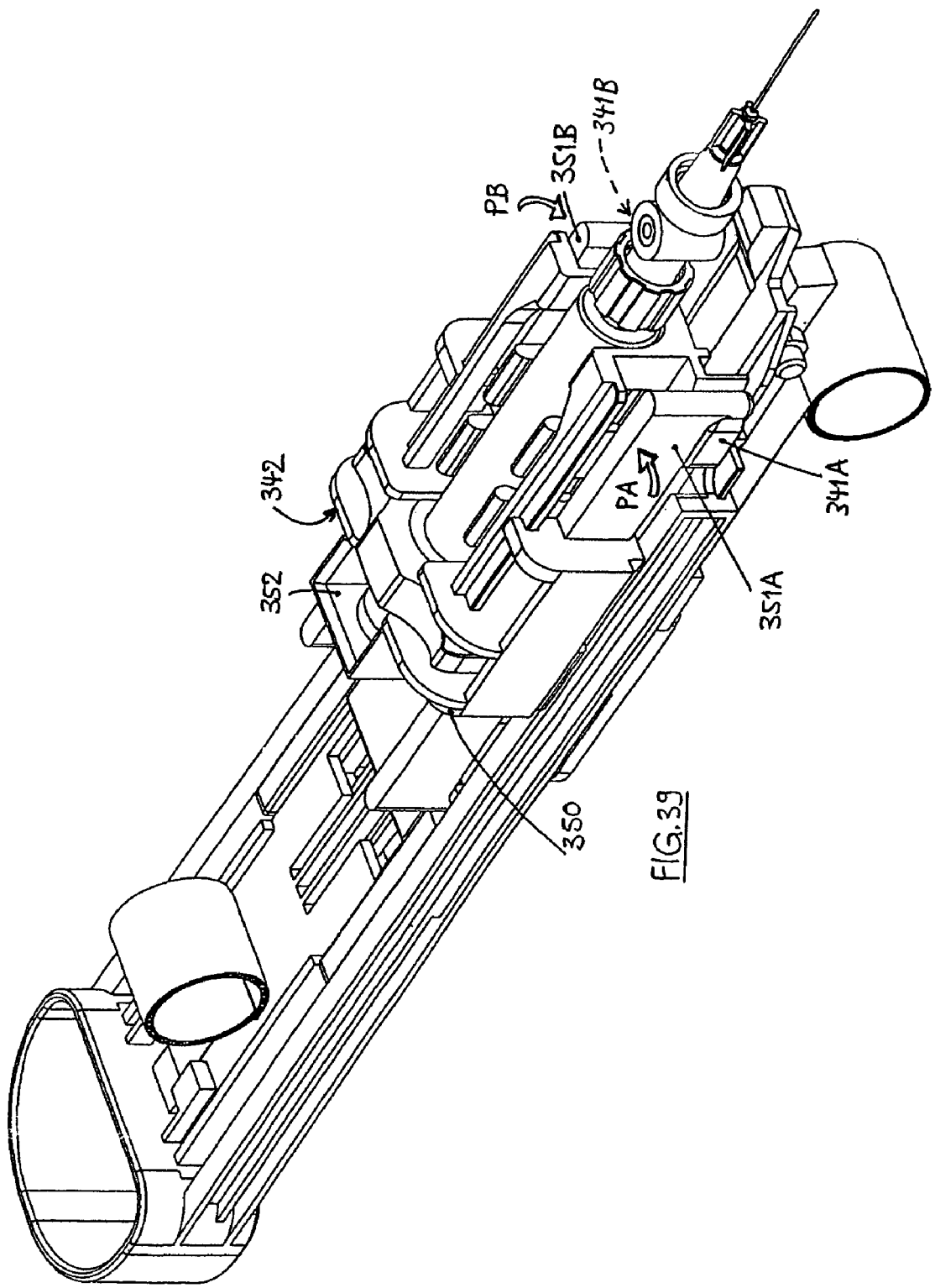
FIG. 39 shows a perspective partial view of essential operating components after completion of the injection stroke.
Figure 40:
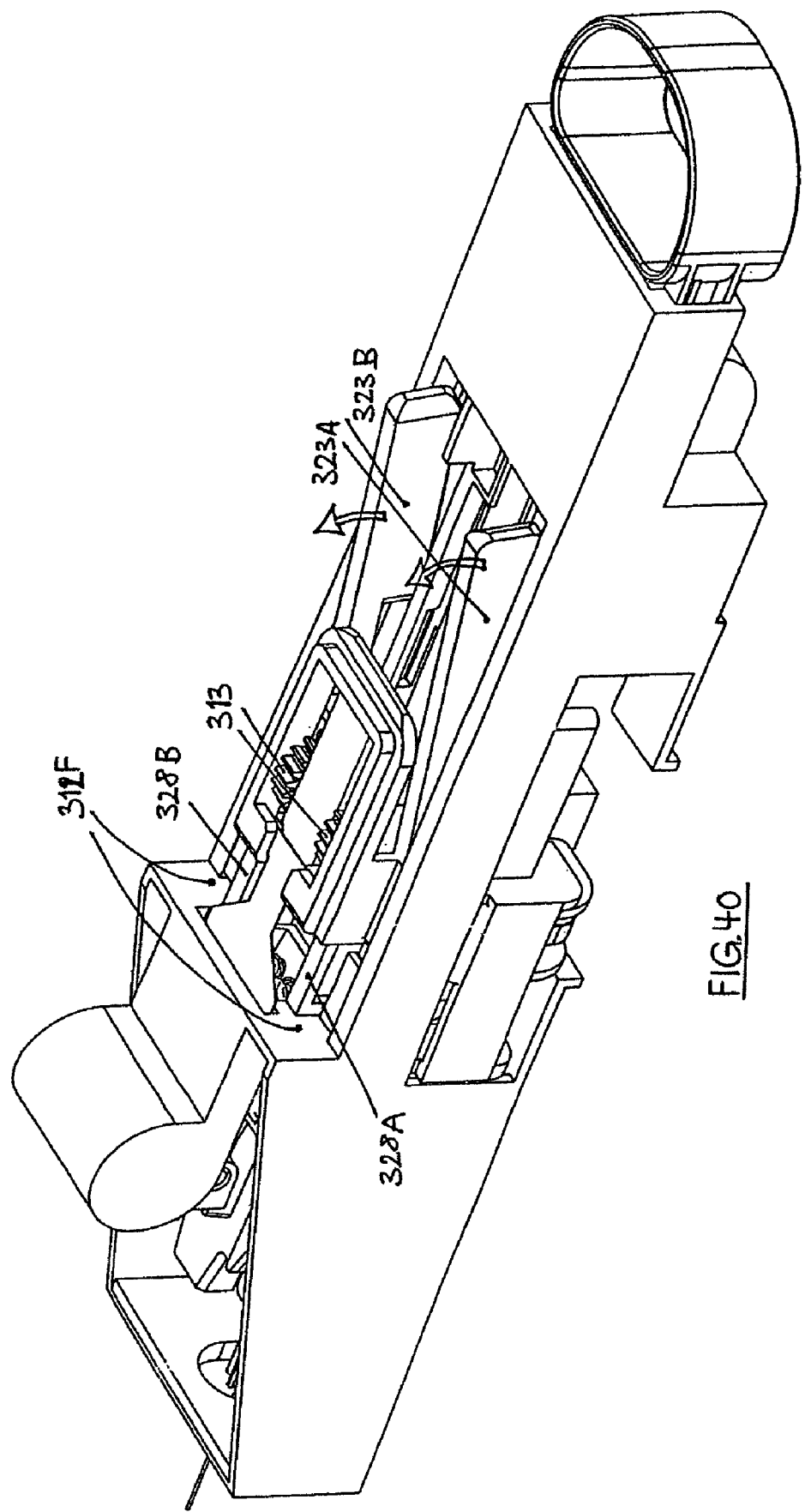
FIG. 40 shows a perspective partial view of essential operating components before the start of the return stroke.
Figure 41A:
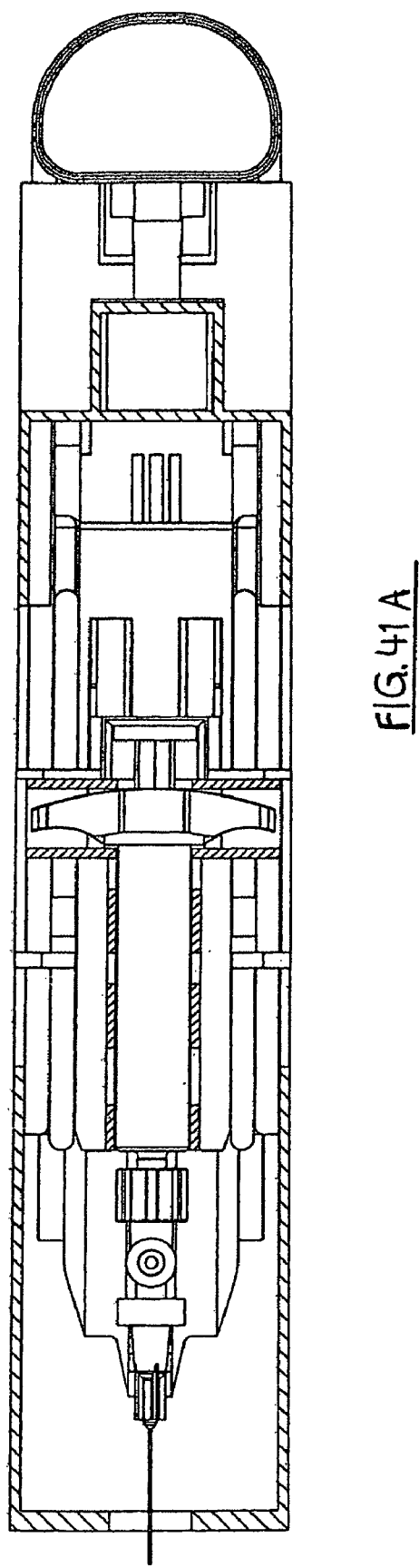
FIG. 41A shows a first longitudinal section through the operating components in their position according to FIG. 41.
Figure 41B:
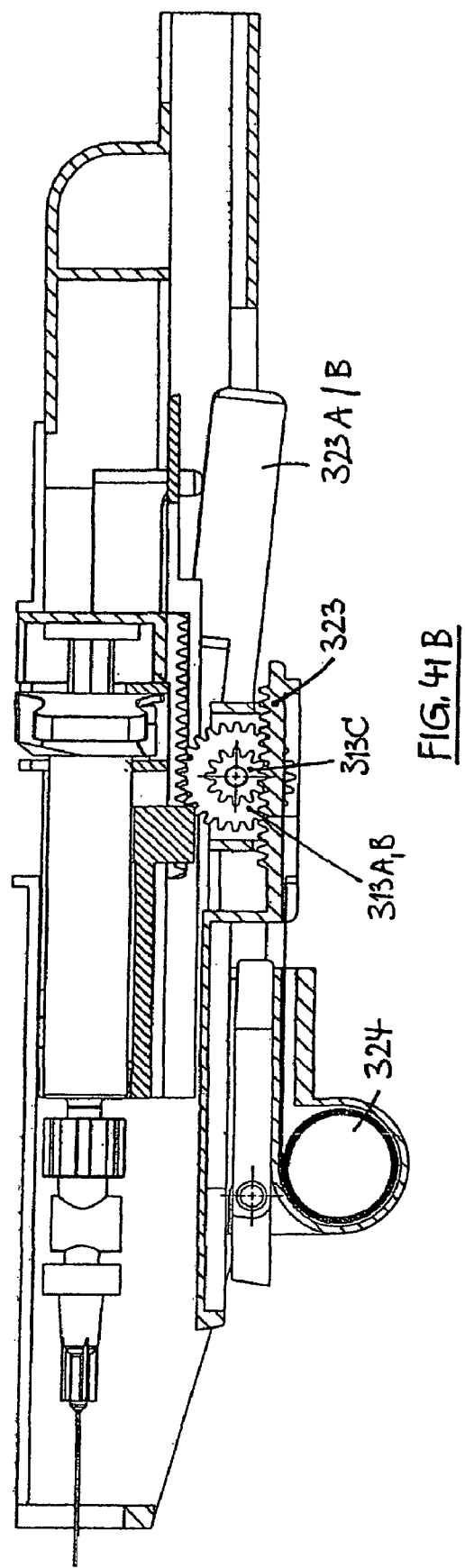
FIG. 41B shows a second longitudinal section through the operating components in their position according to FIG. 41.
Figure 41C:
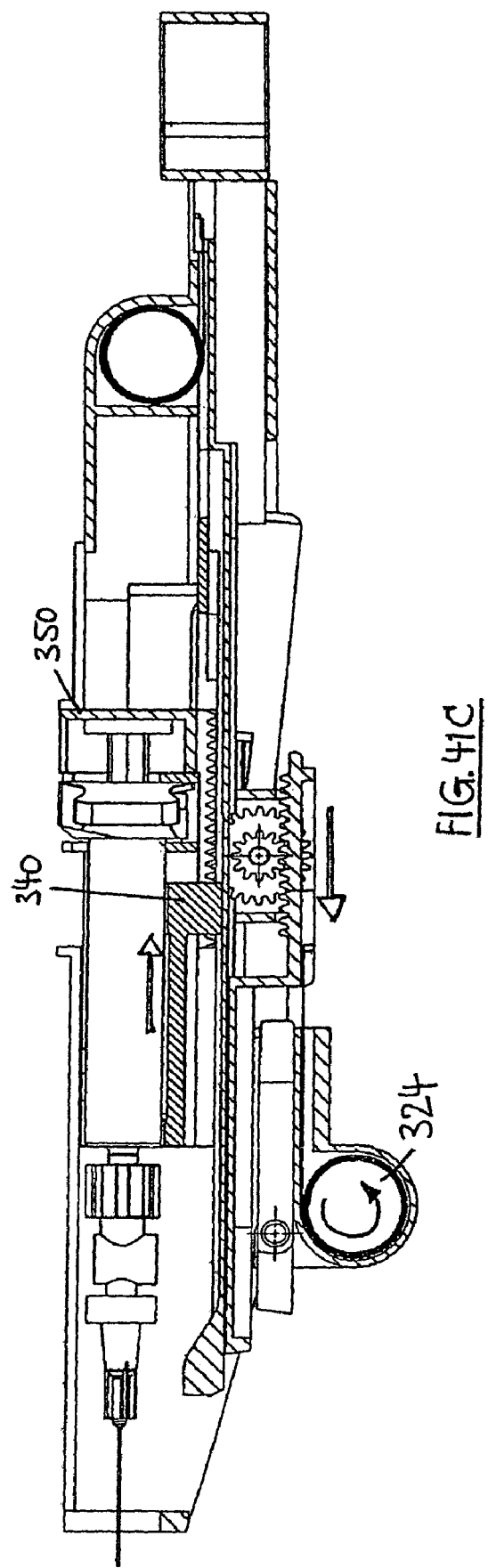
FIG. 41C shows a third longitudinal section through the operating components in their position according to FIG. 41.
Figure 42:
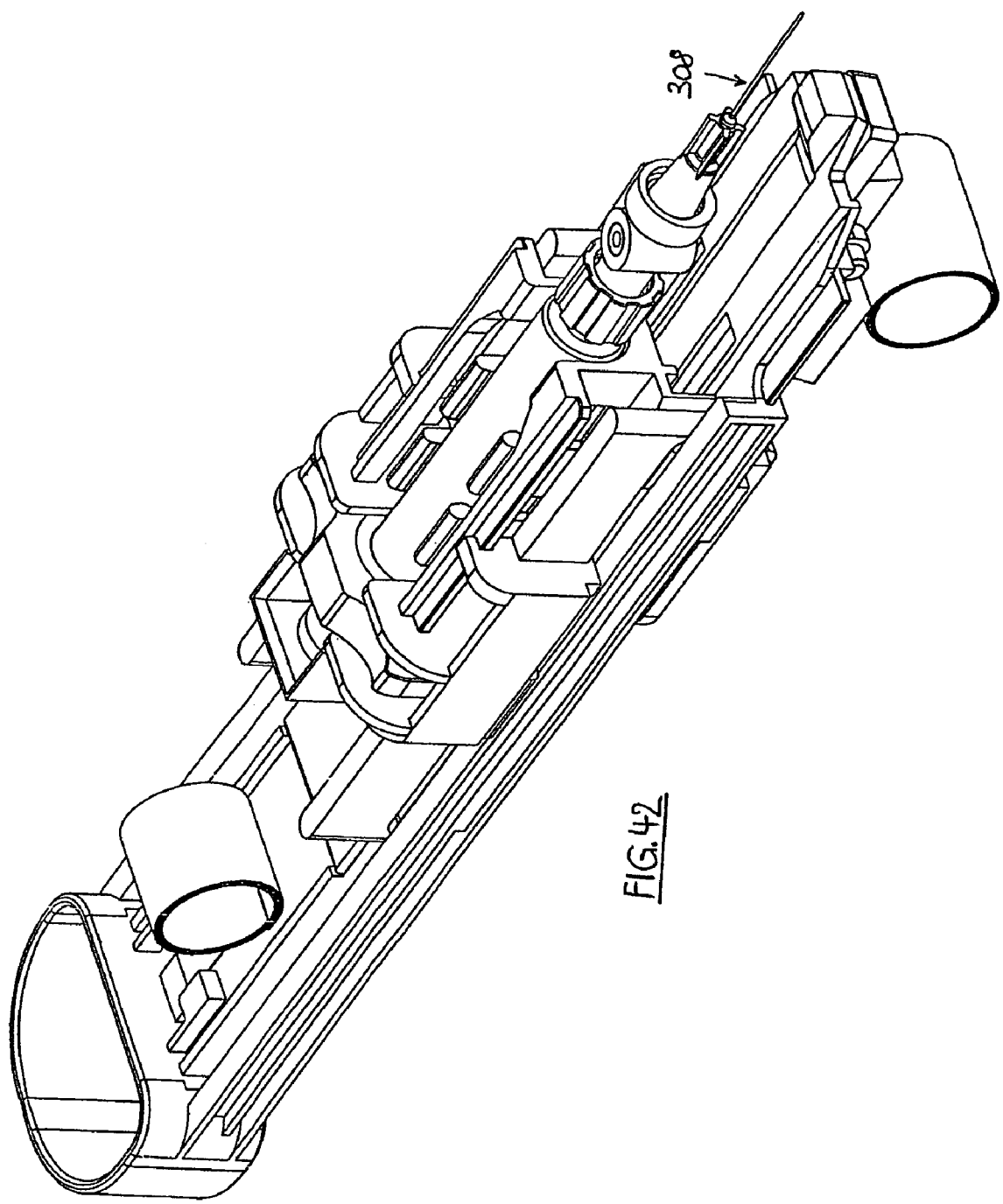
FIG. 42 shows a perspective partial view of essential operating components after completion of the return stroke.
Figure 42A:
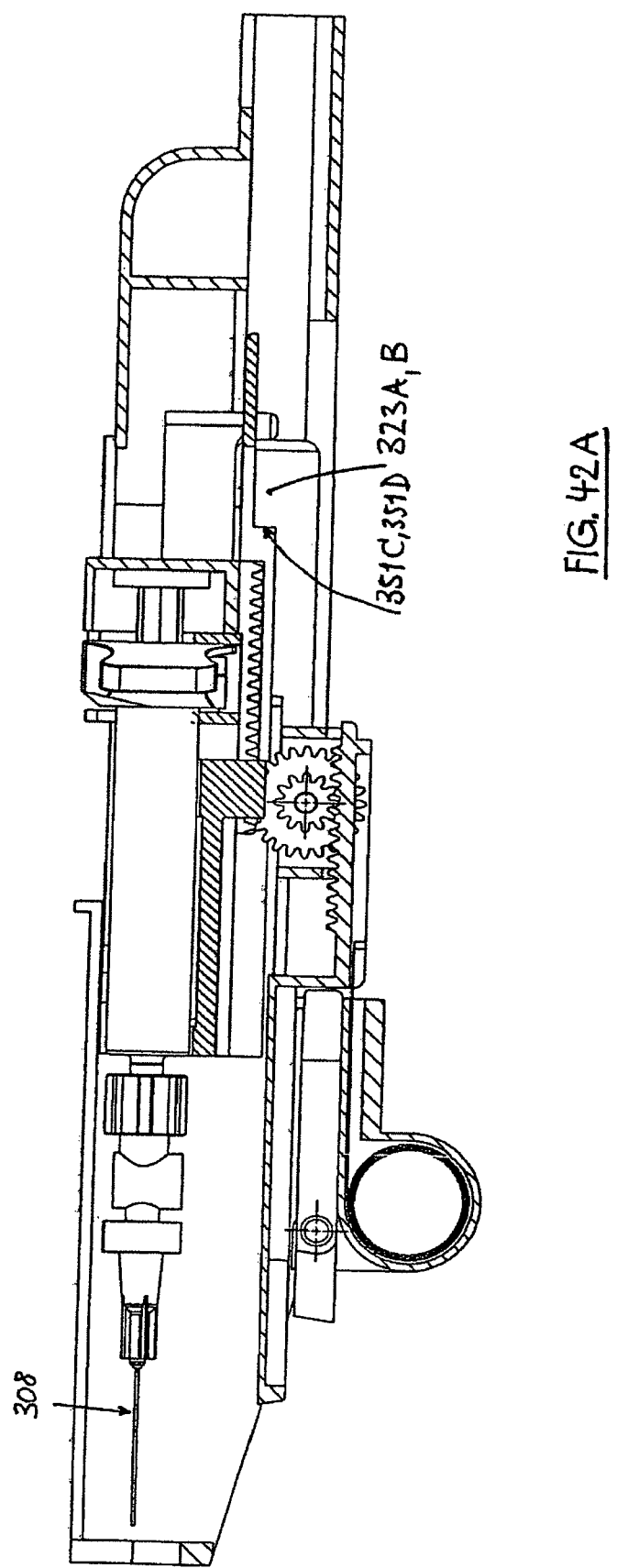
FIG. 42A shows a first longitudinal section through the operating components in their position according to FIG. 42.
Figure 42B:
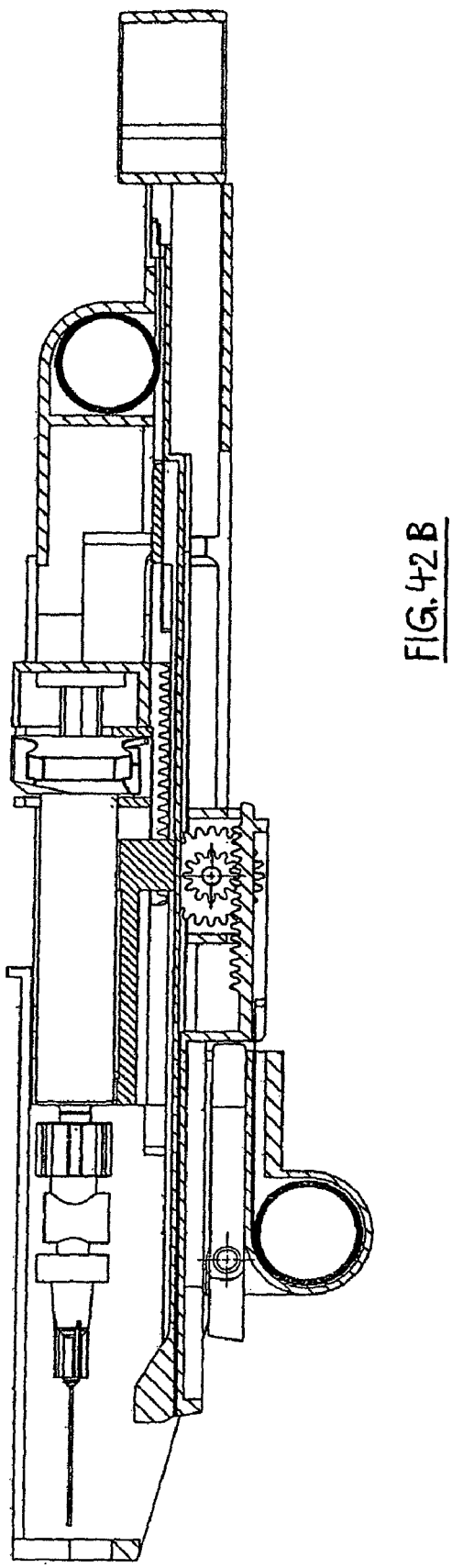
FIG. 42B shows a second longitudinal section through the operating components in their position according to FIG. 42.
Figure 43:
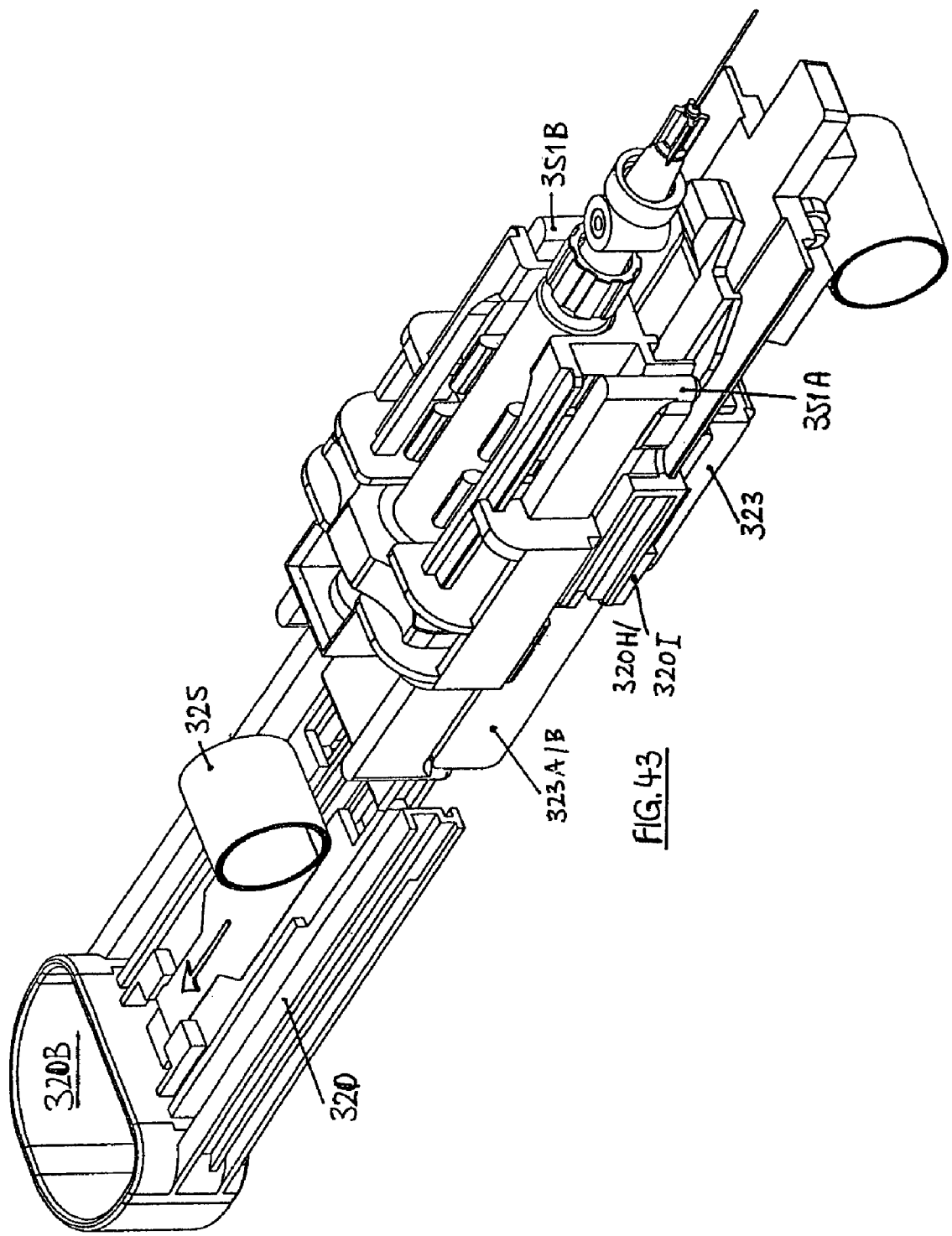
FIG. 43 shows a first perspective partial view of essential operating components during the loading procedure.
Figure 44:
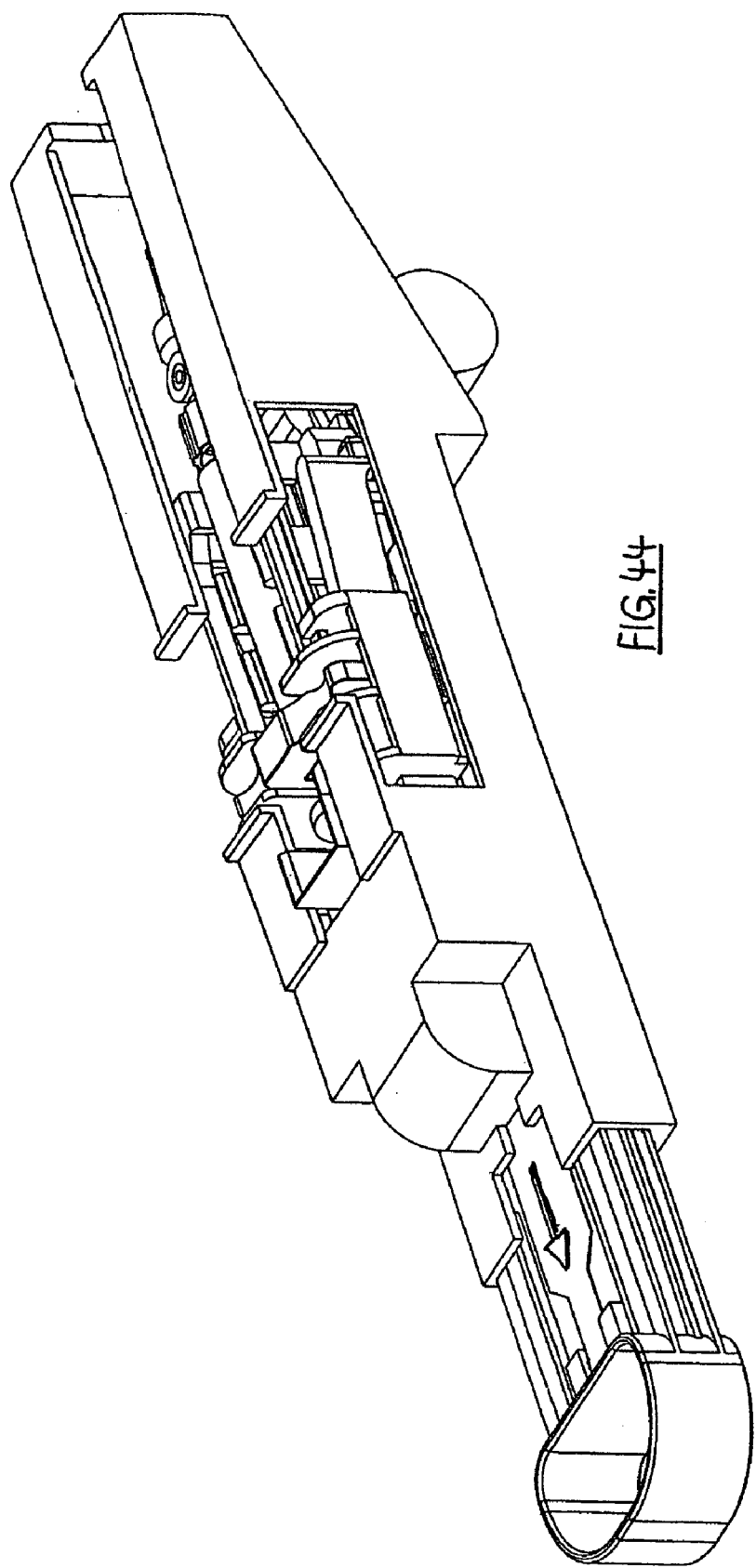
FIG. 44 shows a second perspective partial view of essential operating components during the loading procedure.
Figure 44A:
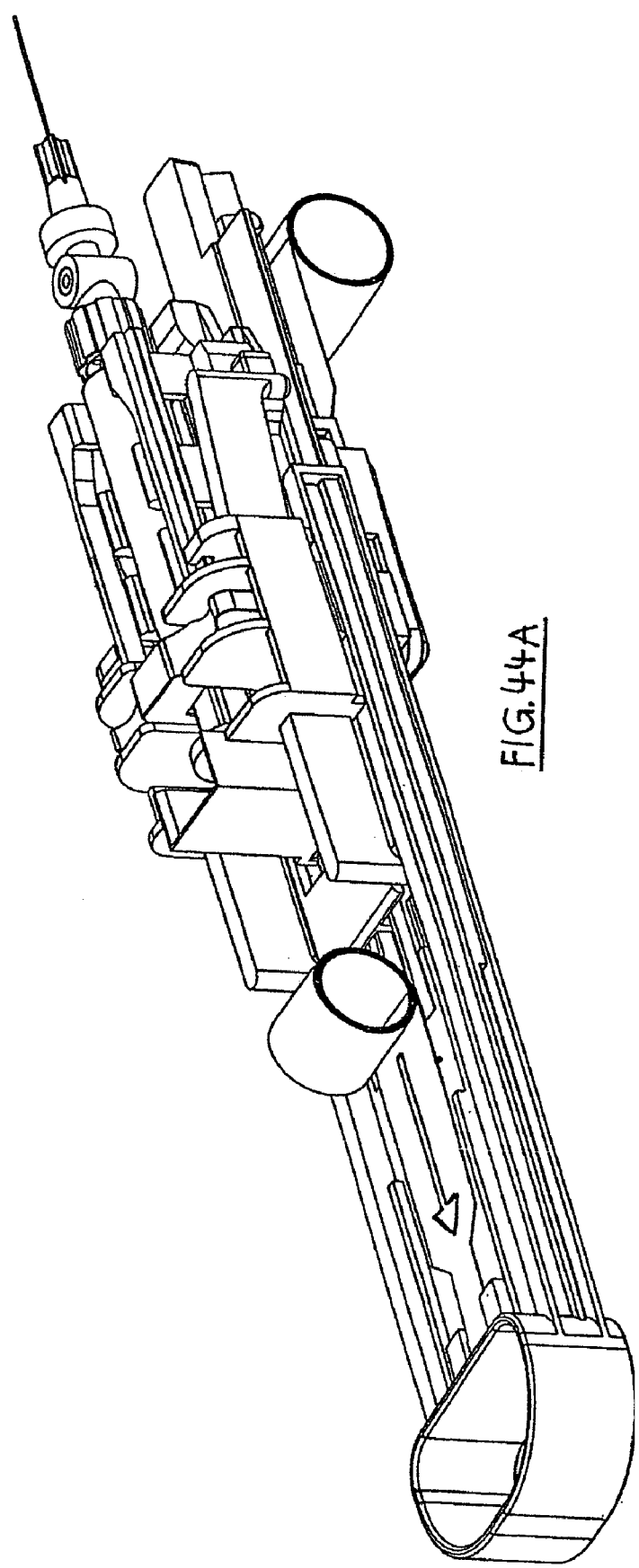
FIG. 44A shows a first longitudinal section through the operating components in their position according to FIG. 43/44.
Figure 44B:
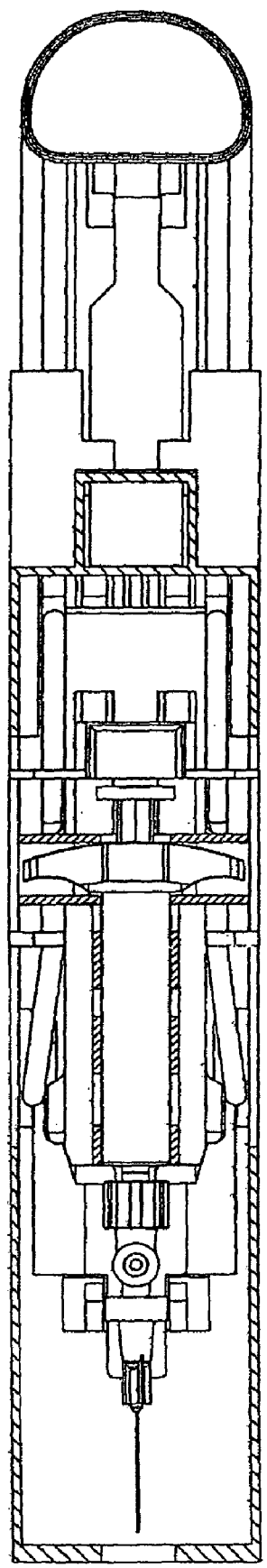
FIG. 44B shows a second longitudinal section through the operating components in their position according to FIG. 43/44.
Figure 44C:
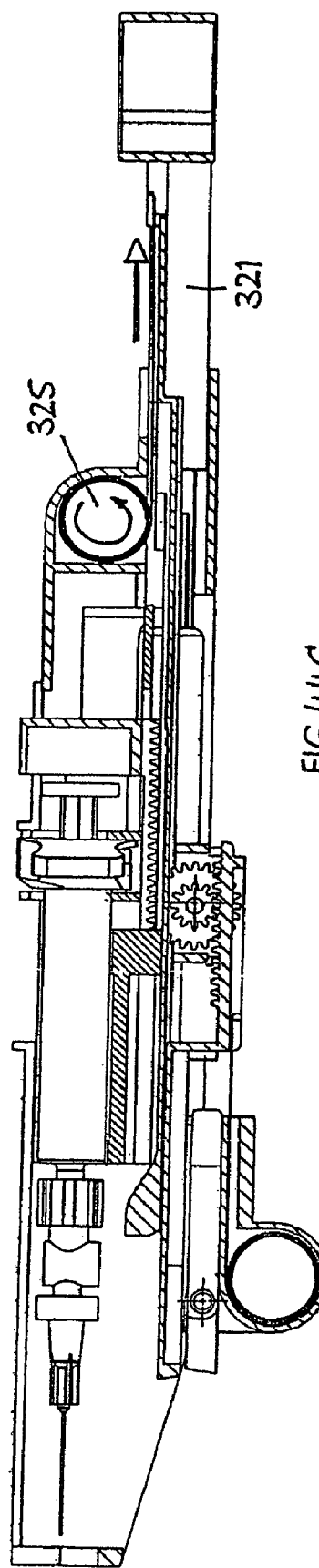
FIG. 44C shows a third longitudinal section through the operating components in their position according to FIG. 43/44.
Figure 45:
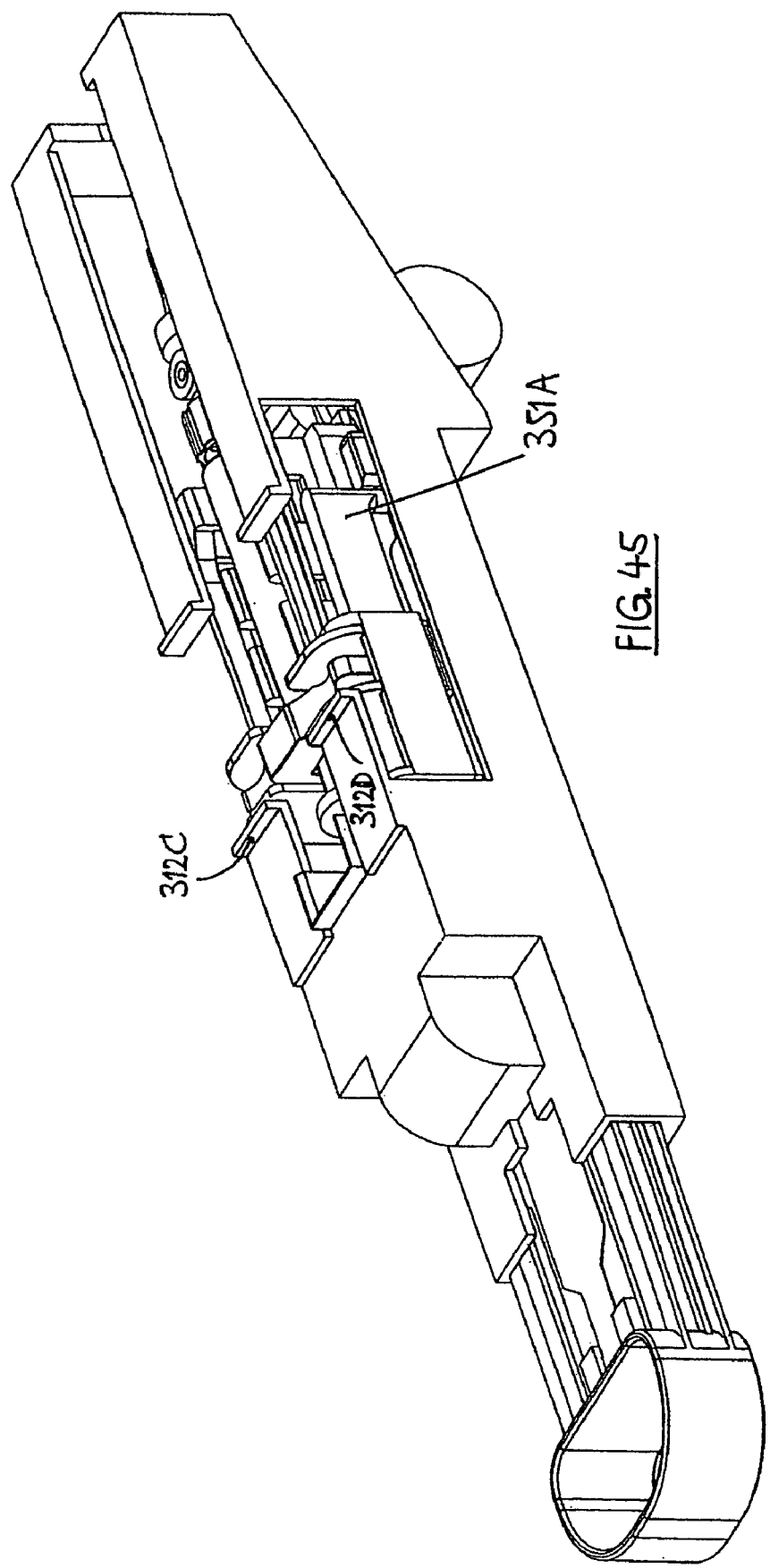
FIG. 45 shows a third perspective partial view of essential operating components during the loading procedure.
Figure 46:
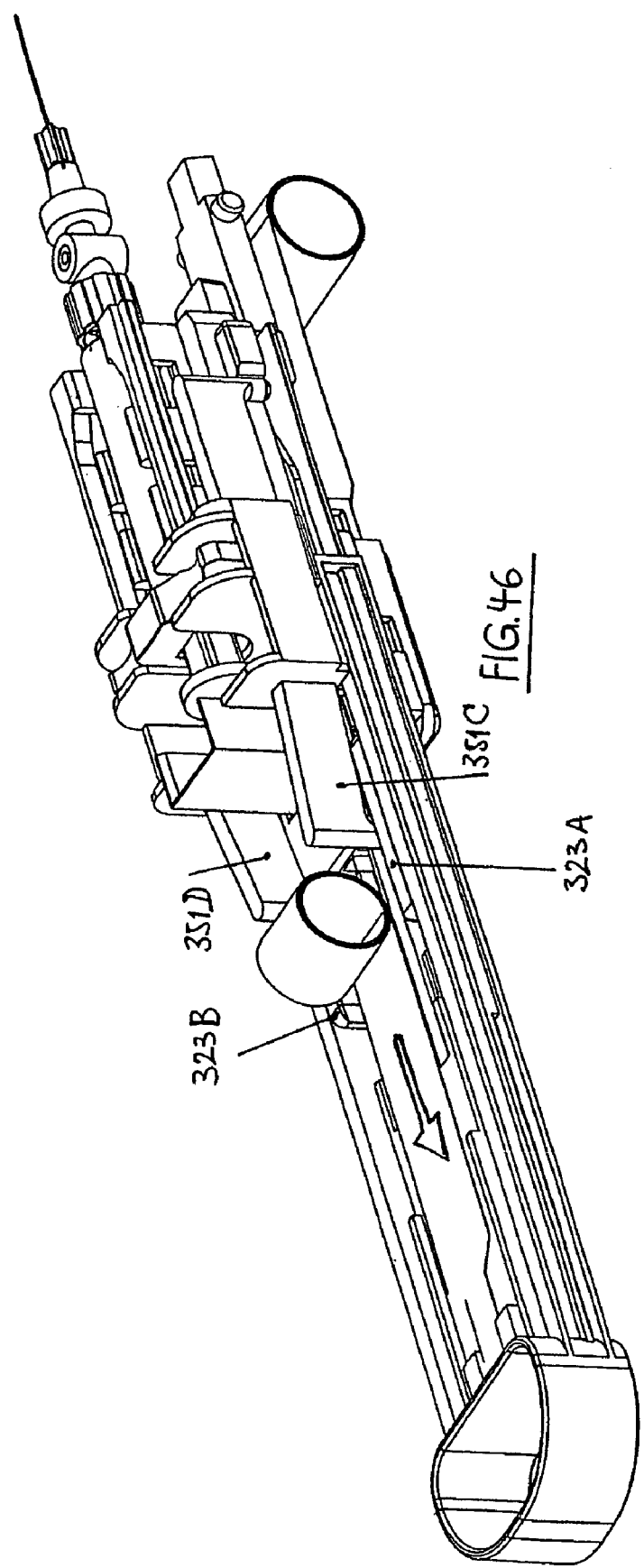
FIG. 46 shows a fourth perspective partial view of essential operating components during the loading procedure.
Figure 47:
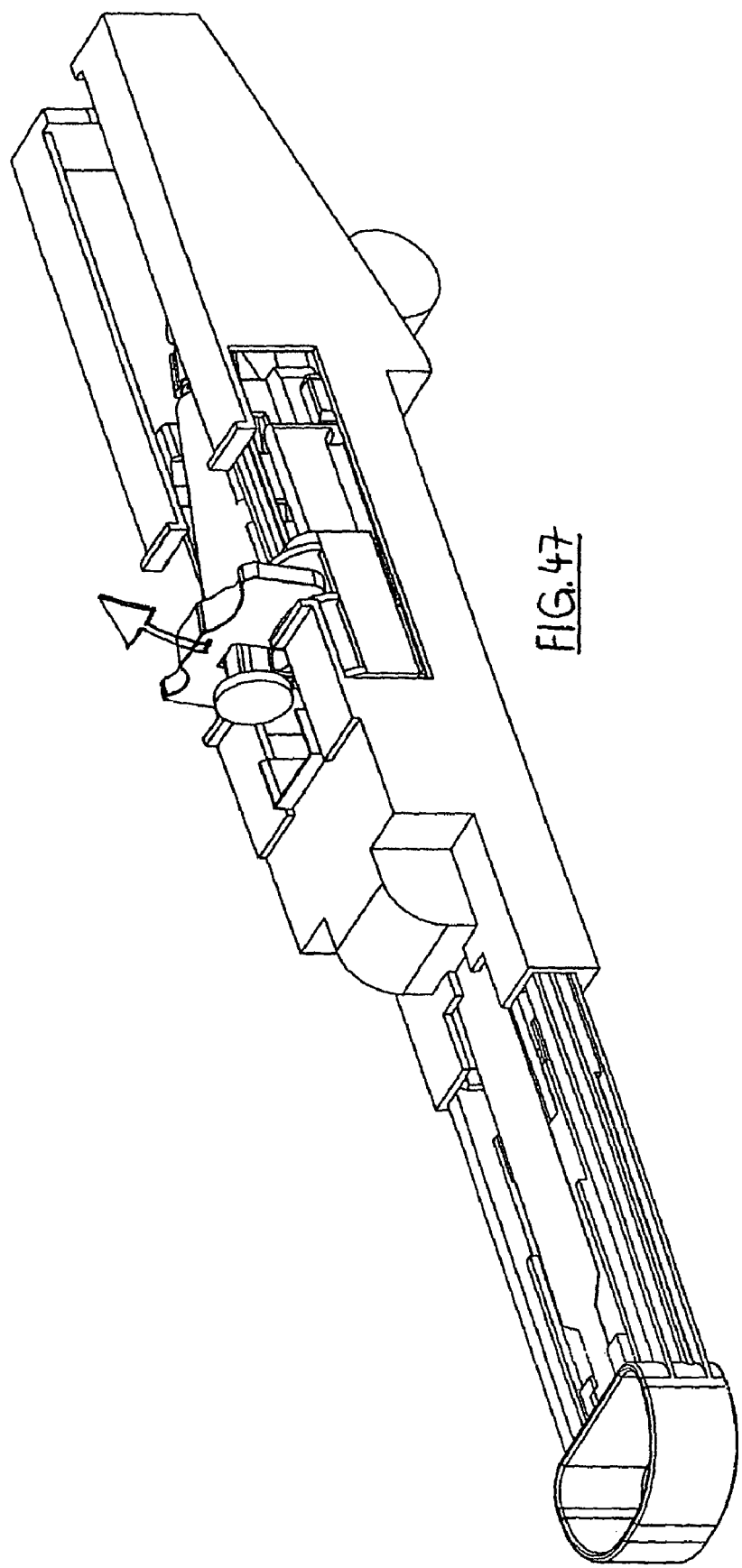
FIG. 47 shows a perspective partial view of essential operating components after the loading procedure and after the syringe ejection.
Figure 47A:
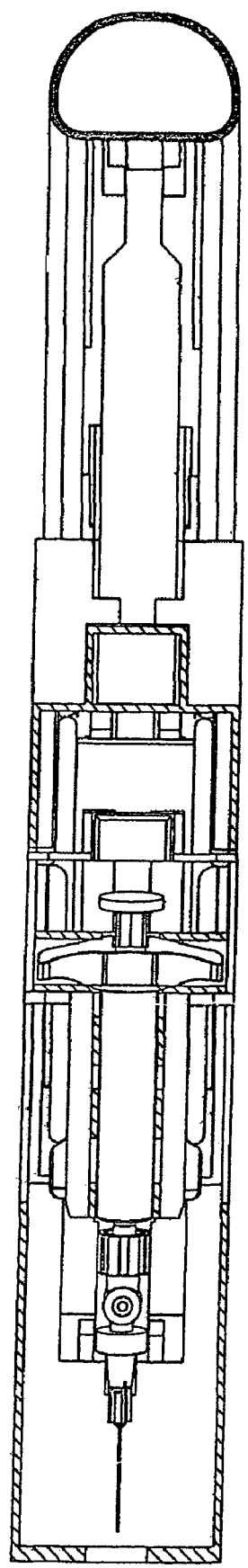
FIG. 47A shows a first longitudinal section through the operating components in their position according to FIG. 47.
Figure 47:
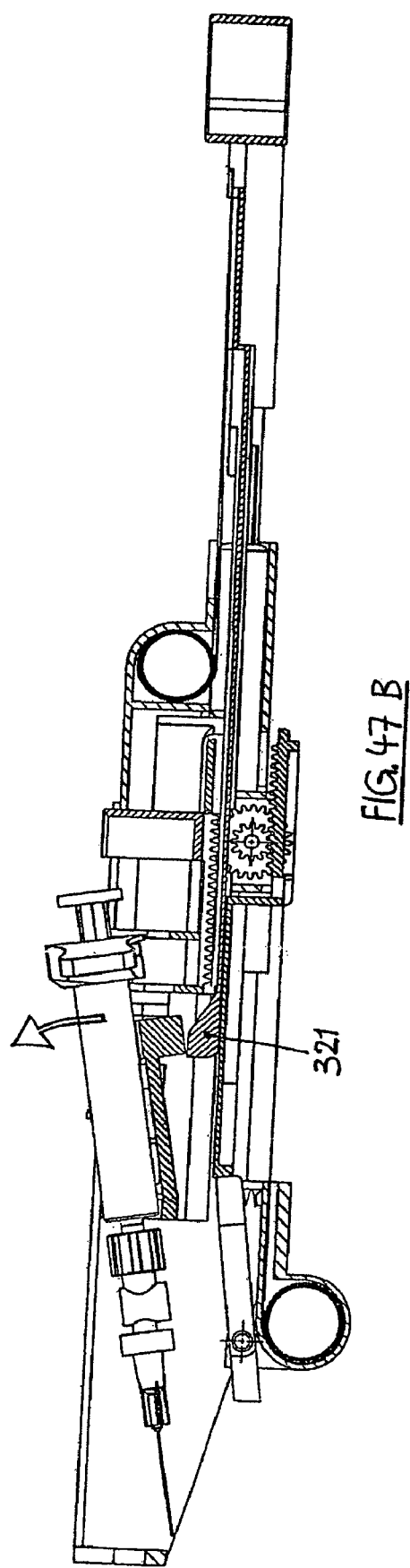

The injection device containing the described components functions as follows:

The injection carriage with the syringe holder 340 and with the frame-shaped ram 350 (FIGS. 24, 25) is situated, in the start position shown in different views in FIGS. 33-37, on a rear limit stop 312C and 312D of the receiving frame 312A, 312B, and a syringe 300 filled with medicament is inserted (FIGS. 36, 37).

The insertion stroke H1 of the syringe 300 (FIG. 37) is triggered by activation of the trigger mechanism 370 (FIGS. 30, 31), by which means the advancer spring 324 pulls the advancer carriage 323 in the injection direction. Ram 350 and advancer carriage 323 are initially connected rigidly to one another via the toothed wheel gearing 328 and the locking arms 351A, 351B and 323A, 323B. The locking arms are guided and, only when a predetermined axial position of the advancer carriage 323 is reached, can they be deflected laterally by release of the receiving frame 312A, 312B or the pull-out loading bar 320 and/or the syringe holder 340: the locking arms 351A, 351B are released by the end of a guide wall on the pull-out loading bar 320 when the syringe holder 340 has reached a front limit stop on the receiving frame 312A, 312B.

The syringe holder 340 with the syringe 300 then travels forward, and the needle 308 penetrates into the skin (insertion stroke H1).

Upon further advance of the advancer carriage 323, the end face 352 of the ram 350 presses the plunger 304, via the flange 302 and the plunger rod 305, into the syringe 300 and the medicament is injected. The locking arms 351A, 351B of the ram 350 yield past pusher lugs 341A, 341B of the syringe holder 340 (injection stroke H2, FIG. 38).

The injection stroke H2 is completed (FIG. 39) when the ram 350 strikes against the rear wall 342 of the syringe holder 340 and the locking hooks 351A, 351B of the ram 350 are locked behind the pusher lugs 341A, 341B of the syringe holder 340 (arrows PA, PB). The medicament is now injected. A deflection of the locking arms 323A, 323B of the advancer carriage 323 is now possible, and the advancer carriage 323 can begin the process of performing the return stroke H3.

To ensure a complete injection of the medicament, the return movement of the syringe ought not to start until after a certain time delay. For this reason, the advancer carriage 323 with its abutment bars 328A, 328B (FIGS. 26-28) must move ca. 2.5 mm further to the limit stop wall 312F of the receiving frame 312.

For this purpose, the locking arms 323A, 323B of the advancer carriage 32 pivot downward on the hooks 351C, 351D of the ram 350, and the toothed wheels 313A, 313B move the advancer carriage 323 over the toothed wheel 313C in the direction to the limit stop wall 312F.

For the syringe return movement (return stroke H3, FIG. 41), the advancer carriage 323 lies with its abutment bars 328A, 328B on the limit stop wall 312F of the receiving frame 312. The advancer spring 324 pulls the advancer carriage 323 further. Ram 350, syringe holder 340 and syringe 300 are moved back again via the toothed wheel gearing 328.

Figure 33:
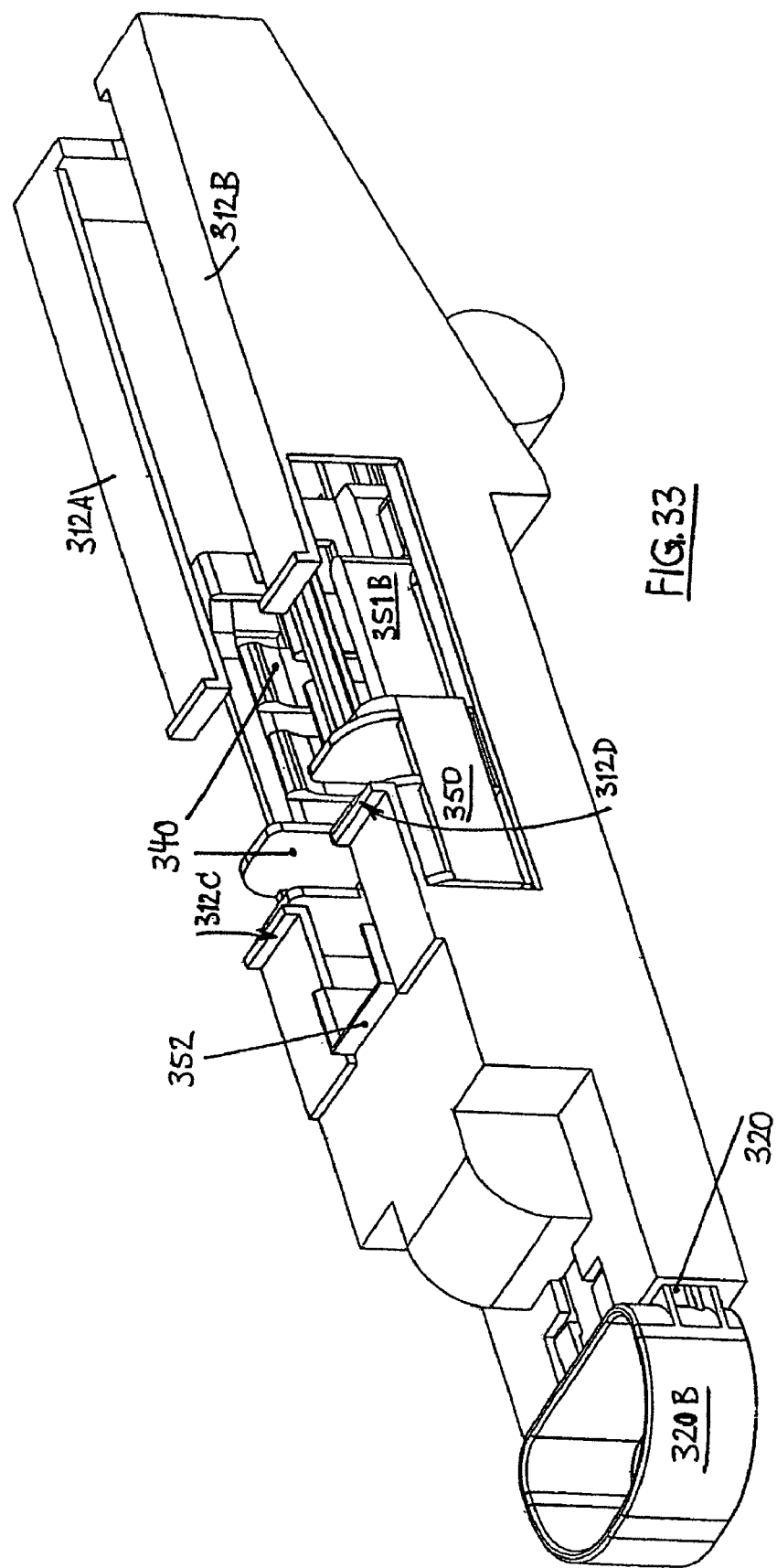
FIG. 33 shows a perspective view of the top of the injection device according to FIG. 22 with both halves of the receiving frame.
Figure 34:
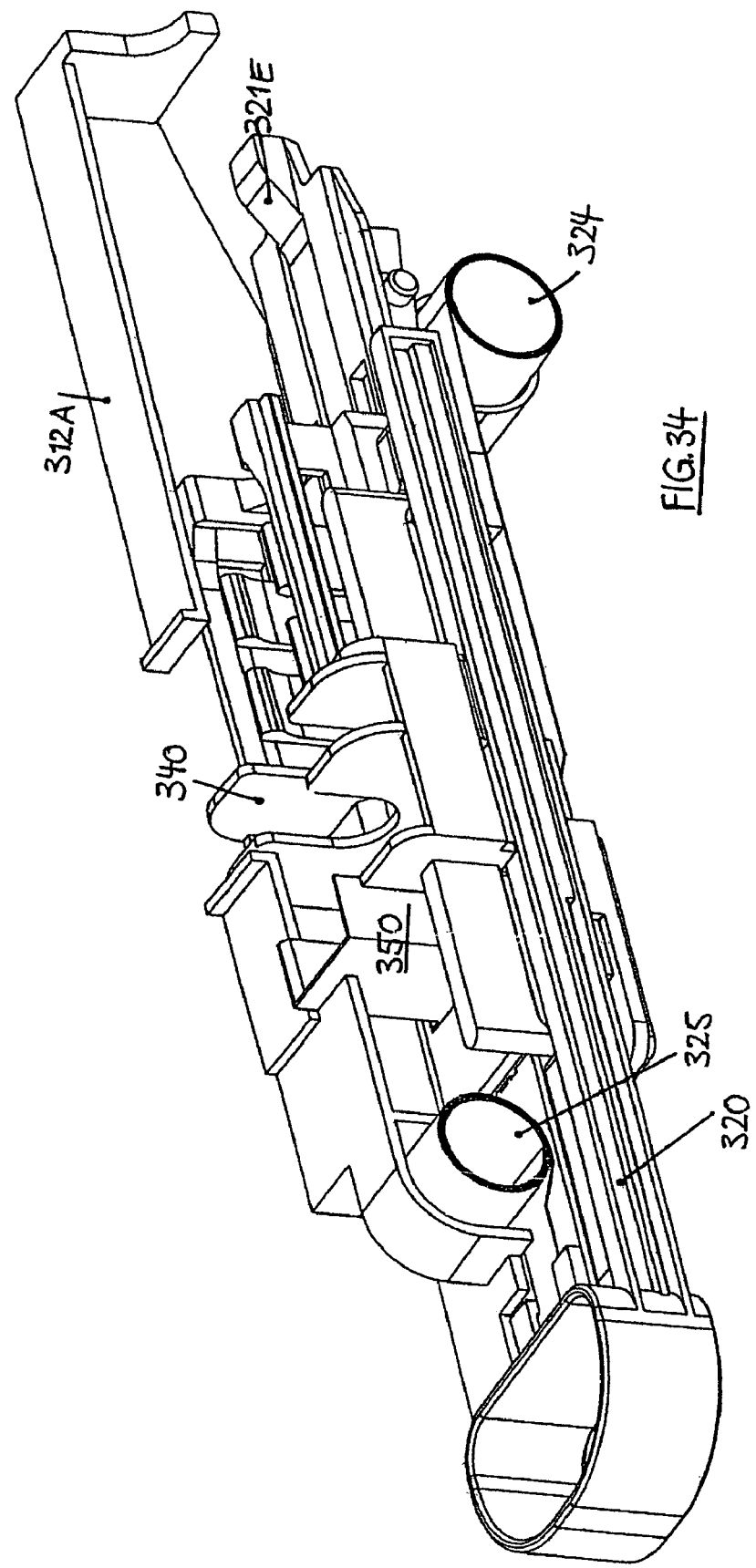
FIG. 34 shows a perspective view of the top with one half of the receiving frame according to FIG. 22.

The syringe return movement is completed (FIG. 42) when the syringe holder 340 has been driven against the limit stop 312C, 312D of the receiving frame 312 (FIG. 33). The locking arms 323A, 323B of the advancer carriage 323 engage again behind the hooks 351C, 351D of the ram 350. The needle 380 is pulled completely from the skin.

At the end of the syringe return movement, the bell ring mechanism 380 (FIG. 32) is triggered by the advancer carriage 323.

To load the injection device (FIGS. 43-47), the pull-out loading bar 320 must be pulled out via its grip 320B from the receiving frame 312. The locking arms 323A, 323B of the advancer carriage 323 are blocked by blocking hooks 320H, 320I of the pull-out loading bar 320. At the same time, the hooks 351A, 351B of the ram 350 are freed, and traction edges of the pull-out loading bar 320 strike the locking arms 323A, 323B of the advancer carriage 323.

When the pull-out loading bar 320 is pulled out further (FIG. 44), the injection carriage moves with the ram 350 back into its starting position. The locking arms 351A, 351B of the ram 350 yield and move past the pusher lugs 341 of the syringe holder 340.

In the further course of the loading procedure (FIG. 45), the injection carriage is again located itself on the limit stop 312C, 312D of the receiving frame 312. The locking arms 351A, 351B of the ram 350 are engaged again behind the pusher lugs 341 of the syringe holder 340. The locking arms 351A, 351B of the ram 350 are freed by the pull-out loading bar 320 and the syringe holder 340 and are able to deflect.

As the pull-out loading bar 320 is pulled out further (FIG. 46), the hooks 351C, 351D of the ram 350 pivot inward on the locking arms 323A, 323B of the advancer carriage 323 and run past the sides of these. The advancer carriage 323 and the toothed wheel gearing 328 move back again to their starting position.

At the end of the loading procedure (FIG. 47), the locking arms 351A, 351B of the ram 350 engage again behind the locking arms 351A, 351B of the advancer carriage 323. Advancer carriage 323 and toothed wheel gearing 328 are located again in the starting position.

At the end of the pull-out loading bar 320 there is a press lug 321E which actuated an ejector hook 343 (FIG. 36C) on the syringe holder 340 and tilts the syringe 300 upward for better removal.

After the grip 320B of the pull-out loading bar 320 is let go, the latter is drawn back to its starting position again by the restoring force of the restoring spring 325.

The advancer carriage 323 engages again behind the trigger pivot lever 374 and is tensioned again by the restoring force of the advancer spring 324.

At the end of the syringe return movement, the bell ring mechanism 380 (FIG. 32) is triggered by the advancer carriage 323.

Fourth Illustrative Embodiment

The basic structure of the injector corresponds, in terms of its main components, to the third illustrative embodiment, so that only the essential differences in structure and function are set out below.

Figure 48A:
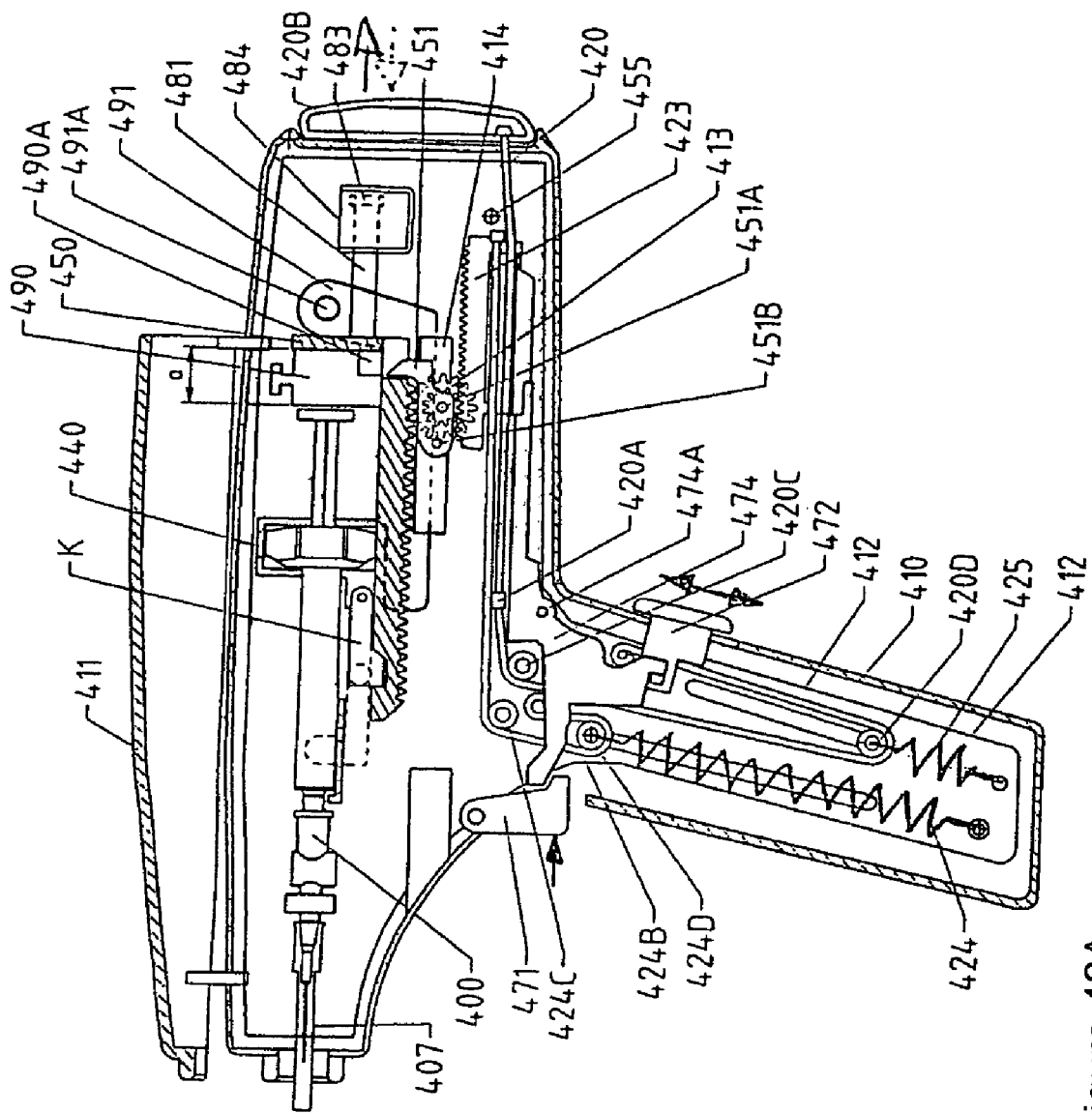
FIG. 48A shows a fourth illustrative embodiment in a longitudinal section with inserted syringe and with a volume adapter in the starting state.

FIG. 48A shows the main elements of the fourth illustrative embodiment:

The syringe 400 is inserted into the syringe holder 440. Inserted and locked between the ram 450 and the syringe holder 440, there is a volume adapter 490 by means of which the injection stroke H2 can be shortened, by shortening the distance of the end of the syringe plunger from the inside wall of the syringe holder. Depending on the desired injection volume (e.g. 0.5, 0.75 or 1.0 ml), a suitable volume adapter 490 is pushed into the ram 450. The respective volume adapters 490 differ by the distance a and the position of a control rib 490A which is located on the respective volume adapter. The control rib 490A interacts with a volume control lever 491.

Figure 50:
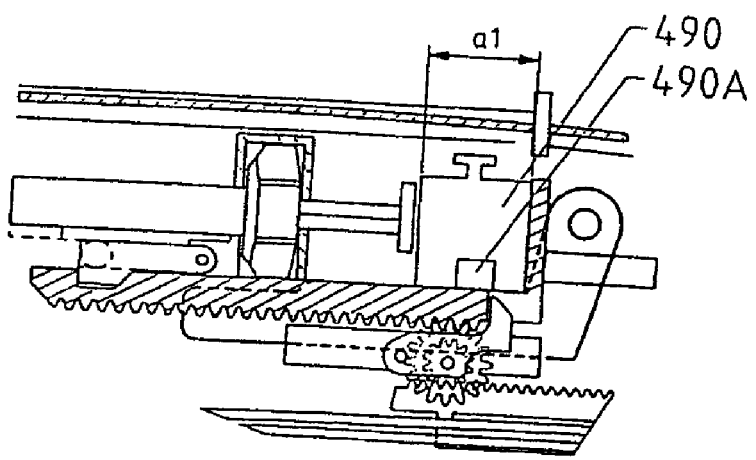
FIG. 50 shows a partial section through the fourth illustrative embodiment with larger volume adapter.

FIG. 50 shows a larger volume adapter for a smaller injection volume than in FIG. 48A (a1>a, position of the control rib 490A altered).

To allow the strokes to be performed, an arrangement comprising a pull wire 424B, pull-out loading wire 420, compression spring 424 and restoring spring 425 is provided; the traction spring 424 generates the advancing force acts with a suitably stepped-down traction force on the advancer carriage 423 via an arrangement in the manner of a pulley with a deflection roller 424D and the pull wire 424B. The pull-out loading wire 420 likewise runs via a deflection roller 420D, which is connected to the restoring spring 425, to a grip 420B at the end face of the housing 410 and entrains the advancer carriage via a carrier 420A.

A further important development of the injector lies in the fact that these components are designed in such a way that, after the injection stroke H2 has been performed, a delay TV can be set, and the return stroke H3 starts only after this delay has elapsed. This delay has the advantage that the pressure that has been produced in the subcutaneous tissue by the injection of the medicament is able to subside before the needle is withdrawn, as a result of which the penetration of medicament into the insertion channel of the needle is largely avoided.

In design terms, this effect is achieved by the fact that although the advancer carriage 423 and the housing 414 with the double toothed wheel 413 continue to move during the delay TV, they do so without further coupling of the ram 450, and the initiation of the return stroke H3 with corresponding coupling of the syringe holder 440 takes place only after an idle stroke H0 of the advance carriage 423 determining the delay TV.

The change-over point from the injection stroke H2 to the idle stroke H0 varies depending on which volume adapter 490 is used.

Figure 49:
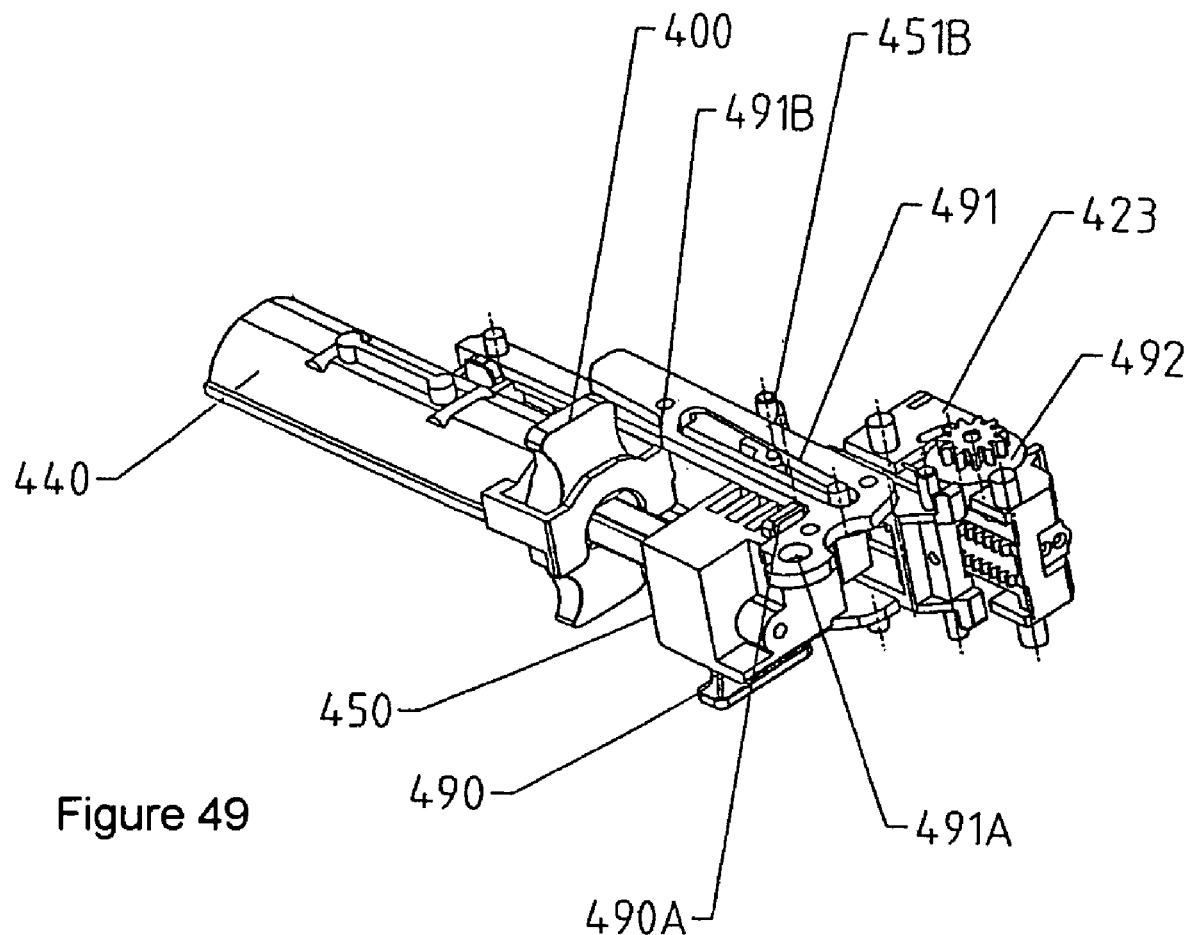
FIG. 49 shows a perspective partial view of the injection carriage with an inserted volume adapter.

A further embodiment lies in the provision of a damping member 492 (FIG. 49). A damping member of this kind is assigned to the advancer carriage and damps the latter's movement during the advance, in order to achieve longer injection times through a slower movement of the ram 450.

Supplementary components are explained in the now following description of the sequence of the functions:

In the starting state of the injection device, the advancer spring (traction spring) 424 is tensioned and acts on the pull wire 424B via the pull roller 424D. One end of the pull wire 424B is secured on the receiving frame 412, and the other end is secured on the advancer carriage 423, a deflection of the pull wire 424B taking place via the deflection roller 424C. Because of the mode of action of a single pulley, half the force of the advancer spring 424 acts on the advancer carriage 423. To minimize the spring travel, or to adapt the travel/force characteristic related to the advancer carriage 423 to the individual case of use, a double pulley, combined with one or more springs, is also possible.

The restoring spring 425 (traction spring) is released except for the pretensioning, acts via the roller 420D with half its force on the pull-out loading wire 420, which likewise in the manner of a pulley is secured with one end on the receiving frame 412 and with its other end on the grip 420B. The pull-out loading wire is guided through the advancer carriage 423, but is not connected to the latter. A carrier 420A is secured on the pull-out loading wire 420, the external diameter of this carrier 420A being greater than the bore in the advancer carriage 423 through which the pull-out loading wire 420 is guided.

The advancer carriage 423 is thus acted upon with half the force of the advancer spring 424; it remains in its position because it is supported by a trigger pivot lever 474 with hinge point 474A.

The mechanical process is triggered by actuation of a button-like switch element 471 which, via a bevel, pivots the trigger pivot lever 474 about the hinge point 474A and in this way releases the advancer carriage 423.

However, the trigger pivot lever 474 can only be pivoted when a safety slide 472 has first been pushed in the direction of the arrow A (release position).

After triggering by the switch element 471, a rigid connection of the advancer carriage 423 to the ram 450 is obtained, because the teeth of the advancer carriage 423 mesh with the smaller toothed wheel of the toothed wheel pair 413, and the larger toothed wheel meshes with the teeth of the ram 450, the toothed wheel pair is mounted in the housing 414, and a carrier lever 451, which is likewise mounted pivotably in the housing 414, engages with positive locking in the ram 450.

By means of a coupling element K, here shown as a pawl which connects the ram 450 to the syringe holder 440, said syringe holder 440 and said ram 450 are coupled in such a way that they first execute the insertion stroke (H1) in a uniform movement.

The carrier lever 451 is mounted pivotably in a pin 451A. The distance between the pin 451A and the point of application of force on the ram 450 results in a rightward torque as soon as the advancer carriage 423 moves and the advancing force is transmitted via the toothed wheels and the carrier lever 451 to the ram 450. However, a rotation of the carrier lever 451 is prevented at this time by a cam 451B which bears on a control lever 491.

The control lever 491 is mounted rotatably on the receiving frame 412 at its bearing point 491A, but is not able to turn because it abuts the control rib 490A of the volume adapter 490.

Therefore, the syringe holder 440 and the ram 450 jointly execute the stroke 1 (insertion stroke). The control rib 490A slides on the control lever 491 and prevents the latter from pivoting out and thereby also prevents rotation of the carrier lever 451.

Figure 48B:
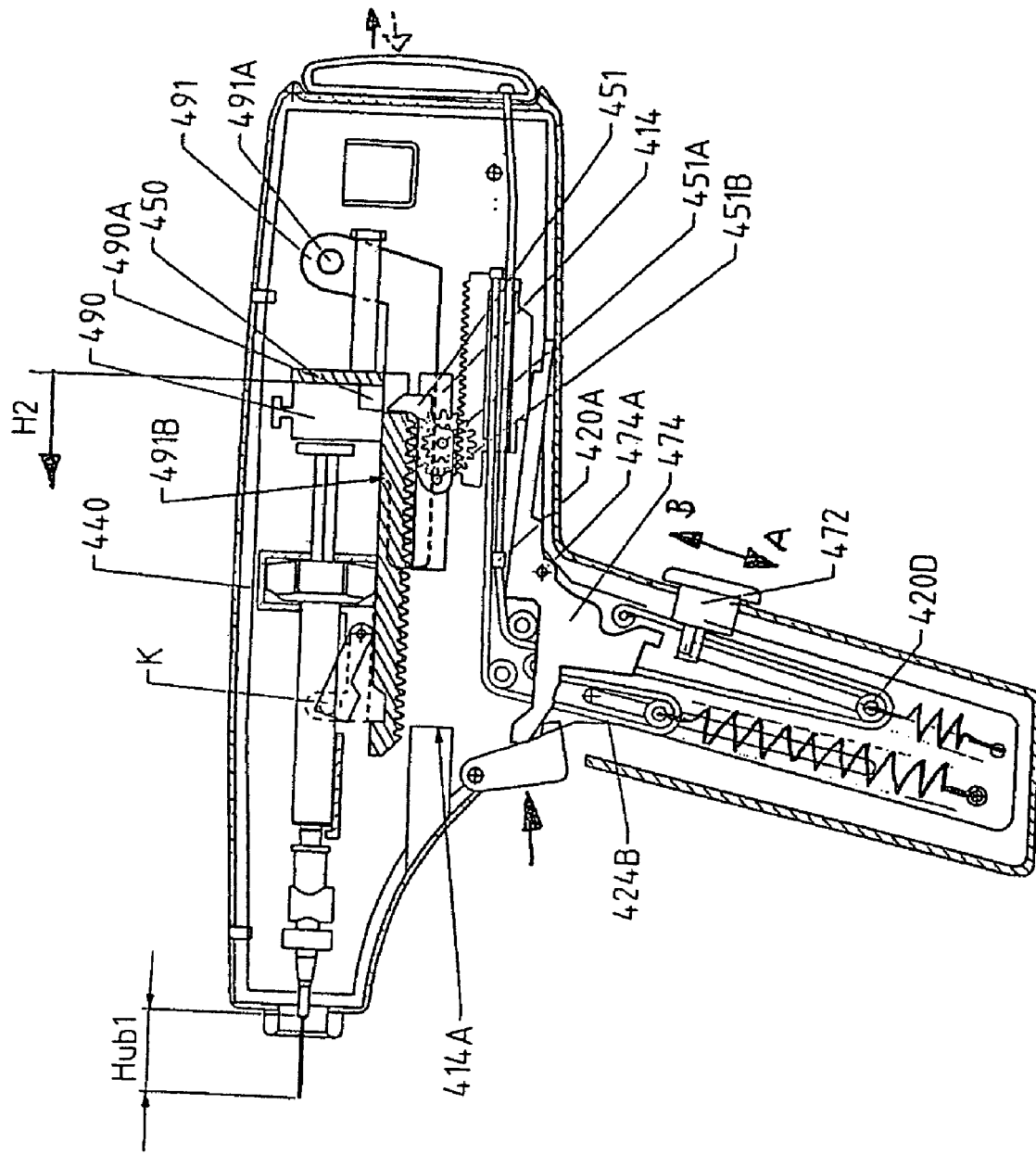
FIG. 48B shows a section after completion of the insertion stroke.

After the insertion stroke 1, the connection of syringe holder 440 and ram 450 is released by a pivoting of the coupling element K (FIG. 48B). The syringe holder 440 remains in its position, the ram 450 is moved onward, and the insertion stroke H2 and injection of the medicament begins.

Since the volume adapter 490 and thus the control rib 490A move away from the bearing point of the pin 491A of the control lever 490 during the injection, the control lever 490 and thus the carrier lever 451 are unable to turn about their bearing points until the control rib 490A reaches the bevel 491B. As soon as the latter is reached, the control lever 491 can be lifted by a cam 451B, the carrier lever 451 turns about its bearing 451A, and the positive engagement with the ram 450 is canceled. The injection stroke H2 is completed (FIG. 48C).

If a volume adapter 490 for a smaller injection volume is fitted, this increases the distance between the rear wall of the ram 450 and the plunger rod. The control rib 490A then sits closer to the bevel 491B, i.e. the injection stroke H2 is smaller because the control rib 490A reaches the bevel 491B after a shorter travel.

Figure 48C:
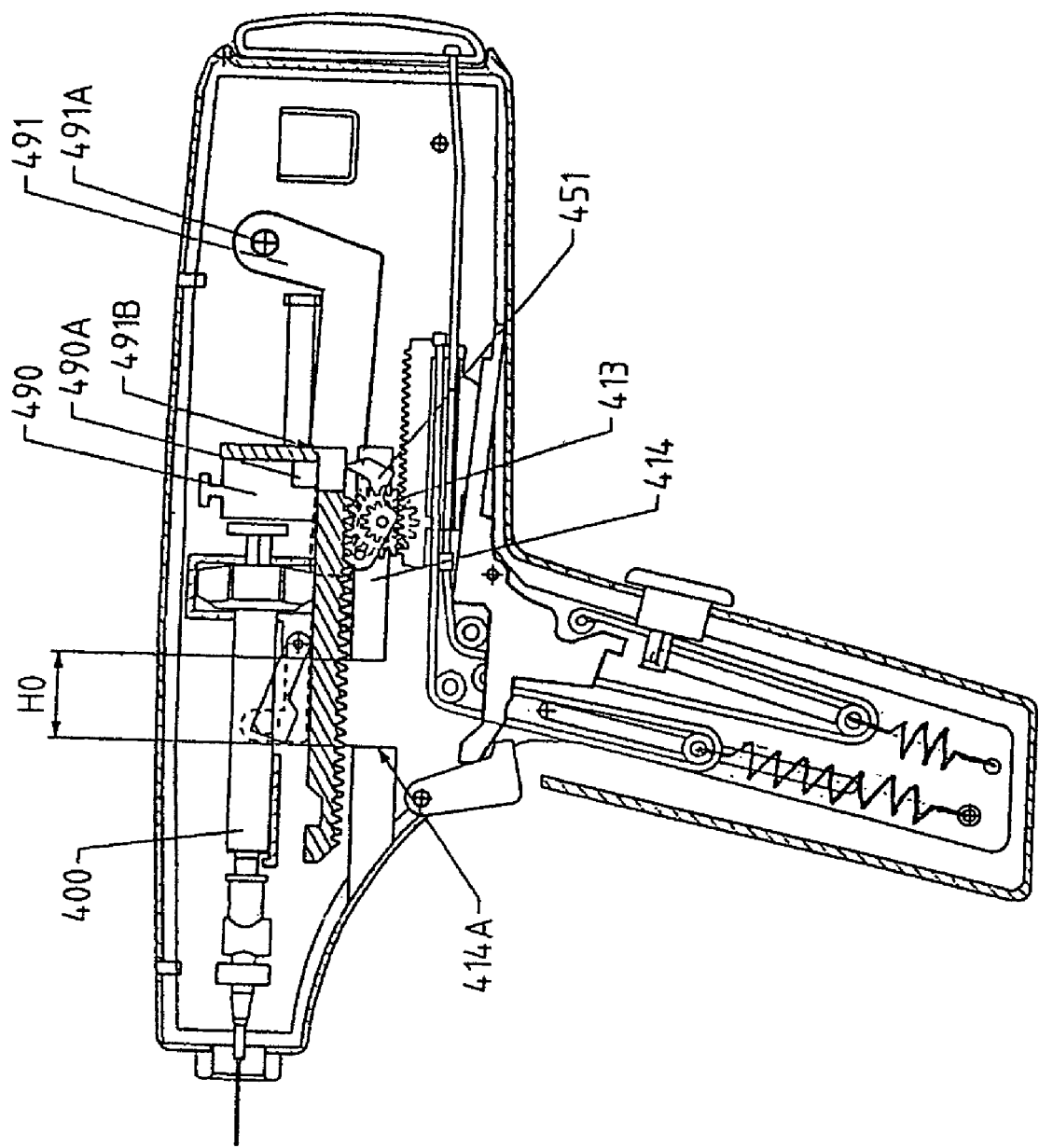
FIG. 48C shows a partial section after completion of the injection stroke.

As is shown in FIG. 48C, at the time of release of the rotation of the carrier lever 451, the housing 414 with the double toothed wheel 413 has not yet reached a limit stop 414A. Therefore, the toothed wheel pair 413 simply rolls on the two sets of teeth until the limit stop 414A is reached.

The idle stroke H0 thus produced ensures that the needle return does not take place immediately after the insertion stroke H2, but is instead delayed by the delay TV.

It is only when the limit stop 414A is reached that the ram 450 is moved in the opposite direction, resulting in a translation according to the reference circles of the two toothed wheels. After a travel that corresponds to the extent of the insertion stroke H1, the syringe holder 440 is coupled, and in this way the needle is automatically withdrawn and the return stroke H3 is completed.

Before renewed injection, the advancer spring 424 has to be tensioned:

Housing 414 and advancer carriage 423 are situated in their end position, and the advancer spring 424 is released except for its pretensioning. The carrier 420A bears on the wall of the advancer carriage 423. If the grip 420B is now pulled, the carrier 420A secured fixedly on the pull-out loading wire 420 transports the advancer carriage 423 into its starting position, and the trigger pivot lever 474 pivots in front of the advancer carriage 423 and fixes the latter. During the return of the advancer carriage 423, the advancer spring 424 is tensioned with the aid of the pull-out wire 424B, which is connected fixedly to the advancer carriage 423. At the same time, the restoring spring 425 is tensioned with the aid of the pull roller 420D, and said pull roller 420D, guided in the receiving frame 412, moves the safety slide 472 in the direction of the arrow B (safety position).

As soon as the grip 420B is let go, the pull-out loading wire 420 draws back in again to its original position.

Figure 51A:
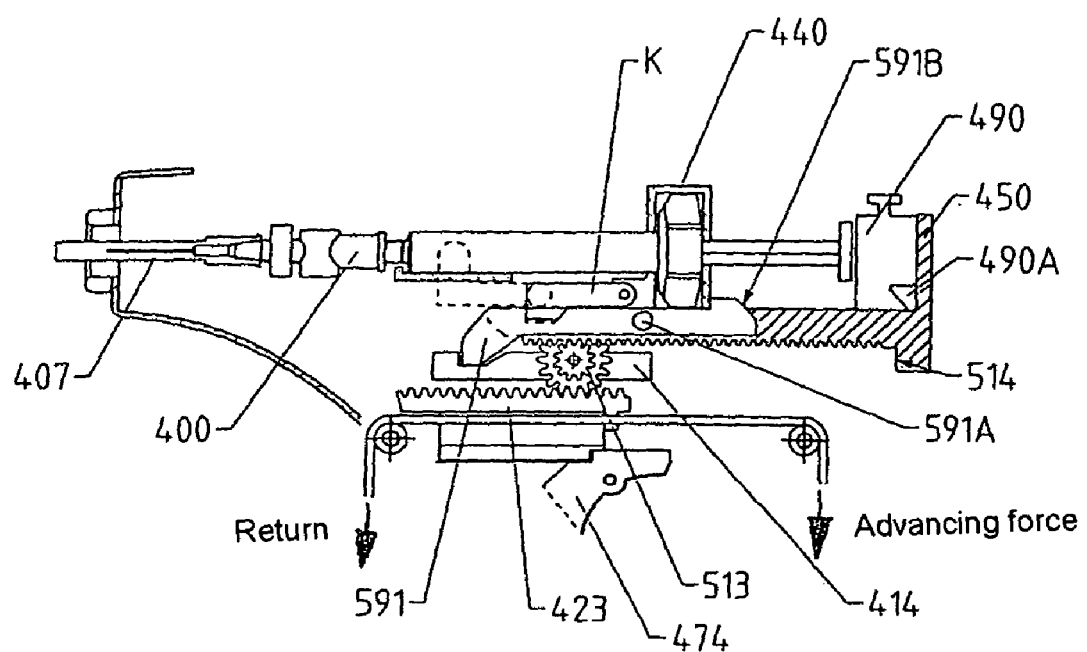
FIG. 51A shows a partial section of a first variant of the drive coupling in the fourth illustrative embodiment, in the starting state.
Figure 51B:
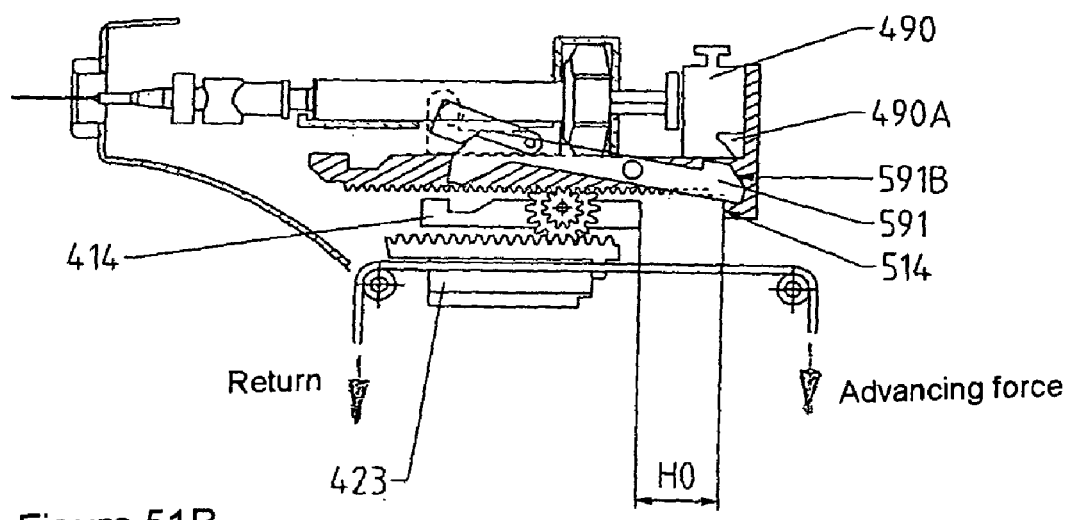
FIG. 51B shows a partial section of the first variant after completion of the insertion stroke.
Figure 52:
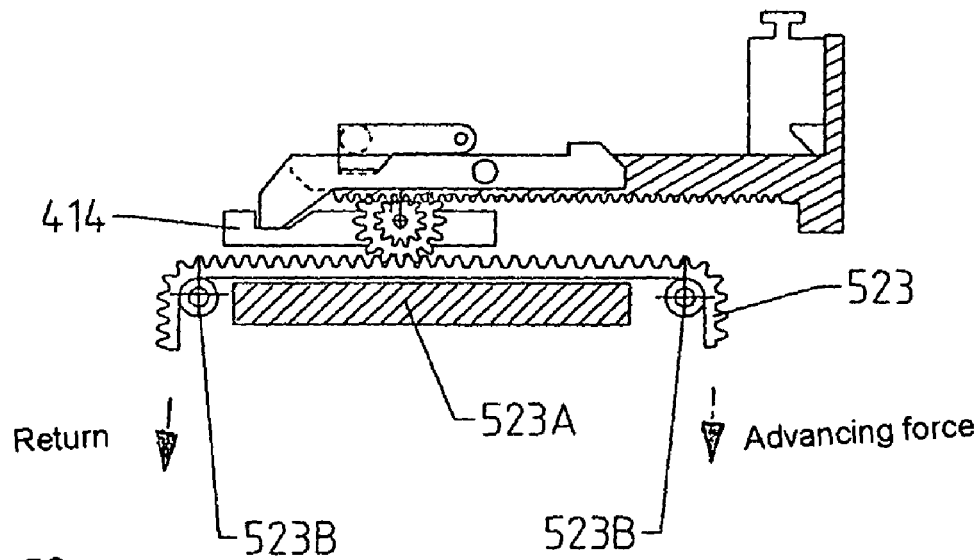
FIG. 52 shows a partial section through a second variant of the drive coupling.
Figure 53:
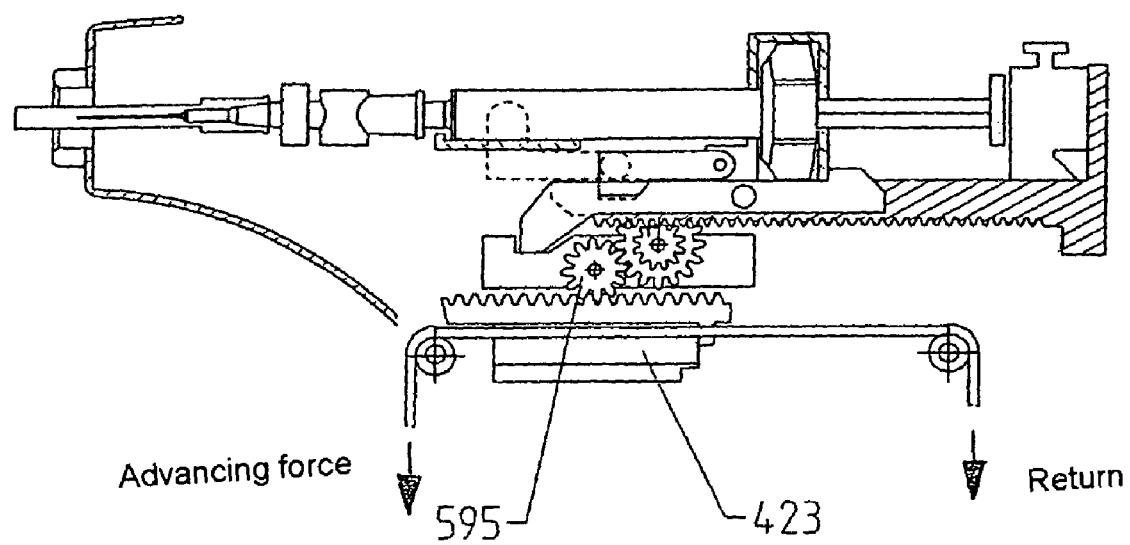
FIG. 53 shows a partial section through a third variant of the drive coupling.

FIGS. 51-53 show variants of the drive coupling which also permit the sequence of insertion stroke H1, injection stroke H2, idle stroke H0 (delay TV) and return stroke H3.

FIG. 51A shows a construction in which the syringe 400, the syringe holder 440, the ram 450, the volume adapter 490 and the coupling element K have the same tasks as have been described above in connection with the fourth illustrative embodiment.

A toothed wheel pair 513 is once again mounted in a housing 414, but, in contrast to the fourth illustrative embodiment, the larger toothed wheel meshes with the advancer carriage 423 and runs freely in a groove in the ram 450, while the smaller toothed wheel meshes with the teeth on the ram 450.

The advancer carriage 423 is loaded by the force of an advancer spring in such a way that it seeks to move toward the right, but it is prevented from doing so by the trigger pivot lever 474.

The control lever 591 is mounted in the frame 412 with a pivot bearing 591A and, in the starting position, engages positively in the housing 414.

As soon as the advancer carriage 423 is released by the trigger pivot lever 474, the advancer carriage moves toward the right. Since the housing 414 is fixed in a stationary position by the control lever, the toothed wheel pair rotates, and ram 450 and syringe holder 440 move jointly toward the left, resulting in stepping down (travel of the ram<travel of the advancer carriage).

After the joint insertion stroke H1, the ram is uncoupled from the syringe holder, and the injection stroke H2 takes place.

As soon as the control rib 490A of the volume adapter 490 reaches the bevel 591B of the control lever 591A, the latter is pivoted, and the positive engagement with the housing 414 is canceled (FIG. 51B).

At this time, the housing has not yet reached the limit stop 514 on the ram 450, for which reason the idle stroke H0 (delay TV) takes place until the limit stop 514 is reached.

When the limit stop 514 is reached, the ram 450 is entrained toward the right in unison with the movement of the advancer carriage 423. After a travel that corresponds in extent to the insertion stroke H1, the syringe holder 440 is coupled in, and the needle withdrawal takes place during the return stroke H3.

The advantage of this principle is that when the greatest force is needed, during the injection stroke H2, there is a stepping-down, for which reason the advancing force can be chosen smaller, and, therefore, the force to be applied manually for tensioning the springs is also smaller.

In this case, the advancer carriage 423 has to travel a longer distance. For reasons of space, it can therefore be advantageous to configure the drive with the aid of a toothed belt 523 which slides on a support 523A and is guided via rollers 523B (FIG. 52).

For the definition of the direction of movement of the advancer carriage 423 or of the toothed belt 523, an intermediate wheel 595 can be fitted in between, as is shown in FIG. 53.

It will be appreciated that the mechanical arrangement discussed here can also be at least partially effected with the aid of electrical/electronic components, for example by stepping motors for generating the strokes, sensors for detecting the positions of the operating components, electronic signalling means, and the like.

The invention claimed is:

1. An injection device for a syringe, having a syringe body, a cannula with a needle, and a plunger with a plunger rod, and having at least one actuating element (120, 220, 320) for converting the actuating work, to be performed manually by the patient, into a displacement of the syringe body (101, 201, 301) during an insertion stroke (H1) and a return stroke (H3), and into a displacement of the plunger rod during an injection stroke (H2), with a guide device in which the syringe body (101, 201, 301) is mounted, and with a ram (150, 250, 350) which can be displaced against this in order to displace the plunger rod, and wherein the actuating work, by means of a single, targeted linear movement of the actuating element (120, 220, 320), is converted into the insertion stroke (H1), the injection stroke (H2) and the return stroke (H3) in such a way that the guide device and the ram (150, 250, 350) are acted on jointly by the actuating element in the insertion stroke (H1) and in such a way that only the ram (150, 250, 350) is acted on in the injection stroke (H2), wherein the guide device includes a displaceable syringe holder (140, 240, 340) in which the syringe (100, 200, 300, 400) is fixed and which is coupled releasably to the ram (150, 250, 350) and is part of an injection carriage, and, in order to perform a return stroke (H3) corresponding in magnitude substantially to the insertion stroke (H1), the actuating element (120, 220, 320, 420) acts on the injection carriage in a positionally and directionally defined manner by means of locking and coupling elements with intercalation of a further carriage (114A, 260, 323, 423).

2. The injection device as claimed in claim 1, wherein the actuating element is a push rod (120, 220) which is guided parallel to the injection carriage in a housing (110, 210) and by means of which, when it is pushed into the housing (110, 210), the components for producing the return stroke (H3) are also activated.

3. The injection device as claimed in claim 2, wherein the components for producing the return stroke (H3) include at least one toothed wheel (113) which engages in the injection carriage (140, 150) and in the push rod (120) and which is mounted in a carriage (114A) displaceable in the housing (110), and wherein the toothed wheel (113) cooperates with a blocking element which blocks the toothed wheel (113), when insertion stroke (H1) and injection stroke (H2) are performed, and which thereafter releases the toothed wheel (113), as a result of which the linear movement of the push rod (120) is converted into the oppositely directed return stroke (H3) of the injection carriage (140, 150).

4. The injection device as claimed in claim 3, wherein at least two toothed wheels (113A, 113B) for converting the linear movement of the push rod (120) into the return stroke (H3) are provided in the common carriage (114A).

5. The injection device as claimed in claim 3, wherein the blocking element is a pawl (114) which is linearly displaceable on the carriage (114A) and which, in the blocking position, engages in the teeth of the toothed wheel (113).

6. The injection device as claimed in claim 3, wherein the blocking element is a pivot lever (114B) which, in the blocking position, engages in the teeth of the push rod (120).

7. The injection device as claimed in claim 2, wherein the coupling between syringe holder (140) and ram (150) is effected by two slide blocks (145A, 145B) which can be brought into a releasable positive engagement between syringe holder (140) and housing (110), and between syringe holder (140) and ram (150).

8. The injection device as claimed in claim 2, wherein the coupling between syringe holder (140) and ram (150) is effected by a further toothed wheel (113C) which is likewise held in the carriage (114A) and which is blocked during the insertion stroke (H1).

9. The injection device as claimed in claim 2, wherein components for producing the return stroke (H3) include at least one spring element (261A, 261B) as energy accumulator which, before the start of the injection, is pretensioned by the push rod (220) (tensioning stroke) and, after the injection stroke (H2), is released, in order to produce the return stroke (H3) by acting abruptly on a return carriage (260) which is releasably connected to the injection carriage and which bears on the syringe holder (240).

10. The injection device as claimed in claim 9, wherein the return carriage (260) has pincer-like locking elements (262A, 262B) which, after the injection stroke (H2), engage in recesses (226A, 226B) of the push rod (220) and release the return stroke (H3).

11. The injection device as claimed in claim 2, wherein a rotatably mounted control lever (221) is provided in the push rod (220), one end of this control lever (221) engaging in the injection carriage (240, 250) when the tensioning stroke has been completed.

12. The injection device as claimed in claim 11, wherein the control lever (221), by turning about a control angle, also effects the release of the coupling between syringe holder (240) and ram (250) at the transition from the insertion stroke (H1) to the injection stroke (H2).

13. The injection device as claimed in claim 1, wherein the actuating element includes a pull-out loading wire (420) which, when pulled out from the housing (310), pretensions at least one advancer spring (424) as energy accumulator, and a trigger mechanism (370) which, after activation, releases the injection carriage (340, 350) acted upon by the advancer spring (324) via an advancer carriage (323) for automatic execution of insertion stroke (H1), injection stroke (H2) and return stroke (H3), and one end of the pull-out loading wire has a grip (420B) on an end of the housing (410), and which has a carrier (420A) which is connected to the advancer spring (424) and engages on the advancer carriage (423) when the grip (420B) is pulled out.

14. The injection device as claimed in claim 13, wherein, the pull-out loading wire (420), after it has been pulled out from the housing (310), pretensions at least one restoring spring (325) as energy accumulator for automatic return of the pull-out loading wire (420), and further wherein the pretensioning of the restoring spring (425) likewise takes place via the grip (420B) and the pull-out loading wire (420), as a result of which the pull-out loading wire (420) is pulled into the housing (410) until it abuts against the grip (420B) on the housing (410).

15. The injection device as claimed in claim 14, wherein the advancer spring (424) and restoring spring (425) are designed as helical springs, one end of which is secured in a frame (412) held in the housing (410), and the other end of which is connected to the pull-out loading wire (420) either directly or via the carrier (420A).

16. The injection device as claimed in claim 15, wherein the other end of the pull-out loading wire (420) is connected to a receiving frame (412) held in the housing and is guided over at least one pull roller (420D) on whose shaft the other end of the restoring spring (425) is held, so that the tensile force applied by the restoring spring (425) on the pull-out loading wire (420) corresponds according to the number of pull rollers (420D) only to a fraction of the spring force of the restoring spring (425) (first pulley block).

17. The injection device as claimed in claim 16, wherein the advancer spring (424) is connected to the receiving frame (412) via a traction wire (424B) which is guided over at least one pull roller (424D) on whose shaft the other end of the advancer spring (424) is held, so that the tensile force applied by the advancer spring (424) to the traction wire (424B) and thus to the advancer carriage (424D) is only a fraction of the spring force of the advancer spring (424) (second pulley block).

18. The injection device as claimed in claim 13, wherein:
    additional components are provided which produce a time delay (TV) between the completion of the injection procedure and the start of the return stroke (H3);
    and at least two toothed wheels mounted in a carriage (414, 415) and belonging to a pair of toothed wheels (413, 513) for gearing up or gearing down between the linear movement of the carriage (414, 514) and of the advancer carriage (423) are provided, on which at least one spring element engages for producing the strokes (H1, H2, H3) and the time delay (TV).

19. The injection device as claimed in claim 18, wherein the advancer carriage (423) is formed by a toothed belt (523).

20. The injection device as claimed in claim 1, wherein the actuating element includes a pull-out loading bar (320) which, when pulled out from the housing (310), pretensions at least one advancer spring (324) as energy accumulator, and a trigger mechanism (370) which, after activation, releases the injection carriage (340, 350) acted upon by the advancer spring (324) via an advancer carriage (323) for automatic execution of insertion stroke (H1), injection stroke (H2) and return stroke (H3).

21. The injection device as claimed in claim 20, wherein the pull-out loading bar (320), after it has been pulled out from the housing (310), pretensions at least one restoring spring (325) as energy accumulator for automatic return of the pull-out loading bar (320).

22. The injection device as claimed in claim 20, wherein the trigger mechanism (370) is coupled to at least one safety element (371) which in particular permits triggering only when the injection device is placed on the insertion site.

23. The injection device as claimed in claim 20, wherein the advancer spring (324) and the restoring springs (325) are scroll springs.

24. The injection device as claimed in claim 20, wherein the pull-out loading bar (320), advancer springs (324, 325), injection carriage (340, 350) and advancer carriage (323) are held in a receiving frame (312) in such a way that they can be displaced parallel to one another.

25. The injection device as claimed in claim 1, wherein, in order to control the operation of the injection device, in particular the sequence of insertion stroke (H1), injection stroke (H2) and return stroke (H3), control elements that can be brought into and out of positive/frictional engagement with one another are provided, in particular on the actuating element (120, 220, 320), on the syringe holder (140, 240, 340), on the ram (150, 250, 350) and on the housing (110, 210) or receiving frame (312).

26. The injection device as claimed in claim 25, wherein the control elements include elastic sections, locking cams, slide-on planes and cutouts.

27. The injection device as claimed in claim 1, wherein a damping unit (492) is assigned to the actuating element and/or to the injection carriage (440, 450).

28. The injection device as claimed in claim 1, wherein additional components are provided which produce a time delay (TV) between the completion of the injection procedure and the start of the return stroke (H3).

29. The injection device as claimed in claim 28, wherein the additional components cancel the frictional coupling between ram (450) and advancer carriage (423) as the advancer carriage (423) continues to move for the duration of the time delay (TV).

30. The injection device as claimed in claim 29, wherein the duration of the time delay (TV) is adjustable.

31. The injection device as claimed in claim 1, wherein a volume adapter (410) can be inserted into the ram (450) and predetermines the injection stroke (H2) and thus the quantity of a medicament that is administered during the injection stroke (H2).

* * * * *